(12) United States Patent
Cranley et al.

(10) Patent No.: US 7,794,994 B2
(45) Date of Patent: *Sep. 14, 2010

(54) ENZYME-BASED SYSTEM AND SENSOR FOR MEASURING ACETONE

(75) Inventors: Paul E. Cranley, Lake Jackson, TX (US); Jeffrey R. Allen, Poway, CA (US); Kristine L. Danowski, Midland, MI (US); James A. McIntyre, Midland, MI (US); Theodore E. Miller, Jr., Midland, MI (US); Bettina M. Rosner, La Jolla, CA (US); Alan D. Strickland, Lake Jackson, TX (US); Venkiteswaran Subramanian, San Diego, CA (US); Larry Sun, Sarnia (CA)

(73) Assignee: Kemeta, LLC, Mesa, AZ (US)

( * ) Notice: Subject to any disclaimer, the term of this patent is extended or adjusted under 35 U.S.C. 154(b) by 1051 days.

This patent is subject to a terminal disclaimer.

(21) Appl. No.: 10/494,923

(22) PCT Filed: Nov. 8, 2002

(86) PCT No.: PCT/US02/36028

§ 371 (c)(1),
(2), (4) Date: May 5, 2004

(87) PCT Pub. No.: WO03/039483

PCT Pub. Date: May 15, 2003

(65) Prior Publication Data

US 2005/0084921 A1 Apr. 21, 2005

Related U.S. Application Data

(60) Provisional application No. 60/332,349, filed on Nov. 9, 2001.

(51) Int. Cl.
*C12N 9/04* (2006.01)
*C12M 1/00* (2006.01)
*C07H 21/04* (2006.01)
*C12P 21/04* (2006.01)
*C12N 15/00* (2006.01)

(52) U.S. Cl. ............ 435/190; 435/69.1; 435/71.1; 435/440; 536/23.2; 205/403.01

(58) Field of Classification Search .............. None
See application file for complete search history.

(56) References Cited

U.S. PATENT DOCUMENTS

| | | | |
|---|---|---|---|
| 2,283,262 A | 5/1942 | Kamlet | |
| 3,838,033 A | 9/1974 | Mindt et al. | |
| 4,198,208 A | 4/1980 | Lerner et al. | |
| 4,352,885 A * | 10/1982 | Zeikus et al. | ............. 435/189 |
| 4,587,427 A | 5/1986 | Talbot et al. | |
| 4,882,499 A | 11/1989 | Luukkala et al. | |
| 4,931,404 A | 6/1990 | Kundu | |
| 4,935,346 A | 6/1990 | Phillips et al. | |
| 4,970,172 A | 11/1990 | Kundu | |
| 5,071,769 A | 12/1991 | Kundu | |
| 5,131,387 A | 7/1992 | French et al. | |
| 5,174,959 A | 12/1992 | Kundu et al. | |
| 5,236,567 A * | 8/1993 | Nanba et al. | ............. 204/403.1 |
| 5,303,575 A | 4/1994 | Brown et al. | |
| 5,355,425 A | 10/1994 | Braiman et al. | |
| 5,382,341 A | 1/1995 | Aroutiounian et al. | |
| 5,422,485 A | 6/1995 | Bowlds | |
| 5,426,032 A | 6/1995 | Phillips et al. | |
| 5,515,859 A | 5/1996 | Paz | |
| 5,543,621 A | 8/1996 | Sauke et al. | |
| 5,571,395 A | 11/1996 | Park et al. | |
| 5,628,890 A | 5/1997 | Carter et al. | |
| 5,656,142 A | 8/1997 | Park et al. | |
| 5,783,056 A | 7/1998 | Hampp et al. | |
| 5,900,533 A | 5/1999 | Chou | |
| 5,999,886 A | 12/1999 | Martin et al. | |

(Continued)

FOREIGN PATENT DOCUMENTS

DE 4007375 10/1990

(Continued)

OTHER PUBLICATIONS

Branden et al. Introduction to Protein Structure, Garland Publishing Inc., New York, p. 247, 1991.*

(Continued)

*Primary Examiner*—Yong D Pak
(74) *Attorney, Agent, or Firm*—Honigman Miller Schwartz and Cohn LLP; Noel E. Day; Jonathan P. O'Brien

(57) ABSTRACT

Described are enzyme systems specific for acetone and methods of using these enzyme systems to detect acetone in biological or environmental samples. Biosensors containing these enzyme systems are disclosed, in which detection of acetone may be achieved by linking electrochemical, photometric, or other detection means to one or more acetone-specific enzyme reactions or pathways. Methods of using such acetone-specific biosensors include subject management of weight loss, disease detection, and bioavailability monitoring of therapeutics.

7 Claims, 37 Drawing Sheets

U.S. PATENT DOCUMENTS

| | | | |
|---|---|---|---|
| 6,063,283 | A | 5/2000 | Shirota et al. |
| 6,244,096 | B1 | 6/2001 | Lewis et al. |
| 6,454,723 | B1 | 9/2002 | Montagnino |
| 6,467,333 | B2 | 10/2002 | Lewis et al. |
| 6,540,891 | B1 | 4/2003 | Stewart et al. |
| 6,558,321 | B1 | 5/2003 | Burd et al. |
| 6,609,068 | B2 | 8/2003 | Cranley et al. |
| 6,841,244 | B2 | 1/2005 | Foss et al. |
| 6,841,391 | B2 | 1/2005 | Lewis et al. |
| 6,984,307 | B2 | 1/2006 | Zweig |
| 7,364,551 | B2 * | 4/2008 | Allen et al. .............. 600/532 |
| 2001/0031913 | A1 | 10/2001 | Ito |
| 2001/0056328 | A1 | 12/2001 | Trippel |
| 2002/0007249 | A1 | 1/2002 | Cranley |
| 2003/0172808 | A1 | 9/2003 | Le Bec |
| 2003/0175992 | A1 | 9/2003 | Toranto |
| 2003/0175993 | A1 | 9/2003 | Toranto |
| 2003/0208133 | A1 | 11/2003 | Mault |
| 2004/0236244 | A1 | 11/2004 | Allen |

FOREIGN PATENT DOCUMENTS

| | | |
|---|---|---|
| EP | 0279069 A | 8/1988 |
| GB | 1082525 | 9/1967 |
| WO | 99/66304 | 12/1999 |
| WO | 00/20626 | 4/2000 |
| WO | 00/42422 | 7/2000 |
| WO | 01/08554 | 2/2001 |
| WO | 01/28416 | 4/2001 |
| WO | 01/63277 | 8/2001 |
| WO | 03/039483 | 5/2003 |
| WO | 03/050234 | 6/2003 |

OTHER PUBLICATIONS

Kleiner et al. Purification and properties of a secondary alcohol dehydrogenase from the parasitic protozoan *Tritrichomonas foetus*. J Biol Chem. Jul. 5, 1985;260(13):8038-43.*

Casazza J. P. et al.: "The metabolism of acetone in rat." The Journal of Biological Chemistry, Jan. 10, 1984, abstract, vol. 259, No. 1, Medline Database No. NLM6706932.

Sluis M. K. et al.: "Purification and characterization of acetone carboxylase from *Xanthobacter* strain Py2." Proceedings of the National Academy of Sciences of the U.S., Aug. 5, 1997, abstract, vol. 94, No. 16, Medline Database No. NLM9237998.

Abbott Laboratories, Inc. "Rational for Blood b-Hydroxybutyrate Testing." Dec. 1999, P/N 485340. Rev. 0.

Byrne et al. "Evalutation of an Electrochemical Sensor for Measuring Blood Ketones." Diabetes Care. Apr. 2000, vol. 23, No. 4: 500-503.

Sluis, Miriam K., et al., Purification and characterization of acetone carboxylase from *Xanthobacter* strain Py2, Proc. Natl. Acad. Sci. USA, Aug. 1997, 8456-8461, vol. 94.

Rooth, Gosta, et al., Acetone in Alveolar Air, and the Control of Diabetes, The Lancet, Nov. 19, 1966, 1102-1105.

Kundu, Samar K., et al., Breath Acetone Analyzer: Diagnostic Tool to Monitor Dietary Fat Loss, Clin. Chem. 39/1, (1993), 87-92.

Laffel, Lori, Ketone Bodies: a Review of Physiology, Pathophysiology and Application of Monitoring to Diabetes, Diabetes Metab Res Rev 1999; 15: 412-426.

Crofford, Oscar B., M.D., et al., Acetone in Breath and Blood, Transactions of the American Clinical and Climatological Association (1977), 88128-39.

Sluis, Miriam K., et al., Involvement of an ATP-Dependent Carboxylase in a CO2-Dependent Pathway of Acetone Metabolism by *Xanthobacter* Strain Py2, Journal of Bacteriology, Jul. 1996, 4020-4026, vol. 178, No. 14.

Ben-Bassat, A., et al., Ethanol Production by Thermophilic Bacteria: Metabolic Control of End Product Formation in *Thermoanaerobium brockii*, Journal of Bacteriology, Apr. 1981, vol. 146, No. 1, 192-199.

Burdette, Douglas S., et al., Cloning and expression of the gene encoding the *Thermoanaerobacter ethanolicus* 39E secondary-alcohol dehydrogenase and biochemical characterization of the enzyme, Biochem.J. (1996) 316, 115-122.

Coleman, J.P., et al., Purification and Characterization of the Secondary Alcohol Dehydrogenase from Propane-utilizing *Mycobacterium vaccae* Strain JOB-5, Journal of General Microbiology (1985) 131, 2901-2907.

Lamed, Raphael J., et al., Novel NADP-linked alcohol-aldehyde/ketone oxidoreductase in thermophilic ethanologenic bacteria, Biochem.J. (1981) 195, 183-190.

Al-Kassim, Loola S., et al., Studies of NADP+-preferred secondary alcohol dehydrogenase from *Thermoanaerobium brockii*, Ottawa-Carleton Chemistry Institute, Jul. 17, 1989, 907-913.

Sluis, Miriam K., et al., Biochemical, Molecular, and Genetic Analyses of the Acetone Carboxylases from *Xanthobacter autotrophicus* Strain Py2 and *Rhodobacter capsulatus* Strain B10, Journal of Bacteriology, Jun. 2002, vol. 184, No. 11, 2969-2977.

Smith, David, et al., Trace gases in breath of healthy volunteers when fasting and after a protein-calorie meal: a preliminary study, the American Physiological Society, 1999, 8750-7587/99, 1584-1588.

Clark, Daniel D., et al., Evidence for an Inducible Nucleotide-Dependent Acetone Carboxylase in *Rhodococcus rhodochrous* B276, Journal of Bacteriology, May 1999, 2752-2758.

Birks, Stephen J., et al., Assay and properties of acetone carboxylase, a novel enzyme involved in acetone-dependent growth and CO2, fixation in *Rhodobacter capsulatus* and other photosynthetic and denitrifying bacteria, Microbiology (1997), 143, 755-766.

Kuhn, Lance S., Biosensors: Blockbuster or Bomb? Electrochemical Biosensors for Diabetes Monitoring, The Electrochemical Society Interface, 1998, 26-31.

Ricco, Antonio J., Chemical Sensors, A Perspective of the Present and Future, The Electrochemical Society Interface, 1998, 18-24.

Tierney, M.J., et al., Electroanalysis of Glucose in Transcutaneously Extracted Samples, Electroanalysis 2000, 12, No. 9, 666-671.

Widdel, Friedrich, Growth of Methanogenic Bacteria in Pure Culture with 2-Propanol and Other Alcohols as Hydrogen Donors, Applied and Environmental Microbiology, May 1986, vol. 51, No. 5, 1056-1062.

Katakis, Ioanis, Catalytic Electrooxidation of NADH for Dehydrogenase Amperometric Biosensors, Mikrochimica Acta 126, 1997, 11-32.

Park, Je-Kyun, et al., Determination of breath alcohol using a differential-type amperometric biosensor based on alcohol dehydrogenase, Analytica Chimica Acta 390 (1999) 83-91.

Park, Je-Kyun, et al., Amperometric biosensor for determination of ethanol vapor, Biosensors & Bioelectronics 10 (1995) 587-594.

Yee, Hee-Jin, et al., Disposable thick-film amperometric biosensor with multiple working electrodes fabricated on a single substrate, Sensors and Actuators B 34 (1996) 490-492.

Pandey, P.C., et al., Ethanol Biosensors and Electrochemical Oxidation of NADH, Analytical Biochemistry 260 (1998), 195-203.

Vestal, J.R., et al., Divergent Metabolic Pathways for Propane and Propionate Utilization by a Soil Isolate, Journal of Bacteriology, Jul. 1969, 216-221.

Taylor, David G., et al., The Microbial Metabolism of Acetone, Journal of General Microbiology (1980), 118, 159-170.

Coleman, J.P., et al., Fate of the C1 Product of Propane Dissimilation in *Mycobacterium vaccae+*, Journal of Bacteriology, 1984, 1163-1164.

Koop, Dennis R., et al., Identification of Ethanol-inducible P-450 Isozyme 3a as the Acetone and Acetol Monooxygenase of Rabbit Microsomes, The Journal of Biological Chemistry, vol. 260, No. 25, Nov. 5, 1985, 13607-13612.

Platen, H., et al., Methanogenic degradation of acetone by an enrichment culture, Archives of Microbiology 149 (1987), 2, 136-141.

Platen, H., et al., Anaerobic degradation of acetone by *Desulfococcus biacutus* spec. nov., Archives of Microbiology 154 (Nov. 1990), 4, 355-361.

Bonnet-Smits, E.M., et al., Carbon Dioxide Fixation as the Initial Step in the Metabolism of Acetone by *Thiosphaera pantotropha*, Journal of General Microbiology (1988), 134, 2281-2289.

Ensign, Scott A., et al., New roles for CO2 in the microbial metabolism of aliphatic epoxides and ketones, Arch Microbiol (1998) 169, 179-187.

Willner, Itamar, et al., Integration of Layered Redox Proteins and Conductive Supports for Bioelectronic Applications, Angew. Chem. Int. Ed. 2000, 39, 1180-1218.

Shimao, Masayuki, et al., Existence of a Novel Enzyme, Pyrroloquinoline Quinone-Dependent Polyvinyl Alcohol Dehydrogenase, in a Bacterial Symbiont, *Pseudomonas* sp. Strain VM15C, Applied and Environmental Microbiology, Feb. 1986, 268-275.

Zheng, Ya-Jun, et al., Conformation of coenzyme pyrroloquinoline quinone and role of Ca2+ in the catalytic mechanism of quinoprotein methanol dehydrogenase, Proc. Natl. Acad. Sci. USA, Oct. 1997, vol. 94, 11881-11886.

Laemmli, U.K., Cleavage of Structural Proteins during the Assembly of the Head of Bacteriophage T4, Nature vol. 227, Aug. 15, 1970, 680-685.

Chromy, V., et al., Re-evaluation of EDTA-Chelated Biuret Reagent, Clinical Chemistry, vol. 20, No. 10, 1974, 1362-1363.

Sono, Masanori, et al., Heme-Containing Oxygenases, Chem. Rev. 1996, 96, 2841-2887.

Schuhmann, Wolfgang, et al., Electron-transfer pathways between redox enzymes and electrode surfaces: Reagentless biosensors based on thiol-monolayer-bound and polypyrrole-entrapped enzymes, The Royal Society of Chemistry 2000, Faraday Discuss., 116, 245-255.

Lv, Yi, et al., Chemiluminescence biosensor chip based on a microreactor using carrier air flow for determination of uric acid in human serum, The Royal Society of Chemistry 2002, Analyst, 127, 1176-1179.

Wang, Ching Hao, et al., Co-immobilization of polymeric luminol, iron (II) tris (5-aminophenanthroline) and glucose oxidase at an electrode surface, and its application as a glucose optrode, The Royal Society of Chemistry 2002, Analyst, 127, 1507-1511.

Rhines, Timothy D., et al., Fiber-Optic Biosensor for Urea Based on Sensing of Ammonia Gas, Analytic Chimica Acta, 227 (1989) 387-396.

Thompson, David, PhD, et al., Lifetime Health and Economic Consequences of Obesity, Arch Intern Med/vol. 159, Oct. 11, 1999, 2177-2183.

Ashraf, William, et al., Genetic, biochemical and immunological evidence for the involvement of two alcohol dehydrogenases in the metabolism of propane by *Rhodococcus rhodochrous* PNKb1, Arch Microbiol (1992) 157, 486-492.

Ashraf, William, et al., Purification and characterization of a NAD+-dependent secondary alcohol dehydrogenase from propane-grown *Rhodococcus rhodochrous* PNKb1, Arch Microbiol (1990) 153, 163-168.

Lamed, R.J., et al., Potential applications of an alcohol-aldehyde/ketone oxidoreductase from thermophilic bacteria, Eyzyme Microb. Technol., Apr. 1981, vol. 3, 144-148.

Wang, Joseph, et al., Organic-phase biosensing of secondary alcohols with a *Ta. brockii* alcohol dehydrogenase electrode, Biosensors & Bioelectronics 9 (1994), 225-230.

Dennison, Manus J., et al., Direct Monitoring of Formaldehyde Vapour and Detection of Ethanol Vapour Using Dehydrogenase-based Biosensors, Analyst, Dec. 1966, vol. 121, 1769-1773.

Elving, Philip J., et al., 524—NAD/NADH As A Model Redox System: Mechanism, Mediation, Modification by the Environment, Bioelectrochemistry and Bioenergetics, 9 (1982), 363-378.

Karyakin, Arkady A., et al., Electroreduction of NAD+ to enzymatically active NADH at poly (neutral red) modified electrodes, Journal of Electroanalytical Chemistry 399 (1995), 179-184.

Tkac, Jan, et al., Monitoring of dihydroxyacetone production during oxidation of glycerol by immobilized *Gluconobacter oxydans* cells with an enzyme biosensor, Enzyme and Microbial Technology, Mar. 8, 2001; 383-388, vol. 28, Issues 4-5.

Whittaker, MM, et al., Catalytic reaction profile for alcohol oxidation by galactose oxidase, Biochemistry 2001, vol. 40, No. 24.

Ashraf, William, et al., Bacterial oxidation of propane, Jan. 17, 2006, 1-6, vol. 122, Issue 1-2.

Casazza JP., et al., Serum acetone and liver acetone monoxygenase activity in pregnant rats, fetuses, and neonates: reversible pretranslational reduction of cytochrome (P450IIE1) during pregnancy, Arch Biochem Biophys. Feb. 15, 1994; 309(1): 111-6.

Platen, Harald, et al., Fermentative degradation of acetone by an enrichment culture in membrane-separated culture devices and in cell suspensions, FEMS Microbiology Letters, Jan. 17, 2006, 27-32, vol. 122 Issue 1-2.

Bondoc, Flordeliza Y., et al., Acetone catabolism by cytochrome P450 2E1: studies with CYP2E1-null mice, Biochemical Pharmacology, Aug. 1, 1999, 451-463, vol. 568, Issue 3.

Boujtita, Mohammed, et al., Development of a disposable ethanol biosensor based on a chemically modified screen-printed electrode coated with alcohol oxidase for the analysis of beer, Biosensors and Bioelectronics, Aug. 2000, 257-263, vol. 15, Issues 5-6.

Gonchar, Mykhailo, V., et al., Microbia O2- and H2O2-electrode sensors for alcohol assays based on the use of permeabilized mutuant yeast cells as the sensitive bioelements, Biosensors and Bioelectronics, Oct. 1998, 945-952, vol. 13, Issue 9.

Rank, M., et al., On-line monitoring of ethanol, acetaldehyde and glycerol during industrial fermentations with *Saccharomyces cerevisiae*, Applied Micorbiology and Biotechnology, Mar. 1995, 813-817, vol. 42, No. 6, Springer Berlin/Heidelberg.

Bataillard P., et al., An integrated silicon thermopile as biosensor for the thermal monitoring of glucose, urea and penicillin, Biosensors & Bioelectronics, 1993, 89-98, vol. 8.

Kroutil, R. T., et al., Automated Detection of Acetone, Methyl Ethyl Ketone, and Sulfur Hexafluouride by Direct Analysis of Fourier Transform Infared Interferograms, 1994, 724-732, vol. 48.

Iordanov, V.P., et al., Silicon thin-film UV filter for NADH fluorescence analysis, Sensors and Actuators A: Physical, Apr. 1, 2002, 161-166, vols. 97-98.

Gschwend, MH, et al., Optical detection of mitochondrial NADH content in intact human myotubes, Cell Mol Biol (Noisy-le-grand) 2001.

Leca, Beatrice D., et al., Screen-printed electrodes as disposable or reusable optical devices for luminol electrochemiluminescence, Sensors and Actuators B: Chemical, Apr. 15, 2001, 190-193, vol. 74, Issues 1-3.

Eunsook, S. Jin, et al., An Electrogenerated Chemiluminescence Imaging Fiber Electrode chemical Sensor for NADH, Electroanalysis, 1287-1290, vol. 13, Issue 15, (2001).

Atsushi, Seki, et al., Biosensors based on light-addressable potentiometric sensors for urea, penicillin and glucose, Analytica Chimica Acta, Nov. 2, 1998, 9-13, vol. 373, Issue 1.

Hou, CT, et al., Stereospecificity and other properties of a novel secondary-alcohol-specific alcohol dyhydrogenase, Eur J Biochem, Oct. 1981, 359-64.

Schutte, H., et al., Purificiation and characterization of a nicotinamide adenine dinucleotide-dependent secondary alcohol dehydrogenase from *Candida boidinii*, Biochim Biophys Acta, Jun. 16, 1982, 298-307.

Williams, Amy K., et al., Sol-Gel-Encapsulated Alcohol Dehydrogenase as a Versatile, Environmentally Stabilized Sensor for Alcohols and Aldehydes, J. Am. Chem. Soc., Apr. 18, 1998, 4366-4371, American Chemical Society.

Wang, Joseph, et al., Microseparation Chips for Performing Multienzymatic Dehydrogenase/Oxidase Assays: Simultaneous Electrochemical Measurement of Ethanol and Glucose, Anal. Chem., Feb. 8, 2001, 1296-1300, American Chemical Society.

Hollmann, Frank, et al., The First Synthetic Application of a Monooxygenase Employing Indirect Electrochemical NADH Regeneration, Angewandte Chemie International Edition, Jan. 4, 2001, 169-171, vol. 40, Issue 1, Wiley-VCH Verlag GmbH & Co. KGaA, Weinheim.

Argall, M E, et al., The use of trehalose-stabilized lyophilized methanol deyhdrogenase from *Hyphomicrobium* X for the detection of methanol, Biochem-Mol-Biol-Int. Jul. 1993, 491-7.

Batchelor M.J., et al., Amperometic assay for the ketone body 3-hydroxybutyrate, Analytica chimica acta, 1989, 289-294, vol. 221.

Shin-Ichiro, Suye, et al., Mediated amperometric determination of ammonia with a methanol dehydrogenase from *Pseudomonas* sp.

AM-1 immobilized carbon past electrode, Biosensors and Bioelectronics, 1996, 529-534, vol. 11, Issue 5.

Eggenstein, Claudia, et al., A disposable biosensor for urea determination in blood based on an ammonium-sensitive transducer, Biosensors and Biolelectronics, Jan. 1999, 33-41, vol. 14, Issue 1.

Hart, JP, et al., Development of a disposable amperometric NH4+ biosensor based on a chemically modified screen-printed carbon electrode coated with glutamate dehydrogenase, 2-oxoglutarate, and NADH, Electroanalysis, 1999, vol. 11, No. 6.

Carlson, M. A., et al., An automated, handheld biosensor for aflatoxin, Biosensors and Bioelectronics, Jan. 2000, 841-848, vol. 14, Issues 10-11.

* cited by examiner

Figure 3

| Substrate | Specific activity ($\mu mol \cdot min^{-1} \cdot mg^{-1}$ at pH 6.2) |
|---|---|
| acetone | 43 ± 1.4 |
| 2-butanone | 73 ± 5.3 |
| 2-pentanone | 85 ± 4.9 |
| 3-pentanone | 78 ± 1.7 | reductive ⟶

$$H_3C-\underset{acetone}{\overset{O}{C}}-CH_3 \;\underset{NADH+H^+ \;\; NAD^+}{\rightleftharpoons}\; H_3C-\underset{isopropanol}{\overset{OH}{\underset{H}{C}}}-CH_3$$

SEQUENCE LISTING

```
<160> NUMBER OF SEQ ID NOS: 19

<210> SEQ ID NO 1
<211> LENGTH: 776
<212> TYPE: PRT
<213> ORGANISM: Xanthobacter autotrophicus Py2
<220> FEATURE:
<221> NAME/KEY: DOMAIN
<222> LOCATION: 1..776
<223> OTHER INFORMATION: Acetone carboxylase, alpha subunit

<400> SEQUENCE: 1

Met Asn Val Thr Val Asp Gln Ser Thr Leu Ala Gly Ala Thr Arg Gly
1               5                   10                  15

Ile Val Arg Gly Gly Glu Thr Leu Lys Glu His Arg Asp Arg Leu Met
            20                  25                  30

Ala Ala Thr Lys Ala Thr Gly Arg Tyr Ala Gly Leu Lys Thr Leu Glu
        35                  40                  45

Leu Arg Glu Arg Glu Pro Ile Leu Tyr Asn Lys Leu Phe Ser Arg Leu
    50                  55                  60
```

```
Arg Ala Gly Val Val Asp Ala Arg Glu Thr Ala Lys Lys Ile Ala Ala
 65                  70                  75                  80

Ser Pro Ile Val Glu Gln Glu Gly Glu Leu Cys Phe Thr Leu Tyr Asn
                 85                  90                  95

Ala Ala Gly Asp Ser Leu Leu Thr Ser Thr Gly Ile Ile His Val
            100                 105                 110

Gly Thr Met Gly Ala Ala Ile Lys Tyr Met Ile Glu Asn Asn Trp Glu
            115                 120                 125

Ala Asn Pro Gly Val His Asp Lys Asp Ile Phe Cys Asn Asn Asp Ser
    130                 135                 140

Leu Ile Gly Asn Val His Pro Cys Asp Ile His Thr Ile Val Pro Ile
145                 150                 155                 160

Phe Trp Glu Gly Glu Leu Ile Gly Trp Val Gly Gly Val Thr His Val
                165                 170                 175

Ile Asp Thr Gly Ala Val Gly Pro Gly Ser Met Ala Thr Gly Gln Val
            180                 185                 190

Gln Arg Phe Gly Asp Gly Tyr Ser Ile Thr Cys Arg Lys Val Gly Ala
    195                 200                 205

Asn Asp Thr Leu Phe Arg Asp Trp Leu His Glu Ser Gln Arg Met Val
    210                 215                 220

Arg Thr Thr Arg Tyr Trp Met Leu Asp Glu Arg Thr Arg Ile Ala Gly
225                 230                 235                 240

Cys His Met Ile Arg Lys Leu Val Glu Glu Val Val Ala Glu Glu Gly
                245                 250                 255

Ile Glu Ala Tyr Trp Lys Phe Ala Tyr Glu Ala Val Glu His Gly Arg
            260                 265                 270

Leu Gly Leu Gln Ala Arg Ile Lys Ala Met Thr Ile Pro Gly Thr Tyr
        275                 280                 285

Arg Gln Val Gly Phe Val Asp Val Pro Tyr Ala His Glu Asp Val Arg
    290                 295                 300

Val Pro Ser Asp Phe Ala Lys Leu Asp Thr Ile Met His Ala Pro Cys
305                 310                 315                 320

Glu Met Thr Ile Arg Arg Asp Gly Thr Trp Arg Leu Asp Phe Glu Gly
                325                 330                 335

Ser Ser Arg Trp Gly Trp His Thr Tyr Asn Ala His Gln Val Ser Phe
            340                 345                 350

Thr Ser Gly Ile Trp Val Met Met Thr Gln Thr Leu Ile Pro Ser Glu
        355                 360                 365

Met Ile Asn Asp Gly Ala Ala Tyr Gly Thr Glu Phe Arg Leu Pro Lys
    370                 375                 380

Gly Thr Trp Met Asn Pro Asp Asp Arg Arg Val Ala Phe Ser Tyr Ser
385                 390                 395                 400

Trp His Phe Leu Val Ser Ala Thr Ala Leu Trp Arg Gly Leu Ser
                405                 410                 415

Arg Ser Tyr Phe Gly Arg Gly Tyr Leu Glu Glu Val Asn Ala Gly Asn
            420                 425                 430

Ala Asn Thr Ser Asn Trp Leu Gln Gly Gly Phe Asn Gln Tyr Asp
        435                 440                 445

Glu Ile His Ala Val Asn Ser Phe Glu Cys Ala Ala Asn Gly Thr Gly
    450                 455                 460

Ala Thr Ala Val Gln Asp Gly Leu Ser His Ala Ala Ile Trp Asn
465                 470                 475                 480
```

```
Pro Glu Gly Asp Met Gly Asp Met Glu Ile Trp Glu Leu Ala Glu Pro
            485                 490                 495

Leu Val Tyr Leu Gly Arg Gln Ile Lys Ala Ser Ser Gly Gly Ser Gly
            500                 505                 510

Lys Tyr Arg Gly Gly Cys Gly Phe Glu Ser Leu Arg Met Val Trp Asn
            515                 520                 525

Ala Lys Asp Trp Thr Met Phe Phe Met Gly Asn Gly His Ile Ser Ser
            530                 535                 540

Asp Trp Gly Leu Met Gly Gly Tyr Pro Ala Ala Ser Gly Tyr Arg Phe
545                 550                 555                 560

Ala Ala His Lys Thr Asn Leu Lys Glu Leu Ile Ala Ser Gly Ala Glu
            565                 570                 575

Ile Pro Leu Gly Gly Asp Thr Asp Pro Glu Asn Pro Thr Trp Asp Ala
            580                 585                 590

Met Leu Pro Asp Ala Gln Ile Lys Arg Asp Lys Gln Ala Ile Thr Thr
            595                 600                 605

Glu Glu Met Phe Ser Asp Tyr Asp Leu Tyr Leu Asn Tyr Met Arg Gly
            610                 615                 620

Gly Pro Gly Phe Gly Asp Pro Leu Asp Arg Pro Gln Ala Val Ala
625                 630                 635                 640

Asp Asp Ile Asn Gly Gly Tyr Val Leu Glu Arg Phe Ala Gly Glu Val
            645                 650                 655

Tyr Gly Val Val Val Arg Lys Gly Ala Asp Gly Gln Tyr Gly Val Asp
            660                 665                 670

Glu Ala Gly Thr Ala Ala Ala Arg Ala Gln Ile Arg Lys Asp Arg Leu
            675                 680                 685

Ala Lys Ser Val Pro Val Ser Glu Trp Met Lys Gly Glu Arg Glu Lys
            690                 695                 700

Ile Leu Ala Lys Asp Ala Gly Thr Gln Val Arg Gln Met Phe Ala Ala
705                 710                 715                 720

Ser Phe Lys Leu Gly Pro Arg Phe Glu Lys Asp Phe Arg Thr Phe Trp
            725                 730                 735

Ser Leu Pro Asp Ser Trp Thr Leu Pro Glu Glu Glu Ile Gly Val Pro
            740                 745                 750

Thr Tyr Gly Ser Arg Tyr Ser Met Asp Ile Ser Glu Leu Pro Asp Val
            755                 760                 765

His Thr Val Gln Phe Val Glu Glu
            770                 775

<210> SEQ ID NO 2
<211> LENGTH: 717
<212> TYPE: PRT
<213> ORGANISM: Xanthobacter autotrophicus Py2
<220> FEATURE:
<221> NAME/KEY: DOMAIN
<222> LOCATION: 1..717
<223> OTHER INFORMATION: Acetone carboxylase, beta subunit

<400> SEQUENCE: 2

Met Asn Val Pro Val Gly His Leu Arg Asn Val Gln Val Leu Gly Ile
1               5                   10                  15

Asp Ala Gly Gly Thr Met Thr Asp Thr Phe Phe Val Asp Gln Asp Gly
            20                  25                  30

Asp Phe Val Val Gly Lys Ala Gln Ser Thr Pro Gln Asn Glu Ala Leu
        35                  40                  45

Gly Leu Ile Ala Ser Ser Glu Asp Gly Leu Ala Asn Trp Gly Met Ser
```

```
            50                  55                  60
Leu His Glu Ala Leu Ala Gln Leu Gln Thr Gly Val Tyr Ser Gly Thr
 65                  70                  75                  80

Ala Met Leu Asn Arg Val Val Gln Arg Lys Gly Leu Lys Cys Gly Leu
                 85                  90                  95

Ile Val Asn Arg Gly Met Glu Asp Phe His Arg Met Gly Arg Ala Val
                100                 105                 110

Gln Ser His Leu Gly Tyr Ala Tyr Glu Asp Arg Ile His Leu Asn Thr
            115                 120                 125

His Arg Tyr Asp Pro Pro Leu Val Pro Arg His Leu Thr Arg Gly Val
130                 135                 140

Val Glu Arg Thr Asp Met Ile Gly Thr Gln Val Ile Pro Leu Arg Glu
145                 150                 155                 160

Asp Thr Ala Arg Asp Ala Ala Arg Asp Leu Ile Ala Ala Asp Ala Glu
                165                 170                 175

Gly Ile Val Ile Ser Leu Leu His Ser Tyr Lys Asn Pro Glu Asn Glu
                180                 185                 190

Arg Arg Val Arg Asp Ile Val Leu Glu Glu Val Glu Lys Ser Gly Lys
            195                 200                 205

Lys Ile Pro Val Phe Ala Ser Ala Asp Tyr Tyr Pro Val Arg Lys Glu
210                 215                 220

Thr His Arg Thr Asn Thr Thr Ile Leu Glu Gly Tyr Ala Ala Glu Pro
225                 230                 235                 240

Ser Arg Gln Thr Leu Ser Lys Ile Ser Asn Ala Phe Lys Glu Arg Gly
                245                 250                 255

Thr Lys Phe Asp Phe Arg Val Met Ala Thr His Gly Gly Thr Ile Ser
                260                 265                 270

Trp Lys Ala Lys Glu Leu Ala Arg Thr Ile Val Ser Gly Pro Ile Gly
            275                 280                 285

Gly Val Ile Gly Ala Lys Tyr Leu Gly Glu Val Leu Gly Tyr Lys Asn
            290                 295                 300

Ile Ala Cys Ser Asp Ile Gly Gly Thr Ser Phe Asp Val Ala Leu Ile
305                 310                 315                 320

Thr Gln Gly Glu Met Thr Ile Lys Asn Asp Pro Asp Met Ala Arg Leu
                325                 330                 335

Val Leu Ser Leu Pro Leu Val Ala Met Asp Ser Val Gly Ala Gly Ala
                340                 345                 350

Gly Ser Phe Ile Arg Leu Asp Pro Tyr Thr Arg Ala Ile Lys Leu Gly
            355                 360                 365

Pro Asp Ser Ala Gly Tyr Arg Val Gly Val Cys Trp Lys Glu Ser Gly
370                 375                 380

Ile Glu Thr Val Thr Ile Ser Asp Cys His Met Val Leu Gly Tyr Leu
385                 390                 395                 400

Asn Pro Asp Asn Phe Leu Gly Gly Ala Val Lys Leu Asp Arg Gln Arg
                405                 410                 415

Ser Val Asp Ala Ile Lys Ala Gln Ile Ala Asp Pro Leu Gly Leu Ser
                420                 425                 430

Val Glu Asp Ala Ala Gly Val Ile Glu Leu Leu Asp Ser Asp Leu
            435                 440                 445

Arg Asp Tyr Leu Arg Ser Met Ile Ser Gly Lys Gly Tyr Ser Pro Ala
450                 455                 460

Ser Phe Val Cys Phe Ser Tyr Gly Gly Ala Gly Pro Val His Thr Tyr
465                 470                 475                 480
```

Gly Tyr Thr Glu Gly Leu Gly Phe Glu Asp Val Ile Val Pro Ala Trp
                485                 490                 495

Ala Ala Gly Phe Ser Ala Phe Gly Cys Ala Ala Asp Phe Glu Tyr
            500                 505                 510

Arg Tyr Asp Lys Ser Leu Asp Ile Asn Met Pro Thr Glu Thr Pro Asp
            515                 520                 525

Thr Asp Lys Glu Lys Ala Ala Thr Leu Gln Ala Ala Trp Glu Glu
    530                 535                 540

Leu Thr Lys Asn Val Leu Glu Glu Phe Lys Leu Asn Gly Tyr Ser Ala
545                 550                 555                 560

Asp Gln Val Thr Leu Gln Pro Gly Tyr Arg Met Gln Tyr Arg Gly Gln
                565                 570                 575

Leu Asn Asp Leu Glu Ile Glu Ser Pro Leu Ala Gln Ala His Thr Ala
            580                 585                 590

Ala Asp Trp Asp Gln Leu Thr Asp Ala Phe Asn Ala Thr Tyr Gly Arg
            595                 600                 605

Val Tyr Ala Ala Ser Ala Arg Ser Pro Glu Leu Gly Tyr Ser Val Thr
    610                 615                 620

Gly Ala Ile Met Arg Gly Met Val Pro Ile Pro Lys Pro Lys Ile Pro
625                 630                 635                 640

Lys Glu Pro Glu Glu Gly Glu Thr Pro Pro Glu Ser Ala Lys Ile Gly
                645                 650                 655

Thr Arg Lys Phe Tyr Arg Lys Lys Arg Trp Val Asp Ala Gln Leu Tyr
            660                 665                 670

His Met Glu Ser Leu Arg Pro Gly Asn Arg Val Met Gly Pro Ala Val
            675                 680                 685

Ile Glu Ser Asp Ala Thr Thr Phe Val Val Pro Asp Gly Phe Glu Thr
    690                 695                 700

Trp Leu Asp Gly His Arg Leu Phe His Leu Arg Glu Val
705                 710                 715

<210> SEQ ID NO 3
<211> LENGTH: 168
<212> TYPE: PRT
<213> ORGANISM: Xanthobacter autotrophicus Py2
<220> FEATURE:
<221> NAME/KEY: DOMAIN
<222> LOCATION: 1..168
<223> OTHER INFORMATION: Acetone carboxylase, gamma subunit

<400> SEQUENCE: 3

Met Ala Tyr Thr Arg Ser Lys Ile Val Asp Leu Val Asp Gly Lys Ile
1               5                   10                  15

Asp Pro Asp Thr Leu His Gln Met Leu Ser Thr Pro Lys Asp Pro Glu
            20                  25                  30

Arg Phe Val Thr Tyr Val Glu Ile Leu Gln Glu Arg Met Pro Trp Asp
        35                  40                  45

Asp Lys Ile Ile Leu Pro Leu Gly Pro Lys Leu Phe Ile Val Gln Gln
    50                  55                  60

Lys Val Ser Lys Lys Trp Thr Val Arg Cys Glu Cys Gly His Asp Phe
65                  70                  75                  80

Cys Asp Trp Lys Asp Asn Trp Lys Leu Ser Ala Arg Val His Val Arg
                85                  90                  95

Asp Thr Pro Gln Lys Met Glu Glu Ile Tyr Pro Arg Leu Met Ala Pro
            100                 105                 110

```
Thr Pro Ser Trp Gln Val Ile Arg Glu Tyr Phe Cys Pro Glu Cys Gly
            115                 120                 125

Thr Leu His Asp Val Glu Ala Pro Thr Pro Trp Tyr Pro Val Ile His
    130                 135                 140

Asp Phe Ser Pro Asp Ile Glu Gly Phe Tyr Gln Glu Trp Leu Gly Leu
145                 150                 155                 160

Pro Val Pro Glu Arg Ala Asp Ala
                165

<210> SEQ ID NO 4
<211> LENGTH: 769
<212> TYPE: PRT
<213> ORGANISM: Rhodobacter capsulatus B10
<220> FEATURE:
<221> NAME/KEY: DOMAIN
<222> LOCATION: 1..769
<223> OTHER INFORMATION: Acetone carboxylase, alpha subunit
      (Capsulapedia No. RRC02651)

<400> SEQUENCE: 4

Met Asn Ala Pro Thr Ala Ile Arg Gly Ile Val Arg Gly Gly Asp Thr
1               5                   10                  15

Leu Lys Gln His Arg Asp Gly Ile Met Glu Ala Ser Lys Arg Thr Gly
            20                  25                  30

His Tyr Ala Gly Leu Lys Gln Met Glu Leu Arg Asp Ser Asp Pro Ile
        35                  40                  45

Met Tyr Asn Lys Leu Phe Ser Arg Leu Arg Ala Gly Val Val Asp Ala
    50                  55                  60

Arg Glu Thr Ala Lys Lys Ile Ala Ala Ser Pro Ile Val Glu Gln Glu
65                  70                  75                  80

Gly Glu Leu Cys Phe Thr Leu Tyr Asn Ala Ala Gly Asp Ser Ile Leu
                85                  90                  95

Thr Ser Thr Gly Ile Ile Ile His Val Gly Thr Met Gly Ala Ala Ile
            100                 105                 110

Lys Tyr Met Ile Glu Asn Asp Trp Glu Ser Asn Pro Gly Val Lys Asp
        115                 120                 125

Arg Asp Ile Phe Cys Asn Asn Asp Ser Leu Ile Gly Asn Val His Pro
    130                 135                 140

Cys Asp Ile His Thr Ile Val Pro Ile Phe His Glu Gly Glu Leu Ile
145                 150                 155                 160

Gly Trp Val Gly Gly Val Thr His Val Ile Asp Thr Gly Ala Val Gly
                165                 170                 175

Pro Gly Ser Met Thr Thr Gly Gln Val Gln Arg Phe Gly Asp Gly Tyr
            180                 185                 190

Ser Val Thr Cys Arg Lys Val Gly Glu Asn Asp Thr Leu Phe Arg Asp
        195                 200                 205

Trp Leu His Glu Ser Gln Arg Ser Val Arg Thr Thr Arg Tyr Trp Met
    210                 215                 220

Leu Asp Glu Arg Thr Arg Ile Ala Gly Cys His Met Ile Arg Lys Leu
225                 230                 235                 240

Val Ala Glu Val Ile Ala Glu Gly Ile Glu Ala Tyr Trp Lys Phe
                245                 250                 255

Ala Tyr Glu Ala Val Glu His Gly Arg Leu Gly Leu Gln Asn Arg Ile
            260                 265                 270

Lys Ala Met Thr Ile Pro Gly Lys Tyr Arg Gln Val Gly Phe Val Asp
        275                 280                 285
```

```
Val Pro Tyr Ala His Asp Asp Val Arg Val Pro Ser Asp Phe Ala Lys
    290                 295                 300

Val Asp Thr Ile Met His Thr Pro Ser Glu Met Thr Ile Arg Pro Asp
305                 310                 315                 320

Gly Thr Trp Arg Leu Asp Phe Glu Gly Ala Ser Arg Trp Gly Trp His
                325                 330                 335

Thr Tyr Asn Ala His Ser Val Ser Phe Thr Ser Gly Ile Trp Val Met
            340                 345                 350

Met Thr Gln Thr Leu Ile Pro Thr Glu Met Ile Asn Asp Gly Ala Ala
        355                 360                 365

Tyr Gly Thr Glu Phe Arg Leu Pro Lys Gly Thr Trp Met Asn Pro Asp
    370                 375                 380

Asp Arg Arg Val Ala Phe Ala Tyr Ser Trp His Phe Leu Val Ser Ser
385                 390                 395                 400

Trp Thr Ala Leu Trp Arg Gly Leu Ser Arg Ser Tyr Phe Gly Arg Gly
                405                 410                 415

Tyr Leu Glu Glu Val Asn Ala Gly Asn Ala Asn Thr Ser Asn Trp Leu
            420                 425                 430

Gln Gly Gly Gly Phe Asn Gln Tyr Asp Glu Ile His Ala Val Asn Ser
        435                 440                 445

Phe Glu Cys Ala Ala Asn Gly Val Gly Ala Ser Ala Ile Gly Asp Gly
    450                 455                 460

Leu Ser His Ala Ala Ala Ile Trp Asn Pro Glu Gly Asp Met Gly Asp
465                 470                 475                 480

Met Glu Ile Trp Glu Leu Ala Glu Pro Leu Val Tyr Leu Gly Arg Gln
                485                 490                 495

Ile Lys Ala Ser Ser Gly Gly Ala Gly Lys Tyr Arg Gly Gly Cys Gly
            500                 505                 510

Phe Glu Ser Leu Arg Met Val Trp Asn Ala Lys Asp Trp Thr Met Phe
        515                 520                 525

Phe Met Gly Asn Gly His Ile Ser Ser Asp Trp Gly Leu Met Gly Gly
    530                 535                 540

Tyr Pro Ala Ala Ser Gly Tyr Arg Phe Glu Ala His Glu Thr Gly Leu
545                 550                 555                 560

Lys Glu Ile Ile Ala Gln Gly Gly Asp Ile Pro His Gly Gly Asp Thr
                565                 570                 575

Asp Pro Gly Asn Pro Val Trp Asp Gly Leu Leu Lys Gly Ala Arg Ile
            580                 585                 590

Lys Arg Asp Lys Gln Ala Ile Thr Thr Glu Ala Met Phe Lys Asp Tyr
        595                 600                 605

Asp Leu Tyr Leu Asn Tyr Met Arg Gly Gly Pro Gly Phe Gly Asp Pro
    610                 615                 620

Leu Asp Arg Asp Pro Gly Ala Val Ala Ala Asp Val Asn Gly Gly Tyr
625                 630                 635                 640

Leu Val Glu Arg Phe Ala Gln Ser Val Tyr Gly Val Val Leu Val Lys
                645                 650                 655

Gly Ala Asp Gly Leu Leu Ala Ala Asp Ala Ala Thr Glu Ala Arg
            660                 665                 670

Arg Ala Ala Ile Arg Lys Asp Arg Leu Ala Lys Ala Val Pro Thr Ala
        675                 680                 685

Glu Trp Met Lys Gly Glu Arg Asp Arg Ile Leu Lys Lys Glu Ala Gly
    690                 695                 700

Val His Val Gln Gln Met Phe Ala Ala Ser Phe Lys Leu Gly Pro Lys
```

```
                   705                 710                 715                 720
Trp Glu Glu Gly Phe Arg Lys Phe Trp Asp Leu Pro Ile Asp Trp Arg
                725                 730                 735

Leu Met Glu Ala Asp Leu Pro Ile Pro Ser Tyr Gly Arg Asp Tyr Ser
                740                 745                 750

Met Asp Leu Ser Glu Leu Pro Asp Val Lys Thr Val Gln Phe Val Glu
            755                 760                 765

Glu

<210> SEQ ID NO 5
<211> LENGTH: 717
<212> TYPE: PRT
<213> ORGANISM: Rhodobacter capsulatus B10
<220> FEATURE:
<221> NAME/KEY: DOMAIN
<222> LOCATION: 1..717
<223> OTHER INFORMATION: Acetone carboxylase, beta subunit
      (Capsulapedia No. RRC02652)

<400> SEQUENCE: 5

Met Pro Leu Asp Arg Glu Lys Thr Arg Ser Val Gln Val Leu Gly Ile
1               5                   10                  15

Asp Ala Gly Gly Thr Met Thr Asp Thr Phe Phe Val Asp Ala Asn Gly
                20                  25                  30

Asp Phe Val Val Gly Lys Ala Gln Ser Thr Pro Gln Asn Glu Ala Leu
            35                  40                  45

Gly Leu Leu Glu Ser Ser Arg Glu Gly Leu Gln His Trp Gly Leu Ser
        50                  55                  60

Leu Glu Glu Ala Leu Ser Ser Ile Gln Thr Gly Val Tyr Ser Gly Thr
65                  70                  75                  80

Ala Met Leu Asn Arg Val Val Gln Arg Lys Gly Leu Arg Cys Gly Leu
                85                  90                  95

Ile Val Asn Ala Gly Met Glu Asp Phe His Arg Met Gly Arg Ala Ile
                100                 105                 110

Gln Ala Tyr Leu Gly Phe Ala Tyr Glu Asp Arg Ile His Leu Asn Thr
            115                 120                 125

His Tyr Tyr Asp Glu Pro Leu Val Pro Arg His Leu Thr Arg Gly Val
        130                 135                 140

Met Glu Arg Ile Asp Met Phe Gly Asp Val Val Ile Pro Leu Arg Glu
145                 150                 155                 160

Glu Thr Ala Arg Gln Ala Ala Glu Leu Ile Ala Gln Asp Val Glu
                165                 170                 175

Gly Ile Val Ile Ser Leu Leu His Ser Tyr Lys Asn Pro Ala His Glu
            180                 185                 190

Arg Arg Val Arg Asp Ile Val Ala Glu Glu Leu Glu Lys Ala Gly Lys
        195                 200                 205

Thr Thr Pro Val Phe Ala Ser Thr Asp Tyr Tyr Pro Val Arg Lys Glu
    210                 215                 220

Thr His Arg Thr Asn Thr Thr Ile Leu Glu Ala Tyr Ala Ala Glu Pro
225                 230                 235                 240

Ser Arg Gln Thr Leu Arg Lys Ile Thr Gly Ala Phe Lys Glu Asn Gly
                245                 250                 255

Ser Arg Phe Asp Phe Arg Val Met Ala Thr His Gly Gly Thr Ile Ser
            260                 265                 270

Trp Lys Ala Lys Glu Leu Ala Arg Thr Ile Val Ser Gly Pro Ile Gly
        275                 280                 285
```

-continued

```
Gly Val Ile Gly Ala Lys Tyr Leu Gly Glu Val Leu Gly Tyr Lys Asn
            290                 295                 300
Ile Ala Cys Ser Asp Ile Gly Thr Ser Phe Asp Val Ala Leu Ile
305                 310                 315                 320
Thr Gln Asn Glu Leu Thr Ile Arg Asn Asp Pro Met Ala Arg Leu
                325                 330                 335
Val Leu Ser Leu Pro Leu Val Ala Met Asp Ser Val Gly Ala Gly Ala
                340                 345                 350
Gly Ser Phe Ile Arg Leu Asp Pro Tyr Thr Lys Ala Ile Lys Leu Gly
            355                 360                 365
Pro Asp Ser Ala Gly Tyr Arg Val Gly Val Cys Trp Ala Glu Ser Gly
370                 375                 380
Ile Glu Thr Val Thr Ile Ser Asp Cys His Val Ile Leu Gly Tyr Leu
385                 390                 395                 400
Asn Pro Asp Asn Phe Leu Gly Gly Gln Val Lys Leu Asp Arg Gln Arg
                405                 410                 415
Ala Trp Asp Ala Met Lys Thr Gln Ile Ala Asp Pro Leu Gly Leu Ser
            420                 425                 430
Val Glu Asp Ala Ala Ala Gly Val Ile Glu Leu Leu Asp Ser Asp Leu
            435                 440                 445
Arg Asp Tyr Leu Arg Ser Met Ile Ser Gly Lys Gly Tyr Ser Pro Ser
            450                 455                 460
Ser Phe Thr Cys Phe Ser Tyr Gly Gly Ala Gly Pro Val His Thr Tyr
465                 470                 475                 480
Gly Tyr Thr Glu Gly Leu Gly Phe Glu Asp Val Ile Val Pro Ala Trp
                485                 490                 495
Ala Ala Gly Phe Ser Ala Phe Gly Cys Ala Ala Ala Asp Phe Glu Tyr
            500                 505                 510
Arg Tyr Asp Lys Ser Leu Asp Leu Asn Ile Ala Arg Asp Gly Ser Asp
            515                 520                 525
Asp Leu Lys Ala His Glu Ala Arg Thr Leu Asn Asp Ala Trp His Glu
    530                 535                 540
Leu Thr Glu Arg Val Leu Glu Glu Phe Glu Leu Asn Gly Tyr Thr Arg
545                 550                 555                 560
Asp Gln Val Lys Leu Gln Pro Gly Phe Arg Met Gln Tyr Arg Gly Gln
                565                 570                 575
Leu Asn Asp Leu Glu Ile Glu Ser Pro Ile Pro Ala Ala Lys Thr Ala
            580                 585                 590
Ala Asp Trp Asp Lys Leu Val Ala Ala Phe Asn Asp Thr Tyr Gly Arg
            595                 600                 605
Val Tyr Ala Ala Ser Ala Arg Ser Pro Glu Leu Gly Tyr Ser Val Thr
610                 615                 620
Gly Ala Ile Met Arg Gly Met Val Pro Ile Pro Lys Pro Lys Ile Pro
625                 630                 635                 640
Lys Glu Pro Glu Thr Gly Ala Thr Pro Pro Glu Ala Ala Lys Leu Gly
                645                 650                 655
Thr Arg Lys Phe Tyr Arg Lys Lys Lys Trp Val Asp Ala Arg Leu Tyr
            660                 665                 670
Arg Met Glu Lys Leu Leu Pro Gly Asn Arg Ile Thr Gly Pro Ala Ile
            675                 680                 685
Ile Glu Ser Asp Ala Thr Thr Phe Val Val Pro Asp Gly Phe Glu Thr
    690                 695                 700
```

```
Trp Leu Asp Gly His Arg Leu Phe His Leu Lys Glu Val
705                 710                 715
```

```
<210> SEQ ID NO 6
<211> LENGTH: 167
<212> TYPE: PRT
<213> ORGANISM: Rhodobacter capsulatus B10
<220> FEATURE:
<221> NAME/KEY: DOMAIN
<222> LOCATION: 1..167
<223> OTHER INFORMATION: Acetone carboxylase, gamma subunit
      (Capsulapedia No. RRC04094)

<400> SEQUENCE: 6
```

```
Met Ala Tyr Thr Lys Ala Lys Ile Lys Asp Leu Val Asp Gly Lys Ile
1               5                   10                  15

Asp Arg Asp Thr Leu His Thr Met Leu Ala Thr Pro Lys Asp Ala Asp
                20                  25                  30

Arg Phe Val Met Tyr Leu Glu Val Leu Gln Asp Gln Val Pro Trp Glu
            35                  40                  45

Asp Arg Ile Ile Leu Pro Leu Gly Pro Lys Leu Tyr Ile Val Gln Arg
        50                  55                  60

Lys Ser Asp His Lys Trp Val Val Lys Ser His Ala Gly His Glu Phe
65                  70                  75                  80

Cys Asp Trp Arg Glu Asn Trp Lys Leu His Ala Val Met Arg Val Arg
                85                  90                  95

Glu Thr Pro Glu Ala Met Glu Glu Ile Tyr Pro Arg Leu Met Ala Pro
            100                 105                 110

Thr Ala Gly Trp Gln Val Ile Arg Glu Tyr Tyr Cys Pro Leu Ser Gly
        115                 120                 125

Asp Leu Leu Asp Val Glu Ala Pro Thr Pro Trp Tyr Pro Val Ile His
    130                 135                 140

Asp Phe Glu Pro Asp Ile Asp Ala Phe Tyr Ser Glu Trp Leu Gly Leu
145                 150                 155                 160

Lys Ile Pro Glu Arg Ala Ala
                165
```

```
<210> SEQ ID NO 7
<211> LENGTH: 14
<212> TYPE: PRT
<213> ORGANISM: Xanthobacter autotrophicus Py2
<220> FEATURE:
<221> NAME/KEY: DOMAIN
<222> LOCATION: 1..14
<223> OTHER INFORMATION: Secondary alcohol dehydrogenase, N-terminal
      tetradecapeptide

<400> SEQUENCE: 7
```

```
Met Lys Gly Leu Val Tyr Arg Gly Pro Gly Lys Lys Ala Leu
1               5                   10
```

```
<210> SEQ ID NO 8
<211> LENGTH: 12
<212> TYPE: PRT
<213> ORGANISM: Xanthobacter autotrophicus Py2
<220> FEATURE:
<221> NAME/KEY: DOMAIN
<222> LOCATION: 1..12
<223> OTHER INFORMATION: Secondary alcohol dehydrogenase, tryptic
      fragment
<220> FEATURE:
<221> NAME/KEY: UNSURE
<222> LOCATION: 9..9
<223> OTHER INFORMATION: Phe9 may be Ser9
```

```
<400> SEQUENCE: 8

Pro Val Ala Val Asp His Gly Pro Phe Pro His Lys
1               5                   10

<210> SEQ ID NO 9
<211> LENGTH: 8
<212> TYPE: PRT
<213> ORGANISM: Xanthobacter autotrophicus Py2
<220> FEATURE:
<221> NAME/KEY: DOMAIN
<222> LOCATION: 1..8
<223> OTHER INFORMATION: Secondary alcohol dehydrogenase, tryptic
      fragment
<220> FEATURE:
<221> NAME/KEY: UNSURE
<222> LOCATION: 3..3
<223> OTHER INFORMATION: Leu3 may be Ile3

<400> SEQUENCE: 9

Gly Gly Leu Gly Val Tyr His Gln
1               5

<210> SEQ ID NO 10
<211> LENGTH: 9
<212> TYPE: PRT
<213> ORGANISM: Xanthobacter autotrophicus Py2
<220> FEATURE:
<221> NAME/KEY: DOMAIN
<222> LOCATION: 1..9
<223> OTHER INFORMATION: Secondary alcohol dehydrogenase, tryptic
      fragment
<220> FEATURE:
<221> NAME/KEY: UNSURE
<222> LOCATION: 2..2
<223> OTHER INFORMATION: Leu2 may be Ile2

<400> SEQUENCE: 10

Ala Leu Glu Glu Val Pro His Pro Arg
1               5

<210> SEQ ID NO 11
<211> LENGTH: 7
<212> TYPE: PRT
<213> ORGANISM: Xanthobacter autotrophicus Py2
<220> FEATURE:
<221> NAME/KEY: DOMAIN
<222> LOCATION: 1..7
<223> OTHER INFORMATION: Secondary alcohol dehydrogenase, tryptic
      fragment

<400> SEQUENCE: 11

His Pro Ser Gly Asp Thr Arg
1               5

<210> SEQ ID NO 12
<211> LENGTH: 9
<212> TYPE: PRT
<213> ORGANISM: Xanthobacter autotrophicus Py2
<220> FEATURE:
<221> NAME/KEY: DOMAIN
<222> LOCATION: 1.9
<223> OTHER INFORMATION: Secondary alcohol dehydrogenase, tryptic
      fragment

<400> SEQUENCE: 12

Gly Leu Val Tyr Arg Gly Pro Gly Lys
1               5
```

```
<210> SEQ ID NO 13
<211> LENGTH: 7
<212> TYPE: PRT
<213> ORGANISM: Xanthobacter autotrophicus Py2
<220> FEATURE:
<221> NAME/KEY: DOMAIN
<222> LOCATION: 1.7
<223> OTHER INFORMATION: Secondary alcohol dehydrogenase, tryptic
      fragment
<220> FEATURE:
<221> NAME/KEY: UNSURE
<222> LOCATION: 3.3
<223> OTHER INFORMATION: Ile3 may be Leu3

<400> SEQUENCE: 13

His Gln Ile Ala Ser Ser Arg
1               5

<210> SEQ ID NO 14
<211> LENGTH: 6
<212> TYPE: PRT
<213> ORGANISM: Xanthobacter autotrophicus Py2
<220> FEATURE:
<221> NAME/KEY: DOMAIN
<222> LOCATION: 1.6
<223> OTHER INFORMATION: Secondary alcohol dehydrogenase, fragment

<400> SEQUENCE: 14

Leu Asp Asn Val Pro Glu
1               5

<210> SEQ ID NO 15
<211> LENGTH: 6
<212> TYPE: PRT
<213> ORGANISM: Xanthobacter autotrophicus Py2
<220> FEATURE:
<221> NAME/KEY: DOMAIN
<222> LOCATION: 1.6
<223> OTHER INFORMATION: Secondary alcohol dehydrogenase, fragment

<400> SEQUENCE: 15

Phe Asp Gln Arg Gln Pro
1               5

<210> SEQ ID NO 16
<211> LENGTH: 8
<212> TYPE: PRT
<213> ORGANISM: Xanthobacter autotrophicus Py2
<220> FEATURE:
<221> NAME/KEY: DOMAIN
<222> LOCATION: 1.8
<223> OTHER INFORMATION: Secondary alcohol dehydrogenase, fragment

<400> SEQUENCE: 16

Gly Ala Gly Arg Ile Ile Ala Val
1               5

<210> SEQ ID NO 17
<211> LENGTH: 7
<212> TYPE: PRT
<213> ORGANISM: Xanthobacter autotrophicus Py2
<220> FEATURE:
<221> NAME/KEY: DOMAIN
<222> LOCATION: 1.7
<223> OTHER INFORMATION: Secondary alcohol dehydrogenase, fragment

<400> SEQUENCE: 17

Gln Val Glu Pro Leu Met Ser
                5
```

```
<210> SEQ ID NO 18
<211> LENGTH: 9
<212> TYPE: PRT
<213> ORGANISM: Xanthobacter autotrophicus Py2
<220> FEATURE:
<221> NAME/KEY: DOMAIN
<222> LOCATION: 1.6
<223> OTHER INFORMATION: Secondary alcohol dehydrogenase, fragment

<400> SEQUENCE: 18

Phe Phe Ala Asp Ile Ile Glu Ala Ala
1               5

<210> SEQ ID NO 19
<211> LENGTH: 6
<212> TYPE: PRT
<213> ORGANISM: Xanthobacter autotrophicus Py2
<220> FEATURE:
<221> NAME/KEY: DOMAIN
<222> LOCATION: 1.6
<223> OTHER INFORMATION: Secondary alcohol dehydrogenase, fragment

<400> SEQUENCE: 19

Asp Thr Val Thr Thr His
1               5
```

ENZYME-BASED SYSTEM AND SENSOR FOR MEASURING ACETONE

CROSS-REFERENCE

This application is a national phase entry of PCT Application No. PCT/US2002/036028 filed on Nov. 8, 2002, which claims priority to U.S. Provisional application No. 60/332,349 filed on Nov. 9, 2001, the contents of which are incorporated herein by reference in their entireties.

BACKGROUND OF THE INVENTION

1. Field of the Invention

This invention relates to the field of acetone detection. Acetone-specific enzyme systems and sensors capable of qualitatively and/or quantitatively detecting acetone have now been developed. These enzyme systems can be incorporated into relatively inexpensive, simple and/or portable enzyme-based sensors particularly suited for detecting acetone in environmental or biological samples, for example, mammalian breath samples.

2. Description of Related Art

Acetone Sources

Acetone may be detected in liquids and gases present in or obtained from biological organisms and various environments. For example, acetone may be detected in environments such as: natural environments, including soils, sediments, streams, or wetlands; indoor and outdoor work and home environments; and waste environments, including waste storage ponds and waste disposal sites. Acetone may be found in environmental and biological liquids and gases due to introduction of acetone to the environment or organism from an external source. Thus, environmental acetone may result from leakage, leaching, waste discharge, or solvent evaporation, or from emission of combustion gases released by burning wood or plastic or by operating petrochemical internal combustion engines. Likewise, in a living organism, acetone may be present due to ingestion, inhalation, or absorption from an external source.

Acetone may also be found in such environmental and biological liquids and gases due to internal generation of acetone by the environment tested (whether by chemical reaction or by biological production) or by the organism tested (for example, microbes, animals, etc.). Thus, the published literature reports that, acetone:

occurs as a biodegradation product of sewage, solid wastes and alcohols, and as an oxidation product of humic substances. Acetone has been detected in a variety of plants and foods including onions, grapes, cauliflower, tomatoes, morning glory, wild mustard, milk, beans, peas, cheese and chicken breast. Natural emissions from a variety of tree species contain acetone vapour.

J D Reisman, *Environmental Health Criteria for Acetone* (Draft), Environmental Health Criteria No. 207, International Programme on Chemical Safety (INCHEM) (1998). For example, acetone may form chemically within an environment by atmospheric oxidation of plant terpenes (Fruekilde et al. (1998)).

Living organisms may internally generate acetone via a number of enzymatic routes. In microbes, acetone may be synthesized, for example: by oxidation of isopropanol, as may be performed by *Mycobacterium* spp., including *M. vaccae*; by desulfonation of 2-propanesulfonate, as may be performed by *Rhodococcus* spp. and *Comamonas* spp., including *C. acidovorans*; and by decarboxylation of acetoacetate, as may be performed by *Clostridium* spp., including *C. acetobutylicum, C. butyricum,* and *C. saccharoperhutylacetonium*.

In the vertebrate animals, including humans, the most common route of acetone synthesis is by ketone body formation. Ketone bodies are compounds produced from the oxidation of lipids by the liver and used as an energy source when glucose is not readily available. The main compounds classified as ketone bodies include acetoacetic acid, β-hydroxybutyric acid, and acetone. Ketones are always present in the body, and their levels increase during fasting and prolonged exercise. Oxidation of fatty acids in liver mitochondria produces acetyl-coenzyme A, which can be further oxidized via the citric acid cycle or undergo a process called ketogenesis. Ketogenesis occurs primarily when glucose is not available as an energy source and converts acetyl-coenzyme A to acetoacetate or β-hydroxybutyrate. The liver releases acetoacetate and β-hydroxybutyrate to the bloodstream where it is carried to peripheral tissues and is used as an alternative energy source. Acetoacetate is a β-ketoacid and slowly undergoes spontaneous non-enzymatic decarboxylation to acetone and $CO_2$ (Scheme 1).

Scheme 1

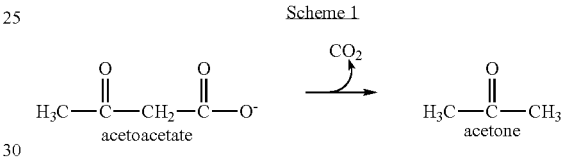

In tetrapod vertebrates, including mammals, the acetone thus formed is detectable in respiration as a result of blood gas exchange in the lung.

Breath acetone levels have been correlated with blood acetone levels and so may be used as an accurate indicator of blood acetone content. Thus, elevated breath acetone levels have been demonstrated, in clinical studies of otherwise healthy human subjects, to be a reliable indicator of fat metabolism and projected weight loss. Acetone is present in human breath at endogenous levels of about 0.2-0.5 ppm (v/v) and increases to and above 5-25 ppm for otherwise healthy individuals on long term, low carbohydrate diets. Similarly, breath acetone concentrations increase in individuals on a high-fat diet. Each of these dietary conditions is called a "benign dietary ketosis." Breath acetone concentration likewise increases during short-term fasting, a condition known as "fasting ketosis," and after prolonged exercise, a condition known as "post-exercise ketosis." Under starvation conditions (or long-term fasting) or in diabetics whose insulin levels drop too low, the concentration of breath acetone may become abnormally high (up to 70 ppm or higher), indicating conditions called, respectively, "metabolic ketoacidosis" or "diabetic ketoacidosis," diabetic ketoacidosis being a potentially fatal condition. In each of these conditions, elevated acetone levels can be detected in the breath of juveniles or adults.

In addition to acetone elevation by benign dietary, fasting, and post-exercise ketosis, and by diabetic and metabolic ketoacidosis, other conditions and diseases can also generate elevated blood acetone, and thereby elevated breath acetone, levels. For example, blood acetone elevation is also observed in, for example: 1) the female reproductive cycle (for example, during pregnancy or during the post-partum interval preceding resumption of ovulation); 2) the neonatal stage of development; 3) hypoglycemia (for example, hypoglycemia of childhood or hypoglycemia caused by eating disorders or prolonged vomiting); 4) inborn metabolic diseases (for example, maple syrup urine disease); 5) liver dysfunction (for example, end-stage liver disease or hepatic ischemia); 6) glucocorticoid deficiency; 7) growth hormone deficiency; 8) acute pancreatitis resulting from viral infection (for example, systemic cytomegalovirus infection); 9) treatment with nucleoside analogs (for example, in anti-retroviral therapy for HIV); 10) isopropanol ingestion or intoxication; 11) ethanol intoxication; and 12) salicylate intoxication. In these conditions, too, acetone can be detected by, for example, breath analysis of children or adults.

Thus, detection of acetone can be useful in a number of medically important applications. For example, medical reports have identified obesity as a primary risk factor in diabetes, hypertension, coronary heart disease, hypercholesterolemia and stroke. In many cases of obesity, a controlled weight loss program can reverse these serious life-threatening diseases. Acetone is a metabolite that can be detected to monitor the progress in and compliance with such a weight loss program. Similarly, detection of acetone can be used to alert diabetic subjects to the onset of ketoacidosis or to obtain a preliminary indication of the need to diagnose a subject for any of the other medical conditions or diseases in which elevated acetone may be found. Therefore, acetone is a key diagnostic metabolite that can be used as a means to monitor diet compliance, weight loss progress, medical treatment regimen compliance, diabetes, and health wellness in subjects of all ages.

The Field of Acetone Detection

Acetone can be detected in any of the above-described situations, by use of various means. A wide variety of means for acetone detection are known in the art, including those for detecting acetone from liquid solution (for example, blood and plasma analysis, urine testing) and those for detecting acetone from gas mixtures (for example, breath sampling, ambient gas monitoring). A broad assortment of different methodologies have been employed in acetone detection, monitoring; and analysis. These methodologies include those relying on, for example: color indicator, optical reflection, heat-of-combustion, electrical resistance, gas chromatography (GC), liquid chromatography (LC), photometry, colorimetry, ultraviolet spectrometry (UV), infra-red spectroscopy and spectrometry (IR), microwave spectroscopy, and mass spectrometry (MS) technologies.

These technologies, and thus the methodologies employing them, vary in their specificity: some detect a broad range of volatile organic compounds (VOCs); some detect either ketones (and ketoacids) alone or both ketones (and ketoacids) and aldehydes; and some detect acetone specifically.

In a first group of acetone detection methodologies, acetone is monitored by use of any of a variety of technologies that detect a broad range of VOCs, examples of which technologies include the following. Ambient gas monitors that detect a broad range of VOCs include, for example: the Dräger Polytron SE Ex detector, which employs a catalytic, heat-of-combustion "pellisitor" type sensor (catalog no. 68 09 760; 0.60 kilograms); and the Dräger Polytron IR Ex gas detector, which uses an infrared sensor (catalog no. 83 12 550; 1.9 kilograms) (both available from Dräger Sicherheitstechnik GmbH, Lübeck, Germany).

Fluid-solid interaction-based detection of VOCs relies upon gas or liquid adsorption onto a solid phase (optionally including a chemical derivatization reaction), followed by colorimetric or photometric detection of the adsorbed and/or derivatized compound(s). Such fluid-solid interaction technologies are discussed in British Patent No. 1082525, which discloses detection of organic compounds containing active or activated hydrogen atoms, wherein metal zeolites are used as the solid. VOC detection involving liquid adsorption onto solid and utilizing photometric detection is discussed in U.S. Pat. No. 4,882,499. This patent teaches a liquid detector utilizing fiber optics to detect changes in optical coefficient of reflection of liquid sample absorbed by capillary action; a hydrophobic fibrous or sintered matrix is used as the adsorptive solid for this purpose.

In another approach to VOC detection, gas that adsorbs onto a solid is sensed by electrical resistance/conductivity detection: this is described in U.S. Pat. No. 5,382,341. This patent describes a process of manufacturing smoke-detecting elements in which a bismuth oxide film is deposited onto a substrate layer, and, thereafter, is electrically connected to a means for measuring resistance. In this case, the solid may comprise bismuth oxides, Bi—Fe-oxides, Bi—V-oxides, or Bi—Mo-oxides. Similarly, German Patent No. 028062 describes a gas adsorption method in which the solid comprises an adsorbent layer of a semiconductor device.

A further methodology for VOC detection relies upon a gas phase chemical derivatization (halogenation) reaction to produce a detectable halogenated product. Examples of such gas phase derivatization methodologies for VOC detection are taught in U.S. Pat. No. 4,198,208 (describing reaction with chlorine and detection of chlorinated species) and in German Publication No. 4007375. All of the technologies in this first group are capable of, and taught for, detecting acetone, though non-specifically as a member of the class of VOCs.

A second group of methodologies used for acetone detection are those that detect ketones/ketoacids or both ketones/ketoacids and aldehydes generally. The technologies utilized in these methods depend on chemical derivatization of, for example, acetone, to produce a colored product. The colored product can then be visually inspected to obtain a qualitative result. Similarly, the colored product can be visually compared with a color standard chart to obtain a semi-quantitative reading. Alternatively, the degree of coloration can be quantitatively assessed by means of colorimetry or photometry. The most common derivatization reactions employed in these technologies are those based on: 1) reaction with salicylaldehyde; 2) reaction with hydrazine (or a phenylhydrazine, for example, 2,4-dinitrophenylhydrazine); and 3) reaction with nitroprusside. Many other chemical derivatization reactions are known, but are not commonly employed, for detection of aldehydes and ketones/ketoacids (including acetone), because those reactions use high temperatures or caustic, non-durable, or expensive reagents that make widespread use impractical.

In salicylaldehyde-based assays, the ketone or ketoacid is introduced to an alkaline solution containing salicylaldehyde, whereupon an orange or red derivative is produced. For example, both acetone and acetoacetate may be detected in urine by this route, as disclosed in U.S. Pat. No. 2,283,262.

In hydrazine-based and phenylhydrazine-based assays, aldehydes, ketones, and ketoacids are derivatized to form one or more hydrazone or phenylhydrazone compounds. For example, gas phase acetone absorption into liquid solution for chemical derivatization by this route is described: in U.S. Pat. No. 4,931,404, which discloses derivatization by reaction with a hydrazine- or phenylhydrazine-coupled cation exchange matrix, followed by colorimetric detection of the, for example, yellow, derivative; and in British Patent No. 2253910, which discloses derivatization by reaction with a hydrazine solution, followed by electrical resistance detection of the derivative.

In nitroprusside-based assays, aldehydes, ketones, and ketoacids are reacted with nitroprusside, that is a salt of nitroprussic acid (for example, sodium nitroprusside, that is sodium nitroferricyanide), to form a derivative(s) that, in the presence of an amine, forms a pink or purple complex. In some methods, the amine is present during the nitroprusside reaction for immediate coloration, while in others, an amine-containing solution is added later to develop the color. The nitroprusside reaction is the one most commonly used to detect acetone in the context of personal health monitoring, for example, in diabetes or in weight loss. Such nitroprusside methodology is typically found in one of three different formats: gas sampling tubes, fluid testing strips, and fluid testing tablets.

A variety of nitroprusside tube assay devices are commonly used. One of the most common is the Draeger tube (that is the Dräger tube), for example, the Draeger acetone detector tube (catalog no. DRAG CH22901 from SAFECO, Inc., Knoxville, Tenn.). The Draeger acetone detector tube can be used for breath analysis, but is mainly employed for ambient gas sampling in which a pump draws an air sample through the tube. A similar assay employs the Draeger Chip Measurement System (catalog no. 540-CMS from Safety First of Middleton, Wis.; 0.74 kilograms) which utilizes a "chip," that is a planar, parallel array of Draeger tubes of capillary dimension. This hand-held device pumps a gas sample into the capillary tube(s), and the optics and electronics within the device perform colorimetry to convert the degree of coloration of the derivative within the tube into a quantitative digital signal. Similarly, methods for quantitatively monitoring acetone (and other ketones) in gas samples by photometric detection of the colored derivative, are taught in manufacturer information available with MSA acetone detector tubes (catalog no. 226620, available from Ben Meadows Co., a subsidiary of Lab Safety Supply Inc., PO Box 5277, Janesville, Wis. 53547). Also, U.S. Pat. No. 5,174,959 discloses a nitroprusside tube assay device containing two solid matrices: a nitroprusside-coupled matrix and an amine-coupled matrix. The device may be used with gas samples, in which case a solvent such as methanol is added, or with liquid samples such as urine.

Nitroprusside fluid testing strips and tablets are typically marketed as urine ketone test strips and tablets. Examples of such ketone test strip products are CHEMSTRIP K (produced by Roche Diagnostics Corp., Indianapolis, Ind.,) and KETO-STIX (produced by Bayer Corp., Diagnostics Division, Tarrytown, N.Y.). Exemplary ketone test tablets include the AMES ACETEST reagent tablets (catalog no. AM-2381, available from Analytical Scientific, Ltd., San Antonio, Tex.).

A third group of methodologies are acetone-specific. These acetone-specific detection methodologies utilize analytical devices and techniques. For example, acetone-specific detection methodologies include: gas chromatography detection; liquid chromatography detection using a micro-column, as disclosed in U.S. Pat. No. 6,063,283; and mass spectrometry detection, as described in U.S. Pat. No. 5,999,886, for use in the context of acetone vapor detection in semiconductor wafer processing chambers.

Specific detection of acetone in fluids by IR spectroscopy is disclosed in U.S. Pat. No. 5,355,425 (for liquids) and U.S. Pat. No. 4,587,427 (for gases). Specific detection of acetone in gases by FTIR spectrometry is disclosed in R T Kroutil et al., "Automated Detection of Acetone, Methyl Ethyl Ketone, and Sulfur Hexafluoride by Direct Analysis by Fourier-Transform Infrared Interferograms," *Applied Spectroscopy* 48(6): 724-32 (June 1994). Specific detection of acetone in gases by microwave spectroscopy is described in the abstract of Medical Technology Co-Operation Offer 131.C, entitled "Microwave Gas Spectroscopy for the Analysis of Exhaled Air," from the Nizhny Novgorod Region Cooperation of the East-West Agency (OWA) of the Association for Innovation Research and Consultation mbH of the Innovation Consulting Institute (InnovationsBeratungsInstitut, Dusseldorf, Del.).

In addition, a number of acetone-specific detection methods employing hyphenated analytical techniques are also well known in the art. For example, a selection of such methods, including those relying on GC-HPLC, GC-FID ("Flame Ionization Detector"), GC-MS, GC-RGD ("Reduction Gas Detector"), and HPLC-UV techniques, are described in J D Reisman, *Environmental Health Criteria for Acetone* (Draft), Environmental Health Criteria No. 207, International Programme on Chemical Safety (INCHEM) (1998).

Thus, gas (into liquid) absorption with chemical reactions, gas (onto solid) adsorption with and without chemical reactions, liquid (onto solid) adsorption with and without chemical reactions, gas phase chemical reactions, solution phase chemical reactions, UV, IR, GC, LC, MS, and other technologies have all been used for acetone detection. However, all of these technologies have drawbacks.

For example, it is desirable, for environmental, health, and safety reasons, to select an acetone detection method that is specific for acetone. This is especially important in the area of subject self-monitoring, for example, for diabetes and for dieting. Thus, broad VOC detection technologies are less desirable for these purposes. While the acetone-specific methodologies currently in use are specific for acetone, they require bulky equipment that is not easily transportable and is relatively expensive to obtain and maintain, and they are impractical for use by individuals lacking medical or scientific training. It is desirable for acetone detection technology to be light-weight, readily transportable, low cost, and easy-to-use. These features are also especially important in the area of subject self-monitoring. Thus, the currently available acetone-specific detection technologies are less desirable for these purposes and reasons.

In contrast to these acetone-specific technologies, most of the currently available methodologies that detect ketones/ketoacids or both ketones/ketoacids and aldehydes generally are relatively inexpensive, light-weight, readily transportable, and easy-to-use. Yet, without the use of a secondary detection system, such as colorimetry or photometry, these tests produce only a qualitative or semi-quantitative result: a visualized color reading. Second, these tests are not specific for acetone: the presence of acetoacetate, other ketones, and aldehydes can result in a falsely intensified color reading. Finally, these tests are susceptible of producing false positive and false negative results; the former falsely indicate the presence of elevated acetone, the latter falsely indicate the absence of elevated acetone. For example, in the most commonly used assays (nitroprusside assays): false positive results often occur with subjects taking, for example, sulfhydryl drugs such as captopril, or when other ketones or aldehydes are present; and false negative results often occur when testing highly acidic samples, for example, samples of urine from subjects taking large doses of vitamin C (ascorbic acid). It is desirable for acetone detection technology to be reliable, to be specific for acetone, and to be capable of producing a directly quantitative result. These features are also especially important in the area of subject self-monitoring. Thus, the currently available ketone/ketoacid and aldehyde detection technologies are less desirable for these purposes.

Therefore, a need exists in the field of acetone detection for an acetone detection technology that is acetone-specific, light-weight, readily transportable, low cost, easy-to-use, reliable, and capable of producing a directly quantitative result. It would also be advantageous for such a technology to be capable of producing an electronic result, for example, a digital result (or in the case of a photonic-type computer or other instrument, capable of producing a photonic result). Affordable, disposable, specific, single-use devices for monitoring acetone levels in biological samples by, for example, a subject at home, are not readily available.

Other fields, such as the field of ethanol detection, utilize enzyme-based technologies. Enzyme-based technologies can be analyte-specific and can take the form of light-weight, readily transportable, low cost, easy to use, and quantitative devices. For example, in the field of ethanol detection in biological samples, gas phase ethanol detection has been performed by means of an enzyme-linked electrochemical sensor, using either alcohol oxidase (AOX) or primary alcohol dehydrogenase (ADH) as the enzyme. In one, exemplary ethanol detection system, a thick-film, screen-printed enzyme electrode using ADH/$NAD^+$ immobilized in hydroxyethylcellulose is utilized for monitoring ethanol vapor. This ethanol-detecting enzyme electrode is activated by dipping it into buffer, the ethanol-containing sample is applied, and the resulting NADH produced by enzymatic action is monitored amperometrically at 650 mV (vs. Ag/AgCl). A similar electrode has been described for measuring ethanol vapor, wherein ADH is immobilized in reverse micelle media. The ethanol is partitioned into the aqueous phase where it is effectively concentrated in the medium where ADH can act upon it. These technologies are readily adaptable to easily transportable, low-cost detectors that can be used to monitor or self-monitor breath ethanol at home, at work, and in other environments remote from clinics and testing laboratories. However, these devices are not designed for, and the enzymes utilized (for example, primary alcohol dehydrogenase) are not capable of, acetone detection. Thus, if it could be devised, an enzyme-based technology might be able to offer many of the benefits needed in the field of acetone detection.

Nevertheless, all of the above-described acetone detection methods and devices rely on non-enzymatic technologies. Enzymatic measurement of acetone in environmental and biological samples has not been described to date. Thus, it appears that, in addition to the need for an acetone detection technology having the advantageous features described above, the field of acetone detection is also lacking the use of, and thus the benefits of, enzyme-based technologies.

SUMMARY OF THE INVENTION

The present invention is directed to enzyme-based detection systems that are acetone-specific, including acetone-specific, enzyme-based detection systems that are light-weight, readily transportable, low cost, easy-to-use, reliable, capable of producing a directly quantitative result, and capable of producing an electronic result. The capability of producing an electronic, for example, digital, result makes such a device readily adaptable to computerized data collection and transmission via a communication network such as the Internet (through either hard-wired or wireless means), including via the methodologies described in WO 01/63277. Such computerized data collection and transmission would permit methods of using the acetone-specific detectors of the present invention to be especially useful for compliance monitoring, coaching, and instructing.

In comparison with the currently available, lightweight, readily transportable, low cost, easy-to-use acetone detection technologies, the acetone-specific, enzyme-based detection systems of the present invention also offer improved sensitivity of acetone detection. None of the above-referenced documents suggests improving the sensitivity of acetone detection via enzymatic methodologies. Enzyme-based measurement of acetone in mammalian biological samples has not been described to date. However, as discussed above, specific detection of acetone can be critically important in a wide variety of medical conditions, and would be especially useful in the context of subject self-monitoring. However, such acetone-specific detection technologies are not generally available outside the laboratory or clinic setting, nor practical for regular subject self-monitoring. For these reasons, a need exists to provide improved, less cumbersome, and easier-to-use methods and devices for the specific detection of acetone in biological samples. Thus, detection of acetone by means of acetone-specific enzyme-based detectors according to the present invention would be particularly useful in a number of medically important applications.

Acetone-specific enzyme systems useful in quantitatively measuring acetone levels in biological samples have been created to address the problems with the state of the art technology. The enzyme systems and detectors of the present invention selectively act upon acetone as a substrate. The term "selectively" is intended to characterize an enzyme, system, or device that exhibits substantially greater affinity for or activity toward acetone over other potentially-available substrates, that is: an enzyme that is preferential for acetone among other chemical species normally present in a sample, for example, human breath, and/or an enzyme that (in the context of the acetone detectors of the present invention) would not appreciably come into contact with other substrates significantly competitive with acetone. Accordingly, in the systems and devices of the present invention, enzyme interactions with substrates other than acetone or reactive acetone derivatives are negligible.

One or more enzyme systems may be combined in a device, such as a biosensor, to facilitate sample measurement. Enzyme interaction with acetone may be directly or indirectly detected by various detection methods known in the art. These enzyme systems are useful in, for example, an in-home device for determination of acetone levels in human biological samples, such as breath, saliva, or urine, thereby providing a non-invasive means for monitoring subject wellness and/or for monitoring subject compliance with weight loss diets, health management programs, and treatment regimens.

Accordingly, an aspect of the invention is an acetone-specific enzyme system that couples enzyme-mediated metabolism of acetone to electrochemically detectable signals produced via one or more of the signal mediators described hereinabove. Specifically, an acetone-specific enzyme system, including an enzyme that selective targets acetone as a substrate, coupled to a detectable signal mediator is a preferred aspect of this invention, especially where the detection is performed by use of electrochemical or photometric means. Any acetone-specific enzyme capable of linking to an electrochemically detectable co-factor or by-product may be suitable for the enzyme system of this invention.

The acetone-specific enzyme system may be present in a lyophilized form until contacting the biological sample. Moreover, the electrochemical biosensor, according to the invention as described above, may comprise an acetone-specific enzyme system that is storage stabilized by the presence of a disaccharide, such as trehalose. The biological sample may be either in liquid or vapor form, but is preferably in vapor form.

An important feature for enzyme-mediated quantitation of acetone in samples such as human breath is use of an enzyme system having high acetone sensitivity (for example, a lower detection limit in the range of about 0.2-0.5 ppm (v/v)) that may be incorporated into a device. Additionally the enzyme system must be robust, stable, and relatively inexpensive. Optimally, the device should be capable of computer-interfacing, highly selective, portable, and have low interference from other metabolites found in breath, such as ethanol. Enzyme electrode technology (biosensors) is particularly suitable to meet these requirements, where selective enzymatic reactions are involved, due to the sensitivity of detection and the relatively simple instrumentation needed. Electrochemical detection depends on the direct measurement of current generated by the reaction of the detected species at the electrode. Coupling oxidoreductase (redox) enzyme reactions to electrodes has been an attractive approach to developing biosensors. In particular, electrochemical detection of reduced nicotinamide adenine dinucleotide (NADH) or hydrogen peroxide has been utilized in amperometric biosensors for a range of substrates, namely glucose (that is the reactions of glucose dehydrogenase and glucose oxidase respectively).

The acetone-specific enzyme system preferably contains an acetone-specific enzyme selected from the group consisting of acetone mono-oxygenase, acetone carboxylase, and secondary alcohol dehydrogenase. In particular, the inventive acetone-specific enzyme system preferably contains an acetone-specific enzyme system selected from the group consisting of acetone carboxylase product formation coupled to NAD(P)H oxidation, acetone carboxylase ATP-hydrolysis coupled to NAD(P)H oxidation, acetone carboxylase ATP hydrolysis coupled to $H_2O_2$ formation, secondary alcohol dehydrogenase (S-ADH) coupled to NAD(P)H oxidation, S-ADH catalyzed NAD(P)$^+$ formation coupled to $H_2O_2$ production, and acetone mono-oxygenase coupled to NAD(P)H oxidation.

In still another preferred embodiment, the acetone-specific enzyme system according to the invention contains a signal mediator selected from the group consisting of organic cofactors, inorganic cofactors, multi-electron transfer mediators and enzyme reaction by-products. Preferably, a signal from the electrochemically detectable signal mediator is linearly or exponentially amplified by magnifying electrochemical signal output via recycling enzyme substrates.

In a preferred embodiment of the invention, the acetone-specific enzyme system contains an acetone-utilizing enzyme obtained from a vertebrate or microbe, more preferably from a mammal, fungus, bacterium, or Archaeon.

In another preferred embodiment of the invention, the acetone-specific enzyme system contains secondary alcohol dehydrogenase obtained from a mammal or from a microorganism selected from aerobic and anaerobic bacteria, yeast, fungi, and methanogenic Archaea. Preferably, a secondary alcohol dehydrogenase is isolated from a species of *Thermoanerobium, Xanthobacter, Pseudomonas, Rhodococcus*, or *Mycobacterium*; especially preferred is a secondary alcohol dehydrogenase isolated from *Xanthobacter autotrophicus* strain Py2.

In yet another preferred embodiment of the invention, the acetone-specific enzyme system contains acetone carboxylase isolated from a species of aerobic or anaerobic bacteria, more preferably from a species of *Xanthobacter, Rhodococcus*, or *Rhodobacter*.

In a preferred embodiment of the invention, an electrochemical biosensor for detecting acetone in a biological sample contains at least one acetone-specific enzyme system as generally described above, and a means for detecting a product resulting from a reaction between the at least one acetone-specific enzyme system and acetone in the biological sample. The acetone-specific enzyme system of the biosensor preferably comprises an enzyme selected from the group consisting of acetone carboxylase, secondary alcohol dehydrogenase, and acetone mono-oxygenase. In particular, the acetone-specific enzyme system may comprise at least one member selected from the group consisting of: 1) secondary alcohol dehydrogenase (S-ADH)-catalyzed reduction of acetone, with concomitant NAD(P)H consumption (oxidation); 2) acetone carboxylase reaction coupled to β-hydroxybutyrate dehydrogenase consumption of NAD(P)H; 3) acetone carboxylase reaction ATP hydrolysis coupled to NAD(P)H consumption; 4) S-ADH reaction NAD(P)$^+$ formation coupled to $H_2O_2$ formation; 5) acetone carboxylase reaction ATP hydrolysis coupled to $H_2O_2$ formation; 6) acetone carboxylase reaction coupled to β-hydroxybutyrate dehydrogenase NAD(P)$^+$ formation coupled to $H_2O_2$ formation; 7) acetone mono-oxygenase coupled to NAD(P)H oxidation; 8) acetone mono-oxygenase coupled to $H_2O_2$ formation; and 9) acetone monooxygenase-catalyzed NAD(P)$^+$ formation coupled to $H_2O_2$ formation.

In manufacturing a biosensor containing one or more acetone-specific enzyme systems, various enzymatic by-products and/or factors may be employed for the production of electrochemical signals for detecting enzymatic reactions. Organic cofactors, such as NAD, NADH, NADP, NADPH, FAD, FADH, FMN, FMNH, Coenzyme A, Coenzyme Q, TTQ (Tryptophan Tryptophylquinone) and PQQ (Pyrroloquinolinequinone), may be used. Electron transfer mediators may be employed to improve the kinetics of electron transfer, since organic cofactors sometimes easily foul a detector. Mediators useful in multi-electron transfers for reduced forms of cofactors may be included in the enzyme systems of the present invention. Similarly, inorganic cofactors or indicators may be employed for the production of electrochemical signals. Enzymatic reaction by-products, such as hydrogen peroxide or ammonium, and energetic molecules may also be used in the invention for coupling acetone metabolism to electrochemically measurable signals. Combinations of these cofactors and systems may be used.

In a preferred embodiment, the electrochemical biosensor according to the invention may further comprise a means of interfacing with an analytical device, such as a computer linked to the Internet.

In a preferred embodiment, the electrochemical biosensor according to the invention may be characterized in that two or more acetone-specific enzyme systems are present. In such a biosensor, the two or more acetone-specific enzyme systems may be disposed on separate electrodes, for example, electrodes grouped in sequentially arranged clusters along a sample detection pathway, forming an electrode array. In other words, electrodes intended for contact with a single acetone-containing sample may be grouped within a common sample pathway. Several groups having the same or different acetone-specific enzyme systems may be arranged sequentially along the pathway to enhance the sensitivity of acetone detection.

In an alternative preferred embodiment of the electrochemical biosensor of the invention, one or more of such separate electrodes in an array may be acetone-specific, while one or more additional separate electrodes in the array may be capable of detecting a non-acetone analyte. For example, in an ethanol detector in which acetone, if present, may be secondarily detected by an electrode designed for ethanol detection, the inclusion of a separate, acetone-specific electrode can provide a basis for correcting for such acetone interference. In another example, detection of both acetone and at least one further analyte may be desired in order to determine a useful ratio of analyte concentrations, which ratio may be desirable for detecting, for example, a medical condition or disease state, such as diabetes: in diabetes and other conditions, the ratio of acetone to, for example, β-hydroxybutyrate, may be useful to provide a more complete indication of the subject's metabolic state. The device of which the electrode array is a part, or an instrument to which the device can be interfaced, may electronically generate separate results for each electrode or separate results for each analyte. Alternatively, some type of combined result may be generated, for example, a sum, a difference, a ratio, etc. Electronics within the device, or electronics within a computer or other electronic instrument to which the electrode may be interfaced, can utilize the result(s) from the acetone electrode(s), for example: to calculate a ratio between the acetone and the other measured analyte(s) (for example, β-hydroxybutyrate); or to calculate a subtractive correction factor for interference of acetone in the results(s) obtained from the other array electrode(s) designed for detection of non-acetone analyte(s) (for example, ethanol) and then calculate a corrected reading therefor. One embodiment of such an array-based electronic (or electronically-coupled) device is an "electronic nose," which may be used for, for example: diagnosis of medical condition from breath analysis; diagnosis of medical conditions from gases or vapors emitted by infected fluid samples, for example, bacterially infected urine; detection of tank car and other industrial container gas leakage; quality control monitoring of fermentations and food processing systems by detecting emitted vapors; and monitoring of enclosed air space quality.

In a preferred embodiment of the invention, a method of detecting acetone in a biological sample involves introducing a biological sample containing acetone to a biosensor containing at least one acetone-specific enzyme system that utilizes acetone as a substrate, and detecting the interaction between the acetone and the acetone-specific enzyme system. The biological sample is preferably a vapor sample. Detection may be achieved via photometric, calorimetric, or electrochemical means. The method may further comprise facilitating electrochemical transduction of the at least one acetone-specific enzyme system and the acetone in the vapor sample via an electrochemically treated electrode, and electrochemically detecting a product resulting from a reaction of the at least one acetone-specific enzyme system with the acetone in the vapor sample.

The at least one enzyme system used in this method may comprise a member selected from the group consisting of acetone mono-oxygenase, acetone carboxylase and secondary alcohol dehydrogenase. Specifically, the enzyme system may include any one or more of: 1) secondary alcohol dehydrogenase (S-ADH)-catalyzed reduction of acetone, with concomitant NAD(P)H consumption (oxidation); 2) acetone carboxylase reaction product formation coupled to (for example, β-hydroxybutyrate dehydrogenase) consumption of NAD(P)H; 3) acetone carboxylase reaction ATP hydrolysis coupled to NAD(P)H consumption; 4) S-ADH reaction NAD(P)$^+$ formation coupled to $H_2O_2$ formation; 5) acetone carboxylase reaction ATP hydrolysis coupled to $H_2O_2$ formation; 6) acetone carboxylase reaction coupled to β-hydroxybutyrate dehydrogenase NAD(P)$^+$ formation coupled to $H_2O_2$ formation; 7) acetone mono-oxygenase coupled to NAD(P)H oxidation; 8) acetone mono-oxygenase coupled to $H_2O_2$ formation; and 9) acetone monooxygenase-catalyzed NAD(P)$^+$ formation coupled to $H_2O_2$ formation. The method preferably comprises electrochemically detecting acetone in the vapor sample at a level of 0.5 ppm to 10 ppm.

Several areas of subject care may be enhanced by using acetone-specific enzyme systems for monitoring acetone levels. In this regard, a home biosensor capable of enzyme-mediated acetone detection in biological samples would permit subjects, care-givers, and support groups to closely manage weight loss programs. Similarly, the inventive biosensor would enable subjects suffering from acetone-related conditions, such as diabetes, to monitor weight loss and/or the onset of ketoacidosis, as well as to non-invasively manage their diet and medications, thereby controlling acetone production. Another use for an acetone-specific enzyme system in a sensor is remote prescription medicine management through tagging of drug formulations with acetone or acetone-producing compounds.

In a preferred embodiment, an electrochemical biosensor device of the present invention uses enzymes specific for acetone as a substrate, wherein an acetone-enzyme system reaction is linked to a means of electrochemical detection. Use of such an acetone-specific monitoring device requires that the biosensor be able to detect low levels of acetone, particularly when the acetone to be monitored is contained in vapor samples. For example, electrochemical acetone biosensors according to the invention may be used to assist subjects in management of diabetes by measuring acetone levels in biological samples. Ketoacidosis readings and warnings may be obtained quickly by subjects at home, by incorporating into the device either means for generating (from the electrochemical response present during acetone detection) a qualitative or quantitative result, or means for interfacing the device with a computer, instrument, or apparatus containing such means for generating. One example of means for generating such a qualitative or quantitative result is electronic circuitry. Electronic circuitry may be incorporated into an acetone-detecting biosensor device according to the present invention, or by the biosensor may be designed to be capable of interfacing with a computer or other electronic instrument containing such circuitry. One such aspect uses a signal from the electrochemically detectable signal mediator that is amplified by recycling enzyme substrates to multiply electrochemical signal output. Such circuitry would be selected, for example, to be capable of generating and/or graphically/textually/symbolically displaying a qualitative (for example, "low," "moderate," "high," "safe," or "danger") or a quantitative (for example, "10 percent (%) over target," "6% below average," "12 ppm," or "40 mg/dL") result or results. The device or instrument may also contain a data storage means to record one or more test results. The device can also be interfaced with a computer network, such as the Internet, in order to transmit readings generate by the device to, for example, a clinic, laboratory, doctor's office, or support group, for example, as disclosed in WO 01/63277. Furthermore, obese subjects seeking to monitor weight loss may do so utilizing acetone-specific biosensors according to the invention in the privacy of their own homes, or with the remote help of medical professionals, caregivers, or support groups. This aspect of the invention is facilitated by the fact that ketosis is considered the best indicator of successful dieting, and acetone levels have been correlated to the component of pound weight loss due to fat.

Acetone-specific enzyme systems and sensors/electrodes of the present invention may be used to monitor ketogenic diet-utilizing subjects for seizure control, to detect gestational diabetes, to aid in Type I diabetes monitoring or Type II diabetes management, to monitor client progress in weight loss and eating disorders counseling and in high performance fitness training, and to assist in livestock management.

In addition to monitoring weight loss and managing acetone-related diseases, another medical application of an acetone-specific enzyme system according the invention is monitoring the availability of pharmaceutical compounds administered to a subject. The release into the bloodstream of therapeutics tagged with acetone or an acetone-producing compound could be tracked within a subject using a biosensor comprising an acetone-specific enzyme system as described herein. For example, an orally active therapeutic could be formulated with a tag comprising acetone, or acetoacetatic acid, or, for example, an acetoacetate salt, ester, or amide. Acetoacetate spontaneously decarboxylates to release acetone. Upon ingestion of the "tagged" therapeutic, the release of acetone from the formulation into the subject's bloodstream could be monitored by a biosensor comprising an acetone-specific enzyme system. Levels of acetone detected in the breath of a subject would then be detected by photometric or electrochemical means via oxidoreductase reactions linked to the acetone-specific enzyme system. Preferably, the dosed compound is administered parenterally, for example, by injection or implant placement, but other, non-parenteral routes of administration, for example, oral administration, are also suitable.

Thus, in another preferred embodiment of the invention, a method of using an acetone-specific enzyme system involves combining acetoacetate or a pharmaceutically acceptable salt, ester, amide, or other suitable derivative thereof, with a pharmaceutical compound, thereby tagging the compound; administering the tagged compound to a subject; and thereafter, monitoring release of the tagged compound into the subject's bloodstream via detection of acetone in a subject's biological sample by means of the inventive acetone-specific enzyme system. Specifically, release of the tagged compound is followed via measuring acetone results from acetoacetate breakdown, which acetone is detected in a biological sample by acetone interaction with the acetone-specific enzyme system of the invention. Multiple readings by the present enzyme system can thereby be used to monitor the rate of release of acetoacetate, and thus the rate of disintegration of the administered composition, which correlates with the rate of release of the pharmaceutical active ingredient(s) to the biological system (that is its bioavailability). Verification of drug delivery and of subject compliance with a drug treatment regimen may be performed in this way.

In another preferred embodiment, a method of measuring biodegradation of materials involves tagging a biocompatible implant or device by combining acetoacetate, or a pharmaceutically acceptable salt, ester or amide derivative thereof, with a biocompatible composition to form a biocompatible implant or device; placing the biocompatible implant or device in a biological system (for example, a cell culture, biotic environment, animal or human subject); and measuring release of acetone produced by degradation of acetoacetate released by erosion or degradation of the biocompatible implant or device. The biocompatible implant or device may be simply a sample of a material being tested for erosion or degradation in the biological system, or it may be an operative implant or device, for example, containing a pharmaceutical active ingredient whose controlled release from the implant or device is desired. Release of the acetoacetate can be detected upon its degradation to acetone, which interacts with an acetone-specific enzyme system of the present invention. The amount of acetone measured can be correlated with the amount of acetoacetate released of the implant, which in turn is indicative of decomposition of the biocompatible implant within the body. Multiple readings by the enzyme system of the present invention can thereby be used to monitor the rate of release of acetoacetate, and thus the rate of erosion or degradation of the material of which the implant or device is composed.

Biocompatible materials are those materials that do not impair normal biological functions. Thus, materials that are biocompatible are not, for example, biochemical inhibitors or toxic, mutagenic, or carcinogenic compounds, and do not cause, for example, immune response, allergic reaction, or blood clotting activity. The class of biocompatible materials includes both biodegradable and non-biodegradable materials. Biodegradable materials decompose in contact with a biological organism, either externally (for example, in the case of microbial biodegradation) or internally (for example, in the human body). Exemplary biocompatible, biodegradable polymers include, for example, proteins (for example, collagen), polysaccharides and derivatives (for example, chitosan), polydioxanone, and polyhydroxyalkanoates (PHAs, for example: PHA polymers such as polyglycolic acid, polylactic acid, polyhydroxybutyric acid, polyhydroxyvaleric acid; and PHA copolymers). Other exemplary biocompatible polymers include polyethyleneglycol, polycaprolactone, cellulosic polymers, polyvinylalcohol, polyhydroxyethylmethacrylate, and polyvinylpyrrolidone. Further biocompatible materials include hydroxyapatite, ceramics, glasses, various metals, and composite materials. New biocompatible materials are being continually developed, including those intended for short-term (for example, weeks), long-term (for example, months or years), and very-long-term (for example, years or decades) use in a biotic environment. New compositions intended for use as biocompatible materials must be tested to determine whether they are in fact biocompatible and to assess the half-life of the composition in order classify it, for example, as a short-term or long-term biodegradable material, or as a non-biodegradable material. The enzyme system of the present invention may be used to determine the half-life of such a material.

In addition, the acetone-specific enzyme systems and sensors/electrodes according to the present invention may be used in conjunction with detection means for other biological components in order to assist in identification of bacterial infection (for example, in conjunction with detection means for nitrous oxide, acetoin, and/or other biological compounds) or to assess oxidative stress or early cancer detection.

In a preferred embodiment of the invention, a kit for detecting acetone in a sample includes an acetone-specific enzyme system and a housing for the acetone-specific enzymes system, wherein the housing has a port for introducing a sample to the acetone-specific enzyme system. The acetone-specific enzyme system may be disposed on a disposable strip that fits into the housing, or the acetone-specific enzyme system may be fashioned into the housing to form a single disposable unit within the kit.

The present invention also provides a secondary alcohol dehydrogenase enzyme that is a protein obtained from *Xanthobacter autotrophicus* Py2 (ATCC® PTA-4779), having NAD+-dependent secondary alcohol dehydrogenase activity, having the ability to reduce acetone to isopropanol, having specific activity for ketones and secondary alcohols; having, for the oxidation of isopropanol to acetone, (1) a pH optimum of approximately 7.8, and having, for the oxidation of alcohols, (2) an average specific activity ratio for secondary-to-primary alcohols of at least 50:1 when tested at pH 7.8 under equivalent conditions individually with C3-C5 straight chain secondary alcohols and with C2-C5 straight chain primary alcohols; having, for the reduction of acetone to isopropanol, (3) a pH optimum of approximately 6.2, (4) an apparent $K_m$ of approximately 144±18 µM, (5) an apparent $V_{max}$ of approximately 43.4±1.2 µmol acetone reduced min$^{-1}$·mg$^{-1}$ protein, (6) an apparent k$_{cat}$ of approximately 30.4 sec$^{-1}$, (7) an apparent k$_{cat}$/K$_m$ of approximately 2.1×10$^5$, and (8) a K$_m$ for NADH of approximately 5.1±0.4 µM; and comprising at least one polypeptide molecule that has (a) a molecular mass of approximately 37.1 kDa as determined by mass spectrometry, (b) a pI of approximately 7.4 as determined by isofocusing electrophoresis, and (c) a tetradecameric N-terminal amino acid sequence of SEQ ID NO:7, and that is capable of being degraded to form fragments having the amino acid sequences of SEQ ID NO:8 to SEQ ID NO:19. Also, provided is the polypeptide thereof.

BRIEF DESCRIPTION OF THE DRAWINGS

FIG. 3 shows substrate specificity of S-ADH from *X. autotrophicus* strain Py2 in performing ketone reductions. S-ADH was determined to have protein N-terminus of SEQ ID NO: 7.

DETAILED DESCRIPTION OF PREFERRED EMBODIMENTS

Figure 1:
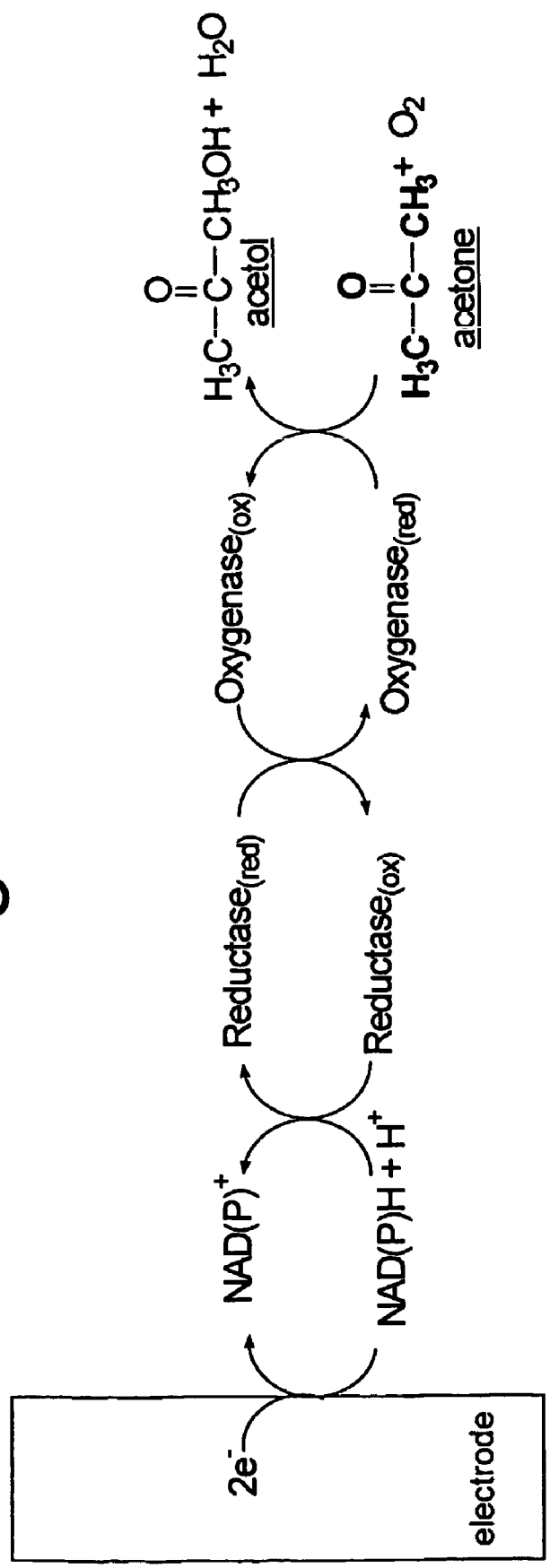
FIG. 1 graphically depicts electrochemical detection of acetone-dependent oxidation of NADH catalyzed by P-450 acetone monooxygenase isolated from *Mus musculus* and commercially available from PanVera Corporation, Madison, Wis.

Definitions $NAD(P)^+$ is used herein to mean "either or both of $NAD^+$ (nicotinamide adenine dinucleotide, oxidized form) and NADP (nicotinamide adenine dinucleotide phosphate, oxidized form)." NAD(P)H is used herein to mean "either or both of NADH (nicotinamide adenine dinucleotide, reduced form) and NADPH (nicotinamide adenine dinucleotide phosphate, reduced form)." Nicotinamide adenine dinucleotide is also called 3-carbamoyl-1-β-D-ribofuranosyl-pyridinium hydroxide 5'-ester with adenosine 5'-pyrophosphate, inner salt. Nicotinamide adenine dinucleotide phosphate is also called 3-carbamoyl-1-β-D-ribofuranosyl-pyridinium hydroxide 5'→35'-ester with adenosine 2'-(dihydrogenphosphate) 5'-(trihydrogen pyrophosphate), inner salt.

As used herein, "$A_{NNN}$" indicates "absorbance measured at NNN nanometers wavelength."

As used herein, "$\epsilon_{NNN}$" indicates "extinction coefficient measured at NNN nanometers wavelength."

"Enzyme" as used herein means "catalytically functional biomolecule;" thus any biomolecule that can perform a named catalytic function as its primary catalytic activity is considered an enzyme of that name, regardless of other considerations such as origin, native or engineered structure, size, etc.

"Platinized carbon," as used herein, indicates platinum-coated carbon, for example at least partially platinum-coated carbon nanoparticles.

"Photometric," as used herein, indicates any detection mode in which photons are utilized and includes, but is not limited to, colorimetric, spectrometric, spectrophotometric, luminescence-based, chemiluminescence-based, electrogenerated chemiluminescence-based, bioluminescence-based, and fluorescence-based methods.

In order to address certain difficulties associated with subject health maintenance, an enzyme-based biosensor has been developed, which enables the coupling of enzyme-mediated metabolism of acetone to electrochemically detectable signals produced via one or more of the signal mediators. Any acetone-specific enzyme capable of linkage to an electrochemically detectable co-factor or by-product may be suitable for the enzyme system of the invention. In a preferred embodiment, an electrochemical biosensor for detecting acetone in a biological sample contains at least one acetone-specific enzyme system, and a means for detecting a product resulting from a reaction between the at least one acetone-specific enzyme system and acetone in the biological sample. The detection means may be either electrochemical or non-electrochemical.

Acetone-Specific Enzymes

A number of enzymes, mainly from bacterial sources, have been described which specifically utilize acetone as a substrate. These enzymes have been obtained from and/or characterized in aerobic and anaerobic bacteria that are able to grow using acetone as a sole carbon and energy source.

Acetone may be formed in bacteria by the action of secondary alcohol dehydrogenase (S-ADH), an enzyme that operates in conjunction with one of two different acetone metabolic pathways: an $O_2$-dependent (oxygen utilizing) pathway in which the acetone is then oxidized to produce acetol, and a $CO_2$-dependent (carbon dioxide utilizing) pathway in which the acetone is then converted to acetoacetate. The acetone formation reaction catalyzed by S-ADH is freely reversible and normally requires a coenzyme that is typically either NAD(H) or NADP(H). The reduction of acetone to isopropanol by oxidation of NAD(P)H (the reverse, S-ADH-catalyzed reaction) involves redox chemistry by which acetone concentration can be monitored (for example, by means of electrochemical determination of NAD(P)H consumption). A variety of secondary alcohol dehydrogenases have been purified and characterized. Those best studied are S-ADHs obtained from hydrocarbon oxidizing (that is propane utilizing) bacteria, which employ $O_2$-dependent acetone metabolic pathways. S-ADH enzymes have also been isolated from or described in microorganisms not associated with hydrocarbon oxidation (that is propane degradative metabolism). These include methylotrophic bacteria and yeast, methanogenic Archaea, and fermentative anaerobes. Of these enzymes, S-ADH from *Thermoanaerobium brockii* is commercially available as a heat-treated crude preparation or in purified form (available from Sigma Chemical Co., St. Louis, Mo.). This enzyme is well characterized and is an NADPH-specific dehydrogenase;

In some propane-oxidizing bacteria, acetone is formed as an intermediate that is then understood to undergo hydroxylation in an $O_2$-dependent mono-oxygenase-catalyzed reaction to form acetol (hydroxyacetone). Acetol is then further oxidized to methylglyoxal catalyzed by an acetol dehydrogenase, or is involved in a carbon-carbon cleavage reaction producing C1 and C2 fragments. Acetone mono-oxygenase, which is a pyridine nucleotide-dependent enzyme, provides the necessary requirements for electrochemical detection in an acetone biosensor (as described above). Acetone metabolism via acetol as an intermediate has been identified in in vivo studies of acetone-utilizing bacteria. Also, P450 monooxygenases have been identified in mammals as using an identical mechanism (to oxidize acetone to acetol). An acetone mono-oxygenase suitable for use in an acetone-specific enzyme system is a cytochrome P450 acetone mono-oxygenase isolated from mice (*Mus musculus*). This monooxygenase has been reported as utilizing acetone as a substrate to produce acetol, and is commercially available from PanVera Corporation (Madison, Wis.). See F. Y. Bondoc et al., Acetone catabolism by cytochrome P450 2E1: Studies with CYP2E1-null mice. *Biochemical Pharmacology*, 58: 461-63 (1999). The enzyme responsible for this activity in bacteria has not yet been fully characterized. In addition, acetone mono-oxygenase can be coupled to $H_2O_2$ generation by including a galactose oxidase in the enzyme system; galactose oxidase oxidizes acetol to form $H_2O_2$ which can be detected either electrochemically or non-electrochemically.

Mammalian P450 cytochromes containing acetone mono-oxygenase activity and P450 reductase may be prepared from heptatic microsomes. P450 acetone mono-oxygenase catalyzes the following hydroxylation reaction:

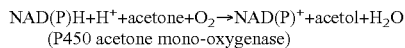
(P450 acetone mono-oxygenase)

P450 monooxygenases are typically comprised of two enzyme components including a pyridine nucleotide-dependent reductase and an active site-containing oxygenase component. NAD(P)H provides the necessary reductant for $O_2$ activation and incorporation of one oxygen atom into the aliphatic hydrocarbon substrate. With some P-450 monooxygenases, a third electron transfer component, cytochrome $b_5$, will stimulate activity. Acetone-dependent consumption of NAD(P)H by an acetone mono-oxygenase reaction could be monitored electrochemically as described below for secondary alcohol dehydrogenase-coupled and acetone carboxylase-coupled enzyme systems, as shown in FIG. 1. Alternatively, the reaction could be monitored by following $O_2$ consumption electrochemically, or monitored optically by measuring absorbance or fluorescence of NAD(P)H consumption as described below.

For other bacteria, including both aerobes and anaerobes, acetone metabolism is has been identified as proceeding by a $CO_2$-dependent carboxylation reaction producing acetoacetate. Acetone carboxylase, the enzyme that catalyzes this reaction, has recently been purified to homogeneity from two bacterial sources. Although acetone carboxylase does not catalyze a reaction that is readily detectable electrochemically, this enzyme has high specificity for acetone and, according to the present invention, can be coupled with other enzymes that catalyze redox reactions (for example dehydrogenases, oxidases). The feasibility of using coupling enzymes with acetone carboxylase for electrochemical detection had not been reported prior to this disclosure.

Suitable acetone carboxylases for use in an acetone-specific enzyme system include, but are not limited to, acetone carboxylase obtained: from *Xanthobacter autotrophicus* strain Py2 (referred to herein as *X. autotrophicus* Py2 or as *X. autotrophicus* st. Py2) (see Sluis, M. K. and Ensign, S. A., Purification and characterization of acetone carboxylase from Xanthobacter strain Py2, *PNAS USA*, 94: 8456-8462 (1997)); from *Rhodobacter capsulatus* B10 (see Sluis, M. K. et al., Biochemical, Molecular, and Genetic Analyses of the Acetone Carboxylases from *Xanthobacter autotrophicus* Strain Py2 and *Rhodobacter capsulatus* Strain B10, J. Bacteriol., 184(11):2969-77 (2002)); and from *Rhodococcus rhodochrous* B276 (see Clark, D. D. and Ensign, S. A., Evidence for an inducible nucleotide-dependent acetone carboxylase in *Rhodococcus rhodochrous* B276, J. Bact. 181(9): 2752-58 (1999)). *Xanthobacter autotrophicus* strain Py2 was deposited in the American Type Culture Collection (ATCC®) on Oct. 29, 2002 under ATCC® Accession No. PTA-4779. The ATCC® is located at 10801 University Boulevard, Manassas, Va. 20110-2209 U.S.A. and may be contacted at P.O. Box 1549, Manassas, Va. 20108 U.S.A. This deposit was made in accordance with the requirements of the Budapest Treaty. The amino acid sequences of the subunits of the *X. autotrophicus* Py2 acetone carboxylase are set forth in SEQ ID NOs: 1, 2, and 3; the nucleotide sequences of the genes encoding these subunits are available in GenBank (See accession number AY055852). The amino acid sequences of the *Rhodobacter capsulatus* B10 acetone carboxylase gene are set forth in SEQ ID NOs:4, 5, and 6; the nucleotide sequences of the genes encoding these subunits are available on the website of the "*Rhodobacter Capsulapedia*" sequencing project. Both the *X. autotrophicus* Py2 and the *R. capsulatus* B10 acetone carboxylase enzymes are alpha/beta/gamma ($\alpha/\beta/\gamma$) heterotrimers, sharing approximately an 80% overall sequence identity with each other, as well as exhibiting functional identity in catalyzing the same reaction with acetone.

Acetone-Specific Enzyme Systems

In a preferred embodiment of the invention, a breath acetone diagnostic device is provided that contains one or more acetone-specific enzyme systems. A preferred use of such a device is in monitoring ketone production in a mammal. In developing the invention, a number of oxidoreductase enzyme systems were investigated that, in the presence of acetone, oxidized pyridine nucleotides as cofactors or produced hydrogen peroxide as a co-product, allowing the reaction be detected electrochemically. These oxidoreductase enzyme systems include, for example: 1) the secondary alcohol dehydrogenase (S-ADH)-catalyzed reduction of acetone with concomitant NADPH consumption; 2) S-ADH-catalyzed reduction of acetone with concomitant NADH consumption; 3) acetone carboxylase reaction coupled to β-hydroxybutyrate dehydrogenase consumption of NADPH; 4) acetone carboxylase reaction coupled to β-hydroxybutyrate dehydrogenase consumption of NADH; 5) acetone carboxylase reaction ATP hydrolysis coupled to NADPH consumption; 6) acetone carboxylase reaction ATP hydrolysis coupled to NADH consumption; 7) S-ADH reaction $NADP^+$ formation coupled to $H_2O_2$ formation; 8) S-ADH reaction $NAD^+$ formation coupled to $H_2O_2$ formation; 9) acetone carboxylase reaction ATP hydrolysis coupled to $H_2O_2$ formation; 10) acetone carboxylase reaction coupled to β-hydroxybutyrate dehydrogenase $NADP^+$ formation coupled to $H_2O_2$ formation; 11) acetone carboxylase reaction coupled to β-hydroxybutyrate dehydrogenase $NAD^+$ formation coupled to $H_2O_2$ formation; 12) acetone mono-oxygenase coupled to NADPH oxidation; 13) acetone mono-oxygenase coupled to NADH oxidation; 14) acetone mono-oxygenase coupled to $H_2O_2$ formation; and 15) acetone monooxygenase-catalyzed $NAD(P)^+$ formation coupled to $H_2O_2$ formation.

In all of these enzyme systems, the pyridine nucleotide or hydrogen peroxide is detectable electrochemically, though other detection means known in the art can be utilized.

The use of enzymes as bioactive interfaces is well known in the art, and such interfaces are used in analytical methods of detecting electronic transduction of enzyme-substrate reactions. Direct electrical activation of enzymes such as redox enzymes permits stimulation of bioelectrocatalyzed oxidation or reduction of enzyme substrates. Rapid transfer of electrons between an electrode and a given redox enzyme results in current generation corresponding to the rate of turnover of the electron exchange between the substrate and biocatalyst. In other words, the transduced current of the system correlates with enzyme substrate concentration. Electrical contacting of redox proteins in a biosensor and the electrode support contained therein may be mediated by direct electron transfer with electrode surfaces. Redox enzymes lacking direct electrical communication with electrodes may achieve electrical contact by mediated electron transfer via active charge carriers. An electron relay may be oxidized or reduced at an electrode surface, and diffusion of the oxidized or reduced relay into enzyme results in short electron transfer distances with respect to the active redox center for mediated electron transfer and, thus, electrical activation of a biocatalyst.

Detection Means

The acetone-selective enzyme system, in acting upon the acetone substrate, generates an electrochemically or non-electrochemically detectable product or by-product directly, or the enzyme system will also include at least one further component. The further component may be: one or more additional enzyme(s) forming an enzymatic pathway utilizing the product or by-product of the initial enzymatic acetone reaction to thereby generate a photometrically or electrochemically detectable product or by-product; or at least one signal mediator; or both the additional enzyme(s) and the signal mediator(s). The signal mediator(s) may be selected from, for example: indicators, such as a pH-change indicators; electron transfer mediators; photometric mediators, and other components.

In an electrochemical embodiment of the invention, an acetone-specific redox enzyme or enzyme system is selected that utilizes an electrochemically detectable cofactor, such as NADH, or generates a by-product, such as $H_2O_2$, during the course of the enzymatic reaction. These enzyme systems can selectively detect acetone in biological samples, such as breath or biological fluids. However, detection of acetone is not limited to electrochemical means, and the enzyme system of this invention may be used in other types of devices, for example devices employing known UV, fluorescence, or other suitable methods of detecting acetone-specific enzyme-substrate interactions.

Non-Electrochemical Detection Means

Non-electrochemical detection involves, for example, any calorimetric or photometric detection mode known in the art (for example, any colorimetric, spectrometric, spectrophotometric, luminescence-based, chemiluminescence-based, or fluorescence-based detection method.)

A fluorescence detection device has the following minimum requirements: it must be light-tight to eliminate stray light from its surroundings, its fluors must be stored in the dark to prevent photobleaching (that is increase shelf life), and its optics must be at a 90° angle. A diode emitting the desired excitation wavelength can function as the light source, and a PMT can function as the detector. These need not be elaborate since both the excitation and emission $\lambda_{max}$ of the fluor are known, and these are the only wavelengths required. The same breath collection and acetone partitioning apparatus used in an enzyme electrochemical device can be used in a fluorescence device. A portable fluorescence detector for aflatoxin has been described in the literature (M A Carlson et al., An automated handheld biosensor for aflatoxin, *Biosens. Bioelectr.* 14:841 (2000)), so a precedent for a portable fluorescence detector exists.

Both direct and indirect fluorescence allows the detection of acetone from both breath and body fluids. The acetone-specific enzymes and their cofactors can be immobilized on a disposable strip using conventional entrapment techniques. When acetone diffuses through the immobilization medium to the enzyme, the acetone will be chemically altered. Unfortunately acetone itself is not fluorescent and cannot be derivatized inside the detection device. Thus another reagent needs to be derivatized with a fluorophore or a fluor needs to be added to the system to monitor the reaction. For the secondary alcohol dehydrogenase system, NADH consumption can be monitored, while the acetone carboxylase system can use ATP-analogs. As the NADH or ATP-analog is consumed, fluorescence intensity should decrease. Since the reaction with acetone is stoichiometric, fluorescence intensity is proportional to acetone concentration. The $H_2O_2$-generating systems can use $H_2O_2$ and an additional fluor. In these systems, $H_2O_2$ production causes an increase in fluorescence intensity that is proportional to acetone concentration.

We have verified that NADH in 100 mM phosphate buffer, pH 7.6, emits light directly at approximately 470 nm when excited with 342 nm light; these data agree with those reported in the literature (MA Carlson et al., 2000). In addition, NADH direct fluorescence has a 0.1-10 µM linear working range, is independent of pH from pH 6-13, decreases in intensity 1.6% per °C., and exhibits little altered fluorescence intensity in the presence of cations and enzymes below pH 10 (See P W Can & L D Bowers, Immobilized Enzymes in Analytical and Clinical Chemistry, *In Chemical Analysis. A Series of Monographs on Analytical Chemistry and Its Applications* (P J Elving & J D Winefordner, eds.; vol. 56, p. 122 (Wiley-Interscience, New York, 1980), and references contained therein). Several groups have described the use of direct NADH fluorescence to monitor enzymatic activity (A K Williams & J T Hupp, Sol-gel encapsulated alcohol dehydrogenase as a versatile, environmentally stabilized sensor for alcohols and aldehydes, *J. Am. Chem. Soc.* 1998, 120: 4366; and VP lordanov et al., Silicon thin-film UV filter for NADH fluorescence analysis, *Sens. Actual. A,* 2002, 97-98: 161).

Indirect fluorescence of NADH can be detected using the dye rhodamine 123. Non-radiative energy transfer (also called fluorescence resonance energy transfer, FRET) occurs between the excited states of NADH and rhodamine 123. FRET is a well-known technique for determining the proximity of two species, i.e. FRET is utilized as a "molecular yardstick" both in vitro and in vivo. In this context of an acetone-specific enzyme system, a donor fluorophore, e.g., NADH, transfers its excited state energies to the acceptor fluorophore, rhodamine 123. (R P Haugland, *Handbook of Fluorescent Probes and Research Products,* 2002 ($9^{th}$ ed.; Molecular Probes, Inc.; Eugene, Oreg.); K Van Dyke et al., eds. *Luminescence Biotechnology. Instruments and Applications,* 2002 (CRC Press; Boca Raton, Fla.) and references contained therein). The NADH-rhodamine 123 FRET method has been successfully employed in other enzymatic assays (M H Gschwend et al., Optical detection of mitochondria) NADH content in intact human myotubes, *Cell. Mol. Biol.* 47:OL95 (2001); H. Schneckenberger et al., Time-gated microscopic imaging and spectroscopy in medical diagnosis and photobiology, *Opt. Eng.* 33:2600 (1994)). Bioluminescence resonance energy transfer, or BRET, may also be used in conjunction with an acetone-specific enzyme system according to the present invention. In BRET, the donor fluorophore is replaced by a luciferase. Bioluminescence from luciferase in the presence of a substrate excites the acceptor fluorophore. BRET has also been applied in vitro and in vivo (K Van Dyke et al., 2002).

ATP can be derivatized with a fluorophore for indirect fluorescence. Several commercially available dyes include BODIPY ATP and trinitrophenyl ATP (Haugland, 2002). These analogs change their fluorescence intensity or become fluorescent when bound to an enzyme's ATP binding site.

Indirect fluorescence detection of $H_2O_2$ has also been reported (Carr & Bowers, 1980). These methods utilize dyes that reduce the peroxide to $H_2O$ and are themselves oxidized. Homovanillic acid (4-hydroxy-3-phenylacetic acid) and p-hydroxyphenylacetic acid are among the most commonly used in clinical chemistry (Can and Bowers, 1980). A commercially available kit uses the dye Amplex Red for fluorescence detection of $H_2O_2$ (Haugland, 2002).

Any fluorescent dyes and fluorescence-detectable enzyme substrate or cofactor analogs can be used in a fluorescence device to detect acetone in breath or bodily fluids.

Chemiluminescence (CL) and electrogenerated chemiluminescence (ECL) (collectively referred to herein as "(E) CL") are widely used in medical diagnostics and analytical chemistry (C Dodeigne et al., Chemiluminescence as a diagnostic tool: A review, *Talanta* 2000, 51:415; K A Fähnrich et al., Recent applications of electrogenerated chemiluminescence in chemical analysis, *Talanta* 2001, 54:531). Enzyme-based (E)CL systems are sensitive and specific, and many CL systems are used with enzyme cycling to detect $H_2O_2$ (Dodeigne et al., 2000). (E)CL can detect picomolar (pM; $10^{-12}$M) concentrations of analyte over a wide linear range (Dodeigne et al., 2000; Fähnrich et al., 2001). An (E)CL device can be constructed in accordance with the following principles. Since the reaction itself emits light, an (E)CL device does not need a light source. A photomultiplier tube (PMT) can function as the detector; (E)CL is visible to the unaided, dark-adapted eye. A battery can be the power source for ECL. ECL requires electrodes and a source of applied potential. Like a fluorescence detection device, (E)CL devices need to be light tight and their reagents need to be protected from light until use. Also like fluorescence, (E)CL requires derivatized reagents or additional enzymes and reagents to detect acetone. (E)CL devices can be used with disposable strips (B D Leca et al., Screen-printed electrodes as disposable or reusable optical devices for luminol electrochemiluminescence, *Sens. Actuat. B*. 2001, 74: 190) and can be miniaturized (Y Lv et al., Chemiluminescence biosensor chip based on a microreactor using carrier airflow for determination of uric acid in human serum, *Analyst* 2002, 127: 1176).

An optical electrode (or optrode) can be fabricated using an acetone-specific enzyme system according to the present invention. For example, an optrode such as that used in a glucose optrode that uses ECL, may be employed (see C H Wang et al., Co-immobilization of polymeric luminol, iron (II) tris(5-aminophenanthroline) and glucose oxidase at an electrode surface, and its application as a glucose optrode, *Analyst* 2002, 127:1507)).

The most common CL systems involve the detection of $H_2O_2$ or another reactive oxygen species (Carr & Bowers, 1980; Haugland, 2002; Dodeigne et al., 2000; K Van Dyke et al., 2002) and references contained therein). The classic system is luminol-peroxidase. In basic solution, $H_2O_2$ oxidizes luminol to an excited amino-phthalate ion; the excited aminophthalate ion emits a 425-nm photon to return to its ground state. When used in medical diagnostics, this reaction is catalyzed with horseradish peroxidase (HRP) (Carr & Bowers, 1980; Dodeigne et al., 2000). Thus any enzyme system that produces $H_2O_2$ or requires a cofactor that can react with additional reagents to form $H_2O_2$ can be used in a CL device. The $H_2O_2$-generating systems described herein can use luminol-HRP directly for acetone detection. These enzyme cycling schemes increase the light emission over time because the substrates are continuously recycled (Dodeigne et al., 2000). While luminol itself is frequently used in CL, its improved analogs can also be used in a CL-based detector according to the present invention, in place of luminol, in order to increase the sensitivity. Examples of such analogs are those described in Carr & Bowers, 1980; and Dodeigne et al., 2000.

NADH detection using CL is a common technique (Dodeigne et al., 2000). For example, in the presence of 1-methoxy-5-methylphenazinium methylsulfate, NADH reduces $O_2$ to $H_2O_2$ which generates light using the luminol-peroxidase system (Dodeigne et al., 2000). For an acetone monitor, the $O_2$ in ambient air is sufficient to detect acetone using this system. NADH also reacts with oxidized methylene blue to form $H_2O_2$ that reacts with luminol (Carr and Bowers, 1980). NADH can also act as a CL quencher. The fluorescence intensity of the substrate ALPDO is decreased in the presence of NADH and HRP (Van Dyke et al., 2002). NADH also can be used with $Ru(bpy)_3^{2+}$ for ECL (E S Jin et al., An electrogenerated chemiluminescence imaging fiber electrode chemical sensor for NADH, *Electroanal.* 2001, 13(15):1287). Rhodamine B isothiocyanate can also be used for ECL detection of $H_2O_2$ (Fähnrich et al., 2001). ECL also offers another advantage in that, by use of a properly poised electrode, the electroactive species can be regenerated at the electrode surface. Regeneration both conserves reagents and allows durable and/or "reagentless" sensors. All these systems can be used in a (E)CL device interfaced to an acetone-specific enzyme system according to the present invention.

CL is widely used to quantitate ATP simply and sensitively (Carr & Bowers, 1980). The enzyme luciferase catalyzes the reaction of ATP and luciferin to produce excited-state oxyluciferin, which returns to its ground state with the emission of a 562-nm photon (Carr & Bowers, 1980; Haugland, 2002). The quantum yield for this reaction is very high; $10^{-14}$ mol ATP can be detected. A kit for this reaction is commercially available (Haugland, 2002). Because luciferase is the enzyme that causes fireflies to "glow," this reaction is referred to as bioluminescence. Both native and recombinant luciferase are commercially available, and several groups have reported using bioluminescence ATP assays to quantify biological analytes (P Willemsen et al., Use of specific bioluminescence cell lines for the detection of steroid hormone [ant]agonists in meat producing animals, *Anal. Chim. Acta* 2002, 473:119; S J Dexter et al., Development of a bioluminescent ATP assay to quantify mammalian and bacterial cell number from a mixed population, *Biomat*. 2003, 24:nb27). In addition to the luminol-HRP system, $H_2O_2$ can also be detected using peroxyoxalic acid derivatives (Dodeigne et al., 2000). $H_2O_2$ can also be detected with CL non-enzymatically with ferricyanide as the catalyst (Dodeigne et al., 2000). In these (E)CL systems, the acetone-specific enzymes described herein either produce $H_2O_2$ or require cofactors that can be utilized to form $H_2O_2$.

Optical biosensors use photometric detection (that is, absorbance, fluorescence) of substrates consumed or products formed by the reaction catalyzed by the enzyme system incorporated into the sensor. The acetone-specific enzyme reactions described may be monitored by several photometric methods-namely by measuring NAD(P)H absorbance at 340 nm for the pyridine nucleotide-dependent enzymes or absorbance of the quinoneimine dye for the $H_2O_2$ forming enzyme systems. For the later, addition of a peroxidase allows detection of $H_2O_2$ by catalyzing the reduction of $H_2O_2$ with concomitant oxidation of a dye compound that upon oxidation absorbs at a specified wavelength. Peroxidase enzymes (for example, commercially available horseradish peroxidase) typically have broad substrate specificities so several different electron donor compounds may be used. NAD(P)H consumption may also be measured by fluorescence detection (excitation at 350 nm and emission at 450 nm).

Calorimetry may be employed as a detection means in an acetone-specific sensor according to the present invention. Chemical reactions are typically either exo- or endothermic; that is, they release or absorb heat as they occur. Calorimeters detect and measure this heat by measuring a change in the temperature of the reaction medium (K Ramanathan & B Danielsson, Principles and applications of thermal biosensors, Biosens Bioelectr. 16:417 (2001); B Danielsson, Enzyme Thermistor Devices. In *Biosensor Principles and Applications*. Vol. 15, pp. 83-105 (L J Blum & P R Coulet, eds.; Bioprocess Technology Series, volume 15; Marcel Dekker, Inc: New York, 1991, pp. 83-105, and references contained therein). Thus, the action of an acetone-specific enzyme or enzyme system may be monitored calorimetrically. Calorimeters have been designed that are sensitive enough to detect protein conformational changes, and calorimetry has been used to study many enzymatic reactions in detail (M. J. Todd & J Gomez, Enzyme kinetics determined using calorimetry: a general assay for enzyme activity? Anal. Biochem. 2001, 296:179 (2001)).

The major advantage of calorimetry is the lack of derivatization required for analysis (Danielsson, 1991). Since most reactions involve heat exchange, and this heat is detected, no chromophores, fluorophores, luminophores, "mediators," or other modifications of the analyte are required. Reagents and analytes can be used "as is." This allows the analysis of both reactions that lack a chromophore or fluorophore and/or would be difficult or impossible to derivatize or couple to the generation of an electroactive species.

Miniaturized or chip-based thermosensors have been reported in the literature (Ramanathan & Danielsson, 200:1; B Xie & B Danielsson, Development of a thermal microbiosensor fabricated on a silicon chip. Sens. Actuat. B 6:127 (1992); P Bataillard et al., An integrated silicon thermopile as biosensor for the thermal monitoring of glucose, urea, and penicillin. Biosen. Bioelect. 8:89 (1993)). These devices range from radically arranged thermopiles on freestanding membranes to groups of thermopiles constructed on silicon/glass microchannels. These devices have been used to detect specific, single enzymatic reactions (Danielsson, 1991; Xie & Danielsson, 1992; Bataillard et al., 1993). Moreover, two groups have reported thermosensors for glucose (B Xie et al., Fast determination of whole blood glucose with a calorimetric micro-biosensor, Sens. Actuat. B 15-16:141 (1993); M J Muehlbauer et al., Model for a thermoelectric enzyme glucose sensor, Anal. Chem. 61:77 (1989); B C Towe & E J Guilbeau, Designing Medical Devices, 1998. Preliminary experiments using a conventional calorimeter indicate that the secondary alcohol dehydrogenase-acetone reaction is exothermic (data not shown).

For the acetone monitor described herein, the acetone-specific enzymes and their cofactors can be immobilized on a thermopile via conventional entrapment methods. The enzymes and reagents associated with the coupled electrochemical detection, electrochemical mediators, and "photonic" mediators (luminophores) are unnecessary for calorimetry. The reaction involving acetone can be monitored directly without modification or derivatization. When acetone in the breath or fluid sample diffuses through the immobilization medium and encounters the enzyme, the acetone will be chemically altered. This reaction will generate or absorb heat, causing a temperature change. Comparison of this temperature with that of a reference thermopile will quantify this heat; the measurement is differential. The quantity of heat released or absorbed is proportional to the analyte concentration.

For breath collection, partitioning the acetone from the gas phase to the liquid phase, that is, condensation, is exothermic. The reference or dual thermopile can compensate for this heat. Thus an enzyme calorimetric acetone monitor can use the same breath collection apparatus as an enzyme electrochemical acetone monitor except for the addition of the dual thermopile.

The entire enzyme calorimetric device needs to be sufficiently insulated to prevent heat exchange with its surroundings. Except for electrochemical detection, other aspects of the device, such as enzyme stability, specificity, device portability, etc., described in this document are the same as those for an enzyme electrochemical device.

Thus, useful methods for achieving signal transduction in biosensors according to the present invention include not only electrochemical (amperometric or potentiometric), but also optical or photometric (including colorimetry, fluorescence-based techniques, or chemiluminescence-based techniques), and calorimetric means, all of which are useful in application to acetone biosensor signal transduction.

Therefore, although electrochemical detection means are described and exemplified in detail herein, the enzyme systems of the invention are not limited to use in biosensors employing electrochemical detecting strategies. Other detection strategies may be suitably integrated into a biosensor specific for acetone in biological samples. Photometric assays, such as assays in which changes in the amount of light absorbed in a reaction solution over time may be used. Likewise, assays in which changes in fluorescence or changes in sample turbidity may be employed for detecting acetone-specific enzyme-substrate interactions. Such photometric assays are discussed hereinbelow. Redox potentials of $H_2O_2$ and colorimetric/photometric detection of coenzymes is discussed by Bergmeyer. Photometric assays for enzymatic activity are generally described by John in "Photometric Assays". An NADH-consumption measuring electrode is disclosed by Hart et al. in a 1999 article published in Electroanalysis. Vanysek discloses redox potentials in general, and oxidation-reduction potentials of various compounds suitable for use in biochemical applications are disclosed by Voet & Voet.

An enzyme system employing S-ADH coupled to alanine dehydrogenase was successfully monitored spectrophotometrically for NADH formation. In addition, since the reaction also generates ammonium ion, an optical sensor for $NH_4^+$ can be employed as the detection means for such an enzyme system. One such optical means is described by T D Rhines and M A Arnold, Fiber-optic biosensor for urea based on sensing of ammonia gas, *Anal Chim. Acta*, 1989, 227:387; several enzyme-based amperometric $NH_4^+$ sensors are commercially available. For acetone detection, ammonia production can be coupled to the secondary alcohol dehydrogenase system as above; ammonia concentration would then be proportional to acetone concentration. Another enzyme scheme to couple acetone to ammonia production is the following:

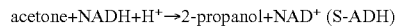
acetone+NADH+H$^+$→2-propanol+NAD$^+$ (S-ADH)

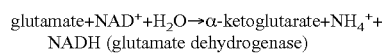
glutamate+NAD$^+$+H$_2$O→α-ketoglutarate+NH$_4^+$+ NADH (glutamate dehydrogenase)

This second scheme can be used either optically or amperometrically to detect acetone. Additionally, the NADH is recycled. Likewise, an enzyme system in which acetone carboxylase is coupled to glutamate dehydrogenase, generates $NH_4^+$ and so can be detected optically or amperometrically and correlated with acetone concentration.

Electrochemical Detection Means

Amperometric biosensors work by generating current between two electrodes by enzymatically producing or consuming a redox-active compound. Several examples of amperometric acetone biosensor schemes have been described in which NAD(P)H or $H_2O_2$ are consumed or generated enzymatically in response to the presence of acetone. In examples where the transducer is $H_2O_2$, an alternative means to monitor the reaction amperometrically could be to employ a Clark-type oxygen electrode and measure a decrease in $O_2$ concentration. For example, in the case for the secondary alcohol dehydrogenase (SADH) coupled to $H_2O_2$ formation, the enzyme system catalyzes the following:

acetone+NADH+H$^+$→2-propanol+NAD$^+$ (S-ADH)

lactate+NAD$^+$→pyruvate+NADH+H$^+$ (lactate dehydrogenase)

pyruvate+Pi+$O_2$→acetylphosphate+$CO_2$+$H_2O_2$ (pyruvate oxidase)

Oxygen is then reduced/consumed at the cathode generating a concentration gradient between the electrode and the bulk solution. The rate of electrochemical reaction is dependent on the oxygen concentration in solution.

Potentiometric biosensors employ ion-selective electrodes in which the release or consumption of ions during an enzyme reaction is measured (for example, H$^+$, CN$^-$, NH$_4^+$) (1, 2, 3). For example, a potentiometric biosensor for measuring acetone concentration can be utilized where NH$_4^+$ formation is coupled to the reaction catalyzed by S-ADH and alanine dehydrogenase as follows:

acetone+NADH+H$^+$→2-propanol+NAD$^+$ (S-ADH)

alanine+NAD$^+$→pyruvate+NADH+H$^+$+NH$_4^+$ (alanine dehydrogenase)

(Photometric data for this system has already been obtained to verify its utility for acetone-specific signal transduction: see the discussion under the "Results" section, below).

A very similar system can be utilized with acetone carboxylase ("β-OH-butyrate dehydr." being "beta-hydroxybutyrate dehydrogenase"):

acetone+ATP+$CO_2$→acetoacetate+AMP+2Pi (acetone carboxylase)

acetoacetate+NADH+H$^+$→β-hydroxybutyrate+NAD$^+$ (β-OH-butyrate dehydr.)

alanine+NAD$^+$→pyruvate+NADH+H$^+$+NH$_4^+$ (alanine dehydrogenase)

Another type of electrochemical biosensor that may be employed is a light-addressable potentiometric sensor. In one embodiment of such a device, the acetone-specific enzyme system(s) may be applied to (e.g., immobilized to the surface of) a potentiometric sensing means such as that described, for sensing glucose, in A Seki et al., Biosensors based on light-addressable potentiometric sensors for urea, penicillin, and glucose, *Anal. Chim. Acta* 373(1):9-13 (2 Nov. 1998).

In designing an acetone-specific biosensor according to the invention, various enzymatic by-products and/or factors may be employed for the production of electrochemical signals. One group includes organic cofactors, such as NAD, NADH, NADP, NADPH, FAD, FADH, FMN, FMNH, Coenzyme A, Coenzyme Q, TTQ (Tryptophan Tryptophylquinone) and PQQ (Pyrroloquinolinequinone). For example, a PQQ-dependent dehydrogenase may oxidize isopropanol. Electrons from this reaction may be transferred through PQQ, which is reduced, and can be oxidized at the electrode or with an intervening enzyme. Other vitamins may also be used.

Enzymatic reaction by-products useful in the invention include hydrogen peroxide and ammonium.

Energetic molecules may also be used in the invention for coupling acetone metabolism to electrochemically measurable signals, including: ATP, ADP, AMP, GTP, GDP and GMP. Neither these molecules nor phosphate can be detected directly, but can be detected through coupling to a redox-by-product-producing enzyme system.

These by-products, cofactors, and energetic molecules can also be detected by non-electrochemical means as described above.

Signal Mediators

Electron transfer mediators are redox-reversible species that may be used to transfer electrons between (that is to or from) the electrically potentiated surface of an electrode and an organic species (such as a co-factor) involved in an enzymatically catalyzed reaction. Examples of electron transfer mediators include: ferrocene and derivatives, ferricyanide, hydroquinone, benzoquinone and derivatives, 2,6-dichloroindophenol, methylene blue, phenylenediamine and derivatives, phenoxazine and derivatives (for example, Meldola's blue, that is 8-dimethylamino-2,3-benzophenoxazine), and phenazine alkosulfates (for example, phenazine methosulfate, phenazine ethosulfate). In a given embodiment, one or more than one species of electron transfer mediator may be used.

Electron transfer mediators can be used to improve the kinetics of electron transfer in a given enzyme-coupled electrode system, since organic cofactors may easily impair detector functions. This impairment is caused by the creation of free radicals via singly transferring multiple electrons between organic species and the electrically potentiated surface of the electrode. These free radicals then can exhibit dimer and/or polymer formation at the electrically potentiated surface, which fouls the surface of the electrode, thereby inhibiting efficient electron transfer. Electron transfer mediators can be employed to avoid this fouling of electrodes. Electron transfer mediators may also be used in situations where a shift in electrode voltage is desired, for example, where the preferred voltage for use in the reaction system without such a mediator happens to be a potential at which too much electrical interference ("noise") occurs. An electron transfer mediator may be added in order to permit a shift in the applied voltage to a different voltage region in which less noise occurs. Examples of diffusional electron-transfer mediators applicable to immobilized enzymes such as glucose oxidase, horseradish peroxidase, and the like, are set forth in Table 5 of Willner and Katz.

Preferred mediators useful in multi-electron transfers for reduced forms of, for example, NADH, NADPH, FADH, FMNH, Co-Q, PQQ, include, for example: ferrocene and derivatives, ferricyanide, hydroquinone, benzoquinone and derivatives, 2,6-dichloroindophenol, methylene blue, phenylenediamine and derivatives, phenoxazine and derivatives (for example, Meldola's blue, that is 8-dimethylamino-2,3-benzophenoxazine), and phenazine alkosulfates (for example, phenazine methosulfate, phenazine ethosulfate).

A second group of mediator factors that may be employed for the production of electrochemical signals include inorganic cofactors such as Pt, Os, V, Mn, Fe, Co, Ni, Cu, Mo, and W (see Holm et al., Aspects of Metal Sites in Biology, Chem. Rev. 1996. 96, p. 2239-2314). Some useful enzymes contain a heme center, and thus iron (for example, cytochrome P450 monooxygenase). Also useful is amine oxidase, which contains Cu.

In an alternative embodiment, a "photometric mediator" may be added to the enzyme system in order to react with a product or by-product of the enzymatic reaction(s) and thereby generate a derivative that can be, for example, photochemically, colorimetrically, fluorometrically, or (UV or IR) spectrometrically detected. Thus, the addition of such a "photometric mediator" may be characterized as permitting the conversion of a result of the enzymatic reaction, that is a product or by-product, into a photometric signal. For example, in the case of enzymatically catalyzed redox reactions, a chromogenic redox indicator such as, for example, a tetrazolium salt, may be used as the photometric mediator. Many such chromogenic redox indicators are known in the art. Examples of tetrazolium salts include, but are not limited to: 3-(4,5-dimethylthiazol-2-yl)-2,5-diphenyl-2H-tetrazolium bromide (MTT bromide); (3-(4,5-dimethylthiazol-2-yl)-5-(3-carboxymethoxyphenyl)-2-(4-sulfophenyl)-2H-tetrazolium, inner salt (MTS; available from Promega Corp., Madison, Wis.); and (5-cyano-2,3-ditolyl tetrazolium chloride) (CTC). Such photometric mediators can be used, for example, to convert the redox "signal" of an electron transfer mediator into a photometrically detectable signal.

The enzymes and other components of the enzyme system may be immobilized in a gel layer disposed upon the electrode surface. Any of the various gels known in the art as useful for immobilization of biologics in the presence of an electrode may be used. For example, a method such as is described in PCT/US02/16140 (filed May 21, 2002) may be used to immobilize the biologic components of an acetone-specific enzyme system in a polyurethane hydrogel disposed upon an electrode.

Enzyme Arrays and Multi-Enzyme Systems

In addition to monitoring acetone in a sample per se, acetone-specific enzyme systems may be useful in biosensors having more than one enzyme system for detecting multiple substrates in a given biological sample. For example, an electrode linked to an acetone-specific enzyme system may enable subtraction of an acetone signal from an ethanol detector. Such a set up could be configured in an array, wherein at least two different detection modes or at least two different detectors would be operative for detecting ethanol and acetone. Such an array would be useful to correct for acetone interference in ethanol breathalyzer analyses.

Fluorescence detection can also be accomplished using arrays. Fluorescence sensor arrays have been described in the literature. They have been used for such complex samples as wine aromas, perfume, and genes. Fluorescence sensor arrays employ fluorescent or chromogenic dyes or substrates that covalently attached to polystyrene beads in wells on the distal face of an optical fiber (D. R. Walt, Imaging optical sensor arrays. Curr. Opin. Chem. Biol. 6:689 (2002)). A high-density optical array can contain several types of dyes or substrates for different analytes. The array is exposed to each possible component individually, then to the sample. Pattern recognition is employed to deduce the composition of the sample. In the case of breath or bodily fluid components, the acetone-specific enzymes, cofactors, and chromogenic or fluorogenic dyes can be covalently attached to a portion of beads, while enzymes specific for other analytes, such as ethanol, can be attached to other beads. Each bead will "light up" upon exposure to its target analyte.

An enzyme-based fluorescence or chromogenic array has never been applied to the detection of acetone.

Uses for an Acetone-Specific Enzymatic Biosensor

Breath acetone monitoring is a useful tool for monitoring effectiveness and compliance of subjects on weight loss diets. Ketosis can be manipulated by exercise and dieting choices, even between two diets with equal energy balance. The response time for reflecting diet and exercise choices in breath acetone levels is in the order of 2-3 hours, and was a better indicator of fat loss than urine ketone analysis.

A home acetone diagnostic biosensor would be useful in aiding subject management of Type 1 and Type 2 diabetes. Such biosensors would enable subjects to monitor weight loss, to detect signs of the onset of ketoacidosis, and to control sugar intake with respect to insulin availability, especially in Type 1 diabetics. Indicators suggest that weight loss success would be improved if subjects could share daily acetone measurements with health care professionals and peers via the Internet and weekly support group meetings. Use of the inventive acetone-specific detection system is not limited to management of obesity and diabetes. It is contemplated that the acetone-specific biosensors described herein would be useful for managing any disease in which acetone production is an indicator of pathology.

In addition, the acetone-specific enzyme system may prove to be a highly effective means of monitoring subject compliance with prescribed therapeutic regimes via drug tagging with acetoacetate or a derivative thereof. The degradation of acetoacetate to acetone could be measured via a biosensor containing the inventive acetone-specific enzyme system, thereby improving the ability of health care professionals to track the dosing and bioavailability of the corresponding tagged drug.

EXAMPLES

Acetone-specific enzyme systems and acetone sensors utilizing these systems have been developed. Enzyme identification and/or purification, enzyme characterization and selection, enzyme-plus-cofactor systems, multiple-enzyme-plus cofactor systems, coupled enzyme systems providing linear (stoichiometric) acetone detection, coupled enzyme systems providing amplified (for example, exponential) acetone detection, enzyme and enzyme system stability testing, acetone vapor-to-liquid partitioning studies, and enzyme-mediated acetone sensor devices (both electrochemical and non-electrochemical devices) that utilize such systems sensors are disclosed below in particular exemplified embodiments. These examples are provided for exemplification and are not intended to limit the invention. Particular embodiments employing acetone-specific enzyme systems in enzyme-based electrochemical and non-electrochemical sensors is described below.

Materials & Methods

Materials. Acetone carboxylase from *X. autotrophicus* strain Py2 and isopropanol-grown *X. autotrophicus* strain Py2 cell paste were obtained from Professor Scott A. Ensign at Utah State University, Logan, Utah. Acetone carboxylase from *Rhodobacter capsulatus* B10 (ATCC® 33303), acetone-grown *R. capsulatus* B10 cell paste, propane-grown *Mycobacterium vaccae* JOB5 (ATCC® 29678) cell-free extracts, and propane-grown *Rhodococcus rhodochrous* B276 (ATCC® 31338) cell paste were also obtained from Professor Ensign, and all of these bacterial strains are publicly available. Secondary alcohol dehydrogenase from *X. autotrophicus* strain Py2 and isopropanol-grown *X. autotrophicus* strain Py2 were isolated from cell paste; and exemplary, publicly available secondary alcohol dehydrogenases are described in Table 1. Pyruvate kinase (EC 2.7.1.40), myokinase (EC 2.7.4.3), pyruvate oxidase (EC 1.2.3.3), horseradish peroxidase (EC 1.11.1.7), lactate dehydrogenase (EC 1.1.1.28), malic enzyme (EC 1.1.1.40), alcohol dehydrogenase (EC 1.1.1.2), alanine dehydrogenase (EC 1.4.1.1), alcohol dehydrogenase (EC 1.1.1.1), alcohol oxidase (EC 1.1.3.13), and β-hydroxybutyrate dehydrogenase (EC 1.1.1.30) were purchased from Sigma (St. Louis, Mo.). All other chemicals and reagents used were analytical grade. All solutions were prepared in 18 MΩ water (Millipore).

TABLE 1

Information for Some Publicly Available S-ADH Enzymes

| Cofactor | Organism | Source | Reference(s) [& Comments] |
|---|---|---|---|
| NADPH | *Thermoanaerobium brockii* | Sigma Chem. Co.(catalog no. A8435) | RJ Lamed et al., Enzyme & Microb. Technol., 3: 144(1981); RJ Lamed & JG Zeikus, Biochem. J, 195(1): 183-90(Apr. 1, 1981); A Ben-Bassat et al., J Bact., 146(1): 192-99 (April 1981); [DNA sequence available in GenBank(Acc. No. X64841)] |
| NADH | *Mycobacterium vaccae* strain JOB5(Gram-positive) | ATCC 29678 | JP Coleman et al., J Gen. Microbiol., 131(11): 2901-07(November 1985); [Describes enzyme purification] |
| NADH | *Pseudomonas* sp. 6307 [CRL 75] (Gram-negative) | ATCC 21439 | CT Hou et al., Eur. J Biochem., 119(2): 359-64 (October 1981); [Describes enzyme purification] |
| NADH | *Xanthobacter autotrophicus* strain Py2 | ATCC PTA-4779 | [Enzyme purification and characterization described herein] |
| NADPH | *Thermoanaerobacter ethanolicus* 39E | ATCC 33223 | DS Burdette et al., Biochem. J 316(1): 115-22 (May 1996); [Describes enzyme purification, gene cloning & DNA sequencing] |
| NADH | *Candida utilis* (yeast) | DSM 70167; ATCC 26387 | H Schutte et al., Biochim. et Biophys. Acta, 716(3): 298-307(Jun. 16, 1982); [Describes screening for S-ADH activity in several yeast strains] |
| NADPH | "Anaerobic extremely thermophilic bacterium" | Biocatalysts Ltd.(Wales; catalog no. S300) | — |
| NADH | *Candida boidinii* (yeast) | Fluka (Milwaukee, WI; catalog no. 91031) | — |
| NADH | *Candida* sp. (yeast) | NovaBiotec Dr. Fechter GmbH(Berlin, Germany; catalog no. "Isopropanol dehydrogenase (E.C. 1.1.1.80)") | — |

Enrichment and isolation of acetone-, isopropanol-, and propane-utilizing microorganisms. Enrichment cultures were set up in 160 mL serum bottles that were crimp-sealed with butyl rubber stoppers. The bottles contained 10 mL mineral salts medium containing (in g/L): NaNH$_4$HPO$_4$ (1.74); NaH$_2$PO$_4$×H$_2$O (0.54); KCl (0.04); MgSO$_4$×7H$_2$O (0.2) and 1 mL/L of a trace element stock solution (stock solution in g/L): FeCl$_2$×4H$_2$O (5.4); MnCl$_2$×4H$_2$O (1.0); ZnSO$_4$×7H$_2$O (1.45); CuSO$_4$×5H$_2$O (0.25); concentrated HCl (13 mL/L); (NH$_4$)$_6$Mo$_7$O$_{24}$×4H$_2$O (0.1); H$_3$BO$_3$ (0.1); CoCl$_2$×6H$_2$O (0.19)). The pH of the medium was adjusted to pH 7.2. Enrichments for propane-utilizing microorganisms were inoculated with about 0.5 g of soil that had been purchased from a local supplier of top soils, or with about 0.5 g of non-sterilized potting soil or organic compost that had been purchased from a local supermarket.

Gaseous propane was added with a syringe to a 20% (v/v) concentration in the headspace of the serum bottle. Enrichments for acetone- and isopropanol-utilizing microorganisms were set up in a similar way except that substrates were added from a 1 M stock solution to a final concentration of 25 mM acetone, or 10 mM isopropanol. The enrichment cultures were incubated on a shaker at 28° C. For the isolation of single colonies, enrichment cultures were cultivated on mineral salts medium (as described above) containing 1.5% w/v agar (hereinafter "mineral salts agar").

In a different set-up, enrichment cultures were started for acetone-utilizing microorganisms that could grow in the presence of a CO$_2$-trap. 20 mL of mineral salts medium with trace elements (see above) was filled into 250 mL baffled Erlenmeyer flasks. The medium was inoculated with about 0.5 g of soil sample (see above). The Erlenmeyer flask was closed with a rubber stopper that had been modified to hold a glass bulb. The glass bulb contained about 0.5 mL of 50% (w/v) KOH. The KOH trapped the CO$_2$ from the Erlenmeyer flask headspace. These set-ups were designed to enrich for acetone-utilizing microorganisms with an acetone carboxylase-independent pathway. The enrichment cultures were incubated on a shaker at 28° C.

Enrichment cultures were transferred two to three times after turbidity indicated bacterial growth (usually after 3 to 5 days). To isolate single colonies, enrichment cultures were spread on mineral salts agar plates. For the isolation of propane-utilizers, the agar plates were placed in a 3.5 L anaerobic jar. Propane was added to the jar until a positive pressure of 0.3-0.5 bar was reached inside the jar. The jar was placed into an incubator at 28° C. For the isolation of acetone-utilizing microorganisms, the agar plates were placed into a 1.4 L desiccator. The desiccator contained two open glass vials with 3-4 mL neat acetone each. The desiccator was sealed with several layers of PARAFILM (a wax-based sealing film, from American National Can, Chicago, Ill.) before it was placed in an incubator at 28° C. For the isolation of acetone-utilizing microorganisms that would grow in the presence of a $CO_2$-trap, agar plates were placed in a desiccator as described above. In addition to a vial with acetone, a vial containing 50% KOH (about 4 mL) was placed into the desiccator. Alternatively, for the isolation of acetone- and isopropanol-utilizers, enrichment cultures were transferred to agar plates containing mineral salts medium plus acetone or isopropanol. Additional acetone or isopropanol was added onto a small foam plug that was placed inside the Petri dish. The Petri dish was sealed with several layers of parafilm to reduce evaporation of substrates during incubation.

Colonies were visible on the agar plates after 5-10 days. Isolates were transferred to fresh agar plates and incubated as described above. Isolated strains were also streaked onto nutrient agar to check for purity. After several transfers on agar plates, 31 strains were isolated that looked different as evaluated by colony morphology. Eight strains were isolated from propane enrichments (these were designated TDCC Prop 1-8), eight strains were isolated from isopropanol enrichments (these were designated TDCC IP-1-8) and fifteen strains were isolated from acetone enrichments (these were designated TDCC Ac 1-15). None of these were obtained from an acetone+KOH-trap enrichment.

Screening of isolates and culture collection strains for growth on acetone, propane, or isopropanol. Isolates and culture collection strains were screened for growth on acetone, propane, and isopropanol in 60 mL-serum vials containing 5 mL of medium plus 0.005% (w/v) yeast extract as described above. The medium was inoculated from a single colony. Isopropanol was added from a stock solution to a final concentration of 8 mM. Cultures that showed more turbidity with substrates compared to cultures without substrates (medium blanks) were considered hits. Hits were then screened for growth with acetone in the presence of a $CO_2$-trap as described above.

Cultivation of isolates/strains, harvesting, and preparation of cell-free extracts. Several isopropanol-utilizing strains were cultivated in larger batches for initial purification of secondary alcohol dehydrogenase and experiments with cell-free extracts. Strain *Rhodococcus rhodochrous* B276 (ATCC® 31338) (formerly *Nocardia corallina* B276) and strain TDCC (and two additional strains: data not shown) were cultivated in 2×500 mL batches of mineral salts medium (for composition see above) plus 0.005% yeast extract. Isopropanol (8 mM) was added initially as carbon and energy sources. Cultures were incubated on a shaker (200 rpm) at 30° C. Growth was followed by monitoring the optical density at 600 nm. More isopropanol was added at several time points when the growth rate decreased due to lack of substrate. A total of about 96 mM isopropanol was added to the cultures. At the end of the logarithmic growth phase, cells were precipitated by centrifugation (GSA rotor, 8,500 rpm, 20 min.) at 4° C. The cells were washed once in 50 mM Tris-HCl buffer, pH 7.5. The cell pellet was weighed and resuspended in a small volume of TRIS (2-amino-2hydroxymethyl-1,3-propane-diol) buffer (about 2 mL per g cells (wet weight)). Cells were frozen at −20° C. until further use. For the preparation of cell-free extracts, cells were thawed and broken by sonication (4×20 s, pulsed, 50% intensity). Cell debris and unbroken cells were precipitated by centrifugation for 5 min at 14,000 rpm (in an Eppendorf benchtop centrifuge, Model 5417C, Brinkmann, Instruments, Inc., Westbury, N.Y.). Alternatively, for larger preparations, the cell suspension was passed three times through a mini-French pressure cell at 20,000 psi (137, 895.2 kPa), and the lysate was clarified by centrifugation at 6,000×g for 40 min at 4° C.

Protein purifications. Acetone carboxylase from *X. autotrophicus* strain Py2 and acetone carboxylase from *R. capsulatus* were purified as described previously. Secondary alcohol dehydrogenase (S-ADH) from *X. autotrophicus* Py2 was purified via the following protocol. Cell-free extracts (380 mL) of isopropanol-grown *X. autotrophicus* Py2 (150 g) were prepared as described above, and applied to a 5×15 cm column of DEAE-Sepharose FAST FLOW (Diethylaminoethyl cross-linked agarose bead material; Catalog number 17-0709-10, Amersham Pharmacia Biotech, Piscataway, N.J.)) equilibrated in buffer A (25 mM MOPS (3-(N-morpholino)propanesulfonic acid), pH 7.6, 5% glycerol, 1 mM dithiothreitol) at a flow rate of 10 mL/min. After loading, the column was washed with 1000 mL/min buffer A and developed with a 2400 mL linear gradient of 90-290 mM KCl in buffer A. Fractions containing S-ADH activity were pooled and dialyzed against 2 L of 25 mM potassium phosphate (pH 6.2) containing 5% glycerol (buffer B) for 16 h at 4° C. The protein was then applied to a RED SEPHAROSE CL-6B (Procion Red HE-3B dye-linked, cross-linked-agarose bead material, affinity matrix for affinity chromatograph; Catalog number 17-0528-01, Amersham Pharmacia Biotech) column (1.5×10 cm) equilibrated in buffer B at a flow rate of 2 mL/min. After washing the column with 30 mL of buffer B, S-ADH was eluted with 20 mL of buffer A containing 10 mM $NAD^+$. Fractions containing S-ADH were then dialyzed against 2 L of buffer A for 16 h at 4° C., concentrated by ultrafiltration (using a YM30 ultrafiltration membrane; catalog no. 13722, from Millipore, Bedford, Mass.), and frozen in liquid nitrogen. Partially purified S-ADH from bacterial screen cultures was prepared as follows: cell-free extracts from 1 to 5 g of cell paste were prepared as described above and applied to a 5 mL HI TRAP Q column (quaternary, tetraethylammonium, cross-linked agarose bead material for use as an anion exchange matrix; catalog number 17-1153-01, Amersham Pharmacia Biotech) equilibrated in 100 mM MOPS, pH 7.6, containing 5% (v/v) glycerol (buffer C). The column was washed with 10 mL buffer C and developed with a 100 mL linear gradient of 0 to 100 mM NaCl in buffer C. Fractions containing S-ADH activity were pooled, concentrated to 0.5 mL using a 30 kDa MWCO ("molecular weight cut-off") centrifugal membrane (catalog number UFV4BTK25, Millipore), and stored at −80° C.

Example 1

Acetone Carboxylase Coupled to NADH Oxidation Spectrophotometric Assay

Assays were performed in 2 mL (1 cm path length) quartz cuvettes that had been modified by fusing a serum bottle-style quartz top (7×13 mm at mouth), allowing the cuvettes to be sealed with a red rubber serum stopper. The reaction mix contained ATP (10 mM), $MgCl_2$ (11 mM), potassium acetate (80 mM), MOPS (100 MM), $CO_2$ (50 mM (1 mol $CO_2$ (g) to 4 mol potassium bicarbonate to maintain pH)), and 20 to 40 µg purified acetone carboxylase in a total volume of 1 mL at pH 7.6. The addition of P-hydroxybutyrate dehydrogenase (3 U) and NADH (0.2 mM) allowed acetoacetate formation to be coupled to the oxidation of NADH. Assays were pre-incubated for 2 min. at 30° C. with all assay components except acetone. Assays were initiated by addition of acetone (2 mM). The reaction was monitored by measuring the decrease in absorbance at 340 nm ($\varepsilon_{340}$ of 6.22 mM$^{-1}$·cm$^{-1}$ for NADH) over time in an Agilent Technologies (Palo Alto, Calif.) model 8453 UV-Visible Spectroscopy System containing a thermostat-controlled cell holder at 30° C.

Acetone carboxylase coupled to $H_2O_2$ formation spectrophotometric assay. Assays were performed in 2 mL (1 cm path length) quartz cuvettes and contained ATP (0.1 mM), MgSO$_4$ (10 mM), potassium acetate (80 mM), potassium phosphate (50 MM), $CO_2$ (50 mM (1 mol CO2(g) to 4 mol potassium bicarbonate to maintain pH)), 40 p$_g$ purified acetone carboxylase, phosphoenolpyruvate (2 mM), pyruvate kinase (20 U), myokinase (15 U), pyruvate oxidase (2 U), peroxidase (15 U), flavin adenine dinucleotide (0.01 mM), cocarboxylase (0.2 mM), 4-aminoantipyrine (0.5 mM), and N-ethyl-N-(2-hydroxy-3-sulfopropyl)-m-toluidine (0.02% w/v) in a total volume of 1 mL at pH 7.5. Coupling enzymes and reagents (that is phosphoenolpyruvate, pyruvate kinase, myokinase, pyruvate oxidase, flavin adenine dinucleotide, and cocarboxylase,) allowed ATP hydrolysis to be coupled to $H_2O_2$ formation (pyruvate oxidation). Addition of peroxidase, 4-aminoantipyrine, and N-ethyl-N-(2-hydroxy-3-sulfopropyl)-m-toluidine allowed $H_2O_2$ formation to be monitored spectrophotometrically at 550 nm ($\varepsilon_{550}$ of 36.88 mM$^{-1}$·cm$^{-1}$ for quinoneimine dye product) over time in a thermostat-controlled cell holder at 30° C. Assays were pre-incubated for 2 min. at 30° C. with all assay components except acetone. Assays were initiated by addition of acetone (5 mM).

Example 2

Secondary Alcohol Dehydrogenase NADH Oxidation Spectrophotometric Assay

Assays were performed in 2 mL quartz cuvettes and contained NAD(H) (0.2 mM), potassium phosphate buffer (25 mM), and a source of enzyme (cell-free extracts, column fractions, or purified enzyme) in a total reaction volume of 1 mL at pH 6.2 (for ketone reduction assays) or pH 7.8 (for alcohol oxidation assays) at 30° C. Assays were pre-incubated for 1.5 min. at 30° C. with all assay components except substrate. Assays were initiated by addition of substrate (2.5 mM) and monitored over time by measuring the change in absorbance at 340 nm ($\varepsilon_{340}$ of 6.22 mM$^{-1}$·cm$^{-1}$ for NADH).

Secondary Alcohol Dehydrogenase Coupled to $H_2O_2$ Formation Spectrophotometric Assay.

Assays were performed in 2 mL (1 cm path length) quartz cuvettes and contained potassium phosphate (50 mM), 1.5 p$_g$ purified S-ADH, NADH (50 µM), lactate (10 mM), lactate dehydrogenase (20 U), pyruvate oxidase (2 U), peroxidase (15 U), flavin adenine dinucleotide (0.01 mM), cocarboxylase (0.2 mM), 4-aminoantipyrine (0.5 mM), and N-ethyl-N-(2-hydroxy-3-sulfopropyl)-m-toluidine (0.02% w/v) in a total volume of 1 mL at pH 6.2. Coupling enzymes and reagents (that is lactate, lactate dehydrogenase, pyruvate oxidase, flavin adenine dinucleotide, and cocarboxylase) allowed NADH oxidation to be coupled to $H_2O_2$ formation (pyruvate oxidation). In some assays (where specified), lactate and lactate dehydrogenase were replaced with alanine (10 mM) and alanine dehydrogenase (2 U). Assays were monitored spectrophotometrically at 550 nm ($\varepsilon_{550}$ of 36.88 mM$^{-1}$·cm$^{-1}$ for quinoneimine dye product) over time in a thermostat-controlled cell holder at 30° C. as described above. Assays were pre-incubated for 2 min. at 30° C. with all assay components except acetone. Assays were initiated by addition of acetone (2.5 mM).

Primary Alcohol Dehydrogenase Coupled to Primary Alcohol Oxidase Substrate Recycling Assays.

Assays were performed in 2 ml (1 cm path length) quartz cuvettes and contained potassium phosphate (25 mM), alcohol dehydrogenase (1 U), NADH (100 µM), alcohol oxidase (2 U), peroxidase (15 U), 4-aminoantipyrine (0.5 mM), and N-ethyl-N-(2-hydroxy-3-sulfopropyl)-m-toluidine (0.02% w/v) in a total volume of 1 mL at pH 6.2. Assays were monitored spectrophotometrically at 550 nm ($\varepsilon_{550}$ of 36.88 mM$^{-1}$·cm$^{-1}$ for quinoneimine dye product) or at 340 nm ($\varepsilon_{340}$ of 6.22 mM$^{-1}$·cm$^{-1}$ for NADH) over time in a thermostat-controlled cell holder at 30° C. as described above. Assays were pre-incubated for 2 min. at 30° C. with all assay components except ethanol. Assays were initiated by addition of ethanol (50 µM or 5 µM)

Stability studies. A sufficient quantity of enzyme for each individual activity assay (for example, 1.5 p$_g$ S-ADH) was aliquoted into 1.5 mL microcentrifuge tubes with specified concentrations of additives (for example trehalose (10% w/v)) in buffer (25 mM MOPS, pH 7.6) and frozen at −80° C. for 1 h. Samples were then placed in a shelf freeze dryer (Virtis model Advantage ES) and held at −50° C. (shelf temperature) for 16 h, and then increased to 20° C. for 4 h. Freeze-dried samples were removed and allowed to sit at room temperature (17 to 24° C.) over time. At specified time points, samples were re-hydrated and assayed as described above.

Protein characterizations. Sodium dodecyl sulfate-polyacrylamide gel electrophoresis (SDS-PAGE) was performed following the Laemmli procedure (Laemmli, U. K., Nature, 227:680-685 (1970)) using a 12% T, 2.7% C gel. "% T" indicates weight percent of total monomers, a measure of total monomer concentration, which is given by % T=100× ((grams acrylamide)+(grams cross-linker))/total gel volume (in mL); "% C" indicates weight percent of cross-linker, which is given by % C=100×(grams cross-linker)/((grams acrylamide)+(grams cross-linker)); and the cross-linker used was N,N'-methylene-bis-acrylamide. Electrophoresed proteins were visualized by staining with Coomassie Blue (PhastGel Blue R, catalog number 17-0518-01, Amersham Pharmacia Biotech). The apparent molecular masses of polypeptides based on SDS-PAGE migration were determined by comparison with R$_f$ values of standard proteins. N-terminal sequencing was performed by Commonwealth Biotechnologies, Inc. (Richmond, Va.). Protein concentrations were determined by using a modified biuret assay (V. J. Chromy et al., Clin. Chem., 20:1362-63 (1974) with δ-globulin as the standard.

Mass spectrometry analysis of enriched S-ADH and generation of peptide amino acid sequences was performed as follows. The S-ADH soluble protein was characterized by high-resolution two-dimensional gel electrophoresis. Proteins (30 p$_g$) were solubilized for isoelectric focusing (IEF) analysis in rehydration sample buffer consisting of 5 M urea, 2 M thiourea, 2% (w/v) CHAPS (3-[(3-cholamidopropyl) dimethylammonio]-1-propane-sulfonate), 2% (w/v) SB 3-10 (2-(decyldimethylammonio)propanesulfonate), 40 mM TRIS, 2 mM tributyl phosphine (added to rehydration solution just before use), and 0.2% Bio-Lyte 3/10 (Bio-Rad, Hercules, Calif., cat. no. 163-2104). Protein/rehydration solution was rehydrated into 11 cm IPG ReadyStrip pH 3-10 (Bio-Rad, Cat. no. 163-2014) under passive conditions 0 volts, 20° C., 16 hrs.

One-dimensional isoelectric focusing was carried out on a Protean IEF cell (B-Rad, model no. 526BR02142) for 35,000 volt-hours using IPG ReadyStrips (Bio-Rad). Following first dimension electrophoresis, gels were equilibrated for 20 minutes in a buffer containing 20% glycerol, 0.375 M Tris, 6 M urea, 2% SDS, and 5 M tributyl phosphine. IPG ReadyStrips were placed on top of a Criterion™ precast 1 mm 4-20% gradient Tris-HCl-SDS gel (Bio-Rad, cat. no. 345-0036) and 0.5% warm Agarose containing 0.01% bromophenol blue (Bio-Rad, cat. no. 161-0404) was added to the remaining well. Electrophoresis was carried out on a Criterion mini electrophoresis cell (Bio-Rad, cat. no. 165-6001) at room temperature. The electrophoresis running buffer was prepared from a 10× Tris-glycine-SDS solution (Bio-Rad, cat. no. 161-0732). Following assembly of the gel system and addition of the running buffer, the electrophoresis was carried out at an initial current of 2 mA, 3500 volts, 45 watts, for 1.5 hrs. The current was ramped up to 5 mA for 30 minutes followed by 10 mA for 2-3 hrs. Typical run times were between 4-5 hrs. Following electrophoresis, gels were stained in a buffer consisting of 17% ammonium sulfate, 30% methanol, 3% phosphoric acid, and 0.1% coomassie brilliant blue G250 (Bio-Rad, cat no. 161-0436), for at least 12 hrs. Gels were rinsed with water and stored in 2% acetic acid until further processing.

Colloidal Coomassie-stained gel images were captured using Bio-Rads Fluor-S Multilmager (Bio-Rad, cat. no. 170-7700). Digital filtering algorithms were used to remove non-uniform background without removing critical image data. Internal standards (molecular weight markers) were used initially to determine the molecular weight of the targeted proteins of interest. The molecular weight and pI of the S-ADH protein were determined by comparison of its position on the two-dimensional gel relative to the protein standards.

Protein spots relative to S-ADH from the 2-D gel were excised manually. The gel pieces were macerated and destained with 25 mM ammonium bicarbonate/50% acetonitrile in a 1.5 mL microfuge tube with vigorous shaking for 30 minutes. The blue-tinted destaining solution was removed and discarded with a fine-tip pipette. The destaining step was repeated until the stain was removed from the gel pieces. The gel pieces were dried under vacuum for 10 to 15 minutes. Proteins were digested overnight at 37° C. in a total volume of 25 μL of sequence-grade, modified trypsin (Roche Diagnostics, Indianapolis, Ind.) at a final protein of 25 ng/μL in 25 mM ammonium bicarbonate. Peptides were eluted with 50% acetonitrile and 0.5% trifluoroacetic acid. All peptide samples were concentrated, desalted, and detergents removed by using C18 reversed-phase ZipTip™ pipette tips as described by the manufacturer (Millipore, Bedford, Mass., cat. no. ZTC18S096).

The resulting tryptic peptides were analyzed directly by mass spectrometry. Mass spectrometry experiments were carried out on a PerSeptive Biosystems (Framingham, Mass.) Voyager DE-STR equipped with a $N_2$ laser (337 nm, 3-nsec pulse width, 20-Hz repetition rate). The mass spectra were acquired in the reflectron mode with delayed extraction. Internal mass calibration was performed with low-mass peptide standards, and mass-measurement accuracy was typically ±0.1 Da. All peptide samples were diluted in a-cyano-4-hydroxycinnamic acid, which had been prepared by dissolving 10 mg in 1 mL of aqueous 50% acetonitrile containing 0.1% trifluoroacetic acid.

Several tryptic peptide masses from S-ADH were further sequenced by one of the following approaches by mass spectrometry as described below.

Approach 1: Tryptic digests of the protein were derivatized with chlorosulfonylacetyl chloride reagents as described by Keough T., Lacey M. P., Youngquist R. S. *Proc. Natl. Acad. Sci. USA* 1999; 96 7131. The sulfonated sample was acidified with trifluoroacetic acid and cleaned up directly using C18 mini-columns (ZipTips™, Millipore). The derivatized peptides were eluted into α-cyano-4-hydroxycinnamic acid (Fluka, cat. no. 28480) and plated directly onto MALDI plates. Derivatized peptides were analyzed on an Applied Biosystems Voyager DE-STR time-of-flight mass spectrometer equipped with a $N_2$ laser. All mass spectra were acquired in the reflectron mode with delayed extraction. External mass calibration was performed with low-mass peptide standards, and mass measurement accuracy was typically ±0.2 Da. PSD fragment ion spectra were obtained after isolation of the appropriate derivatized precursor ions using timed ion selection. Fragment ions were refocused onto the final detector by stepping the voltage applied to the reflectron in the following ratios: 1.0000 (precursor ion segment), 0.9000, 0.7500, 0.5625, 0.4218, 0.3164, and 0.2373 (fragment ion segments). The individual segments were stitched together using software developed by Applied Biosystems. All precursor ion segments were acquired at low laser power (variable attenuator=1980) for 100 laser pulses to avoid detector saturation. The laser power was increased (variable attenuator=2365) for the remaining segments of the PSD acquisitions. The PSD data were acquired at a digitization rate of 20 MHz; therefore, all fragment ions were measured as chemically averaged and not monoisotopic masses.

Approach 2: Sequence tags were obtained from S-ADH tryptic peptides. Post source decay (PSD) fragment ion spectra were acquired for four peptides after isolation of the appropriate precursor ion by using timed ion selection. Fragment ions were refocused onto the final detector by stepping the voltage applied to the reflector in the following ratios: 1.0000 (precursor ion segment), 0.9000, 0.7500, 0.5625, 0.4218, 0.3164, and 0.2373 (fragment segments). The individual segments were stitched together by using software provided by PerSeptive Biosystems. All precursor ion segments were acquired at low laser power (variable attenuator=1,450) for <256 laser pulses to avoid saturating the detector. The laser power was increased for all of the remaining segments of the PSD acquisitions. Typically, 200 laser pulses were acquired for each fragment-ion segment. The PSD data were acquired at a digitization rate of 20 MHz. Mass calibration was performed with peptide standards. Metastable decompositions were measured in all PSD mass spectrometry experiments.

Approach 3: Sequence tags were obtained from S-ADH tryptic peptides by ESI MS/MS the mass spectra were acquired on a Micromass Q-TOF2 quadrupole/time of flight MS system.

Example 3

Initial Electrochemical Measurement of NADH and Correlation to Spectrophotometric Data 10 micron disc carbon fiber microelectrodes were purchased (from Bioanalytical Systems ("BAS"), West Lafayette, Ind. (part number MF-2007)) and pretreated using the method of Kuhr et. al. (63). The electrode surface was polished for 10 min. with 1 μm diamond paste (Bioanalytical Systems) and sonicated in hot toluene for 2 min. To remove residual polishing material, the microelectrode was rinsed once in methanol and once in water, then sonicated twice in water for 1 min. The polished microelectrode was subsequently pretreated electrochemically in 1 M HCl by twice applying 10 cycles of 100 V/s from −200 mV to +1800 mV. Then the microelectrode was treated in 100 mM potassium phosphate buffer by twice applying 10 cycles of 0 to +1200 mV at 100 mV/s. Background scans were then obtained from phosphate buffer alone. All potentials were referenced versus a Ag/AgCl reference electrode (Bioanalytical Systems). After baseline fast-scan cyclic voltammograms (CVs) were obtained for the enzyme (1 U/mL) and NAD(P)H (2 mM), the required volume of aqueous acetone was added (20 mM final concentration). The solution was quickly mixed, and fast-scan CVs were obtained every 1 min. for 25 min. The buffer-only background was subtracted from each CV with BAS 100W electrochemical software version 2.3 (obtained from Bioanalytical Systems, West Lafayette, Ind., hereinafter "BAS").

Unless otherwise indicated, all electrochemical measurements were performed using a Bioanalytical Systems (BAS) Model 100A or B electrochemical analyzer coupled to a BAS PA-1 preamplifier and a Faraday cage (part number MF-2500), wherein all waveforms were generated and currents acquired via BAS 100 W electrochemical software version 2.3. The data were processed using Microsoft Excel 97 SR-2 and BOMEM GRAMS/32 version 4.04, Level II (Galactic Industries Corporation). The electrochemical cell was a custom-built 0.20 mL cell, constructed from Plexiglas (acrylic polymer sheet, from Atofma Corp., Paris, France), containing a Ag/AgCl reference electrode, the pretreated carbon fiber microelectrode, and a Pt wire auxiliary electrode.

To correlate spectrophotometric with electrochemical data for both enzymes, the same reaction conditions were used for both analyses. For S-ADH from *T. brockii*, the 1 mL reaction volume comprised final concentrations of 2 mM NADPH, 20 mM acetone, and 1 U S-ADH. For S-ADH from *X. autotrophicus* Py2, the 1 mL reaction volume comprised final concentrations of 2 m NADH, 20 mM acetone, and 1 U S-ADH. For both reactions, baseline $A_{340}$ was obtained for the enzyme and NAD(P)H versus a phosphate buffer blank. The cuvette containing the reaction solution was then removed from the spectrophotometer, and the 0.4 mL of solution was removed from the cuvette and combined with the remaining 0.6 mL. The required volume of aqueous acetone was added to the 1.0 mL reaction. The solution was mixed, 0.4 mL was added to the cuvette, and the cuvette replaced in the spectrophotometer. The decrease in $A_{340}$ was then monitored for 30 min. using a Shimadzu UV-VIS-NIR scanning spectrophotometer (model UV-3101PC, Colombia, Md.). Data were acquired using UVPC Personal Spectroscopy Software version 3.9 (Shimadzu, Colombia, Md.) and processed using Microsoft Excel 97 SR-2. Quartz cuvettes with a 1 mm pathlength and a 0.4 mL volume were purchased (from Fisher Scientific, Pittsburgh, Pa., part number 14-385-906A).

Electrochemical measurement of acetone-dependent NADH consumption using Meldola's Blue-modified carbon electrodes. A glassy carbon disk electrode modified with the electrocatalyst Meldola's blue was prepared as follows. A 3-mm diameter glassy carbon electrode (BAS part number MF-2012) was first wet-polished with a 1 μm diamond suspension, sonicated in deionized water for one minute, and then further polished with 0.05 μm alumina polishing suspension. The freshly polished electrode was washed thoroughly by sonication in deionized water and subsequently pretreated electrochemically in 5 mL deoxygenated 100 mM phosphate buffer (pH 7.2) by applying 20 cycles of 5 V/s from −500 mV to +300 mV, four times. After the cycling, a constant polarizing potential at −0.5 V was applied for 60 s. The electrochemically pretreated electrode was then soaked in 0.5% of Meldola's blue (Aldrich, Milwaukee, Wis., catalog number 32,432-9) at room temperature for 30 min. The electrode was rinsed with deionized water before use.

Screen-printed carbon electrodes formulated with Meldola's Blue mediator were purchased from Gwent Electronic Materials Ltd. (Pontypool, United Kingdom). The disposable strips were configured in the geometry described by Hart et al. and consisted of two screen-printed electrodes deposited onto a polyethylene substrate. The working electrode was graphite carbon containing the electrocatalyst Meldola's Blue (part number C70902D2 from Gwent), and the reference/counter electrode was Ag/AgCl printed ink (part number C61003D7 from Gwent). The working electrode area was defined by printing an additional dielectric coating (part number D2000222D2 from Gwent). The electrode geometric area is 3×3 mm, or 9 mm². The electrodes were pre-soaked in phosphate buffer for 10 minutes before use to remove loosely bound Meldola's Blue.

The acetone-dependent consumption of NADH catalyzed by S-ADH was measured with Meldola's blue-carbon electrodes prepared as above using chronoamperometry in a 1 mL reaction volume containing 100 mM potassium phosphate buffer (pH 7.2), NADH (500 μM), S-ADH (1 U), and varying concentrations of acetone. After a 2 min. incubation period, the potential was stepped from open circuit to 68 mV (vs. Ag/AgCl) and the current was recorded after 120 s.

Measurement of acetone-dependent consumption of NADH using commercial blood glucose disposable test strips. Disposable glucose biosensor strips and reader (Precision Xtra Advanced Diabetes Management System) are available from MediSense (a division of Abbott Laboratories, Bedford, Mass.). 1 mL reaction volumes containing 25 mM potassium phosphate buffer (pH 6.2), NADH (2 mM), S-ADH (20 U), and acetone (0.5, 1.0, 1.5, 2.0 mM respectively) were incubated at room temperature. After 5 min., a 20-4 aliquot was removed from each reaction mix and applied to a disposable strip pre-inserted in the glucose meter. The meter reading value (mg/dL of glucose equivalent) was recorded and plotted to the amount of acetone added.

Secondary alcohol dehydrogenase coupled to $H_2O_2$ formation electrochemical assay. A disk platinum electrode (BAS part number MF-2013) was used to monitor $H_2O_2$ produced by the S-ADH coupled enzymatic reaction in response to acetone concentration. Before measurements the electrode surface was polished using $Al_2O_3$ paste for 1 min. and then rinsed with deionized water, sonicated for 1 min. and rinsed with water again. The polished Pt electrode was then pretreated electrochemically by applying 10 cycles of 100 mV/s from +200 mV to +900 mV. All potentials were referenced versus a Ag/AgCl electrode (BAS part number MF-2078). Assays contained potassium phosphate (100 mM, pH 7.2), purified S-ADH (1 U/mL), NADH (201 μM), lactate (100 mM), lactate dehydrogenase (5 U/mL), pyruvate oxidase (4 U/mL), flavin adenine dinucleotide (0.01 mM), cocarboxylase (0.2 mM), in a total volume of 0.5 mL. Assays were initiated by addition of acetone. After a 2 min. incubation period, the potential was stepped from open circuit to 350 mV. The oxidative current was recorded after 120 and plotted against acetone concentration.

Disposable electrode materials were evaluated to monitor acetone-dependent $H_2O_2$ produced by the coupled enzyme reaction using the identical enzyme reagent system and similar electrochemical technique as described above for the disk platinum electrode. Screen-printed platinized carbon/graphite electrodes and cobalt phthalocyanine carbon electrodes were purchased (part numbers C2000511D1, and C40511D8, respectively, Gwent Electronics Materials, Ltd.) with the same electrode geometry as described earlier for the Meldola's Blue screen-printed carbon electrodes. Screen-printed platinized carbon electrodes were pre-soaked in phosphate buffer for 5 min. before use. Assays were initiated by addition of acetone and incubated for 2 min. at which time the potential was stepped from open circuit to 350 mV. The oxidative current was recorded after 120 s. Cobalt phthalocyanine-modified screen-printed carbon electrodes were pre-soaked in phosphate buffer for 5 min. before use. After each addition of acetone, the reaction was allowed to incubate for 3.5 min. Chronoamperometric measurements were made with an initial quiet time of 5 s at 150 mV, and then the potential was stepped to 650 mV for 30 s and the current recorded. One cobalt phthalocyanine-modified screen-printed electrode was used for each experiment and then discarded.

A prototype disposable platinized carbon electrode was constructed by cutting ⅛ inch (3.06 mm) diameter circular disks (using a manual hole puncher) of Toray carbon paper (porous carbon paper) or cloth, loaded with 20% (w/w) platinum nanoparticles (these platinum particles are nanonoparticles deposited on carbon; the platinum nanoparticle-loaded paper or cloth was purchased from ETEK Division of De Nora North America, Somerset, N.J., part number SLS-SPEC) and attached to a screen-printed carbon working electrode (part number C10903D14 from Gwent Electronics Materials, Ltd.) using double-sided carbon tape (also ⅛ inch (3.06 mm) diameter disk). In some experiments, 20 µM of non-ionic detergent TRITON X-100 (t-octylphenoxypoly-ethoxyethanol; catalog number T-8787, from Sigma Chemical Co.) or BRIJ 30 (tetraethylene glycol monododecyl ether; catalog no. P-1254, from Sigma) was applied to the ETEK material disk and allowed to dry before use. Before measurements, the electrode was pretreated electrochemically by applying 10 cycles of 100 mV/s from +200 mV to +900 mV twice. Assays were initiated by addition of acetone and incubated for 2 min. Chronoamperometric measurements were made with a quiet time of 2 s at 215 mV, and then the potential was stepped from 215 mV to 350 mV vs. Ag/AgCl. The oxidative current was recorded after 30 s.

Reflectance photometry measurement of acetone-dependent $H_2O_2$ formation using glucose disposable test strips and correlation to electrochemical data. Disposable glucose biosensor strips and reader were purchased (OneTouch Basic read and strips from Lifescan, Inc., Milpitas, Calif.). Successive additions of 100 acetone were added to a 1 mL reaction volume containing the S-ADH coupled enzyme system (as described above) and incubated at room temperature. Each acetone addition was allowed to react for 4 min. and then a 20-µL, aliquot was removed from the reaction mix and applied to a disposable strip pre-inserted in the glucose meter. The meter reading value (mg/dL of glucose equivalent) was recorded and plotted against the total concentration of acetone. $H_2O_2$ concentration was also monitored chronoamperometrically using a disk platinum electrode as described above. The correlation between the electrochemical assay and the colorimetric readings were plotted.

Enzyme-based electrochemical measurement of gas phase acetone. Gas phase samples (0-10 ppm v/v) of acetone were prepared by injecting standard concentrations of acetone into a calibrated airbag (10 L bag, Calibrated Instruments, Inc, Ardsley, N.Y.) filled with 7 L of water-saturated air and 1 L of dry air, and allowed to evaporate at 37° C. (about 30 min.). The gas samples produced from this system closely simulate human breath in terms of temperature and moisture content. The gas sampling system was calibrated (that is, concentration of acetone gas phase and liquid phase samples) using gas chromatography with a Hewlett Packard 5890 gas chromatograph equipped with flame ionization detection and an on-column injector. 1 µL aqueous samples were applied to a 15 m long, coiled capillary column (Nukol, 0.53 mm diameter with 0.50-µm layer of liquid phase, catalog number 25326, available from Supelco, Inc., Bellafonte, Pa.). The oven temperature was held at 40° C. for 4 min., then increased at 25° C./min. to 200° C. The carrier gas flow rate was 5 mL/min. of helium.

Two types of sampling techniques were used to partition acetone from the gas phase into the liquid phase; a foam system, and a thin-aqueous layer system. For the foam system, a piece of polyurethane foam was cut into a cylindrical shape (19 mm long and 10 mm in diameter) so that the volume was about 1 mL. The foam was boiled in water for 20 min. and then inserted into a 3 cc disposable plastic syringe. The syringe plunger was inserted and pushed firmly to remove excess water and then removed. Before introducing gas phase acetone samples, 50 µL of water or phosphate buffer was loaded into the foam. Once the water contacted foam, the surface tension sucked water into the foam cell and the water distributed evenly onto foam surface. The syringe containing wetted foam was then connected via tubing to the gas sampling system and the gas sample passed through the foam with a flow rate 5 L/min. for 12 seconds either by running a diaphragm pump or by manually pushing the airbag. This allowed the total gas sample volume to equal 1 L. After sampling, the syringe containing foam was quickly disconnected and the plunger reinserted. The liquid was then squeezed out into an electrochemical cell for electrochemical analysis or into a vial insert for gas chromatography analysis. For electrochemical measurements, the acetone-partitioned water sample was mixed with concentrated enzyme solution (S-ADH and coupling enzymes as discussed above) to make the desired final enzyme solutions and incubated for 2 min. The acetone-dependent $H_2O_2$ formed from the enzyme reaction was measured chronoamperometrically as described above.

For the thin aqueous layer sampling method, the gas was released from the airbag in a fine stream at a flow rate of 500 mL/min. for 2 min. so that the total volume of gas was equal to 1.0 L. In this experiment, the working electrode was inverted (electrode surface facing up), so that a small amount of enzyme solution (50 µL) forms a relatively thin layer of liquid to cover the electrode surface. The gas was blown perpendicular to the liquid surface. The gas stream stirred the liquid to enhance the mass transfer of acetone from gas phase into liquid phase. After the gas sample flow, the enzyme solution was allowed to react for 1 min. The acetone-dependent $H_2O_2$ formed from the enzyme reaction was measured chronoamperometrically as described above. The current responses were plotted against the gas-phase acetone concentration in the airbag.

Data analysis. Kinetic constants ($K_m$ and $V_{max}$) were calculated by fitting initial rate data to the Michaelis-Menten equation and using the software KaleidaGraph Fourth Edition, (Synergy Software, Reading, Pa.).

Results

Figure 2:
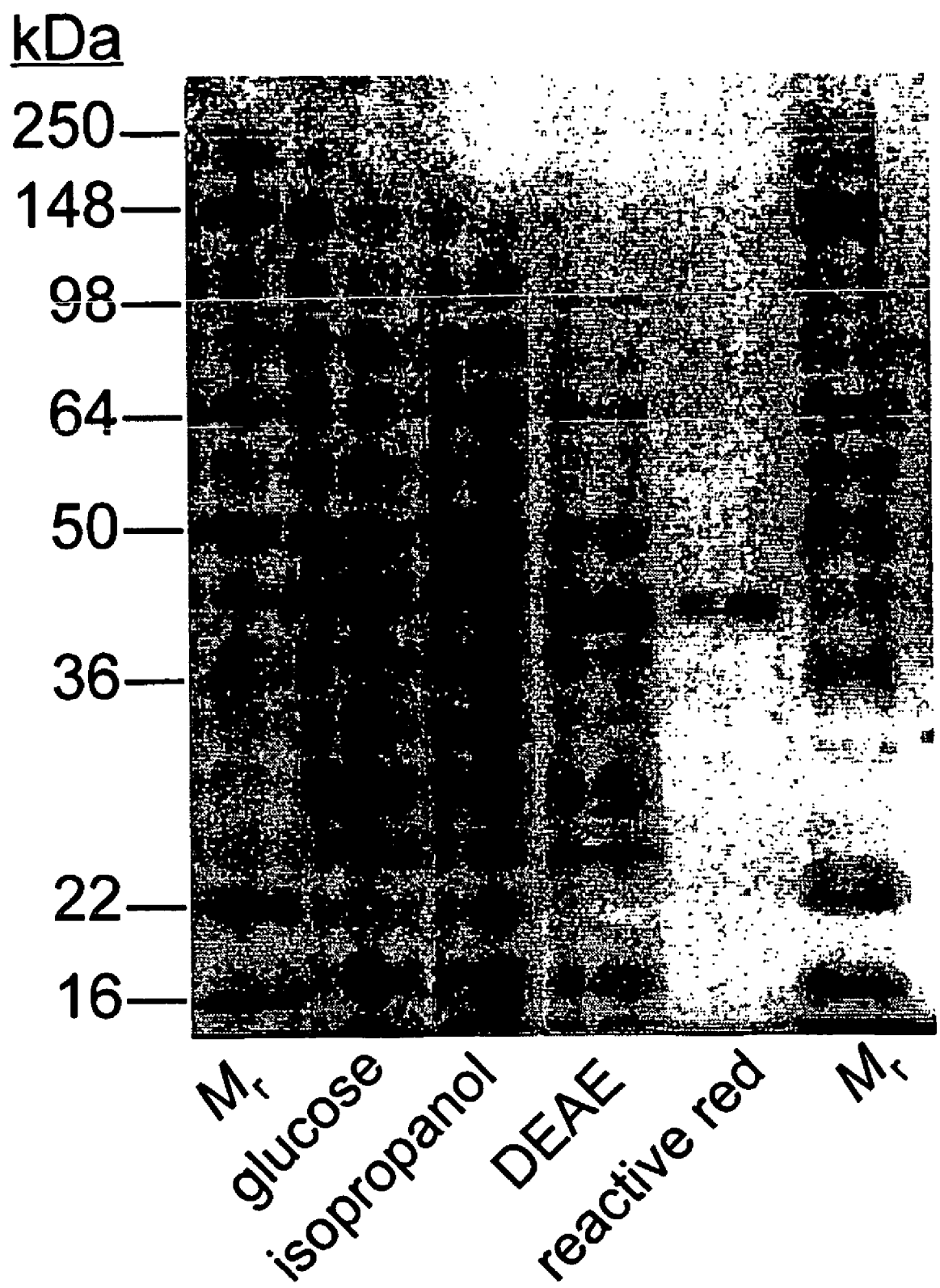
FIG. 2 depicts a sodium-dodecyl-sulfate-Polyacrylamide Gel Electrophoresis (SDS-PAGE) analysis of S-ADH purification from *X. autotrophicus* st. Py2. S-ADH was determined to have protein N-terminus of SEQ ID NO: 7.

Purification of S-ADH from *X. autotrophicus* strain Py2. S-ADH enzymes are believed to be involved in primary (growth on isopropanol) or intermediary steps (growth on propane) in bacterial pathways involving aliphatic hydrocarbon catabolism. These enzyme reactions are freely reversible where the reaction direction is dependent on the chemical equilibrium. The reverse reaction, that is the reduction of acetone to isopropanol with concomitant oxidation of NADH or NADPH (most dehydrogenases have preference for one coenzyme over the other), arguably provides the substrate specificity and redox chemistry necessary for an enzyme-based electrochemical sensor. For these reasons, this class of enzymes was investigated in more detail by testing for S-ADH activity in cell extracts of isopropanol-, propane-, and acetone-grown bacterial cultures (data not shown; growth screens and isolates performed as described in Experimental Procedures). Of these, cell extracts of isopropanol-grown *X. autotrophicus* strain Py2 had the highest S-ADH specific activity (1.2 µmol acetone reduced-min$^{-1}$·mg$^{-1}$ protein) and also preliminarily observed to have specificity for secondary alcohols over primary alcohols. To investigate the properties of this enzyme further, S-ADH was purified on the basis of its ability to reduce acetone in the presence of NADH or oxidize isopropanol in the presence of NAD$^+$. The enzyme was purified about 40-fold using DEAE-Sepharose and RED SEPHAROSE chromatography with an estimated recovery of 30 to 40%. As shown in FIG. 2, this two-step purification resulted in the enrichment of a single polypeptide with an apparent molecular mass of 42 kDa on SDS-PAGE. A polypeptide band that migrated with the same apparent molecular mass was weakly visualized in cell extracts of isopropanol-grown Xanthobacter that was not readily visible at this same position in cell extracts of glucose-grown Xanthobacter (FIG. 2). Consistent with SDS-PAGE analysis, S-ADH activity in glucose-grown cell extracts was only 3% of the activity observed in isopropanol cell extracts, suggesting that S-ADH is induced by the presence of isopropanol. Mass spectrometry provided a more accurate molecular mass estimate of 37.1 kDa for purified S-ADH, which is consistent with observed apparent molecular mass determined by SDS-PAGE. The pI of S-ADH was determined to be 7.4 by isofocusing electrophoresis. The N-terminal sequence of the S-ADH polypeptide was determined to be MKGLVYRG-PGKKALE (SEQ ID NO:7) by Edman degradation. Additional peptide amino acid sequences were determined by digesting the polypeptide with trypsin to produce "tryptic fragment" and employing matrix-assisted laser desorption ionization-mass spectrometry using post-source decay sequencing (PSD-MALDI) to determine their amino acid sequences.

The amino acid sequences of six peptides were obtained by derivatizing the fragments followed by sequence analysis using PSD-MALDI (Table 2).

TABLE 2

Sequences of derivatized tryptic fragments of Xanthobacter Py2 S-ADH.

| Observed MH+ (m/z) | Amino Acid Sequence | |
|---|---|---|
| 1431.33 | PVAVDHGP(FS)PHK | (SEQ ID NO: 8) |
| 1111.1 | GG(L/I)GVYHQ | (SEQ ID NO: 9) |
| 1047.2 | A(L/I)EEVPHPR | (SEQ ID NO: 10) |
| 1047.1 | HPSGDTR | (SEQ ID NO: 11) |
| 946.27 | GLVYRGPGK | (SEQ ID NO: 12) |
| 756.17 | HQ(I/L)ASSR | (SEQ ID NO: 13) |

The sequence of the peptide with the observed mass-to-charge ratio of 946.27 is identical to a nonamer present within the N-terminal sequenced derived by Edman degradation. Using PSD MALDI analysis, an additional four amino acid sequences were detected (Table 3).

TABLE 3

Sequences of Xanthobacter Py2 S-ADH fragments, by PSD-MALDI.

| Observed MH+ (m/z) | Amino Acid Sequence | |
|---|---|---|
| 1151 | LDNVPE | (SEQ ID NO: 14) |
| 1331 | FDQRQP | (SEQ ID NO: 15) |
| 2288 | GAGRIIAV | (SEQ ID NO: 16) |
| 2422 | QVEPLMS | (SEQ ID NO: 17) |

The amino acid sequences of S-ADH tryptic peptide fragments were also obtained by ESI MS/MS (Electrospray Ionization, tandem Mass Spectrometryflvlass Spectrometry). The resulting MS/MS analysis was consistent for the following amino acid sequences (Table 4).

TABLE 4

Sequences of Xanthobacter Py2 S-ADH fragments, by ESI MS/MS.

| Observed MH+ (m/z) | Amino Acid Sequence | |
|---|---|---|
| 1760.0 | FFADIIEAA | (SEQ ID NO: 18) |
| 1330.8 | DTVTTH | (SEQ ID NO: 19) |

Thus, the *Xanthobacter* Py2 S-ADH was characterized as a protein having NAD$^+$-dependent secondary alcohol dehydrogenase activity, having the ability to reduce acetone to isopropanol, and having specific activity for ketones and secondary alcohols; having, for the oxidation of isopropanol to acetone, (1) a pH optimum of approximately 7.8, and (2) an average specific activity ratio for secondary-to-primary alcohols of at least 50:1 when tested at pH 7.8 under equivalent conditions individually with C3-C5 straight chain secondary alcohols and with C2-C5 straight chain primary alcohols; having, for the reduction of acetone to isopropanol, (3) a pH optimum of approximately 6.2, (4) an apparent $K_m$ of approximately 144±18 µM, (5) an apparent $V_{max}$ of approximately 43.4±1.2 µmol acetone reduced min$^{-1}$·mg$^{-1}$ protein, (6) an apparent $k_{cat}$ of approximately 30.4 sec$^{-1}$, (7) an apparent $k_{cat}/K_m$ of approximately 2.1×10$^5$, and (8) a $K_m$ for NADH of approximately 5.1×0.4 µM; and comprising at least one polypeptide molecule that has (a) a molecular mass of approximately 37.1 kDa as determined by mass spectrometry, (b) a pI of approximately 7.4 as determined by isofocusing electrophoresis, and (c) a tetradecameric N-terminal amino acid sequence of SEQ ID NO:7, and that is capable of being degraded to form fragments having the amino acid sequences of SEQ ID NO:8 to SEQ ID NO:19.

In addition, a terminally-truncated version of this protein was also co-purified. This terminally-truncated version was missing a terminal decapeptide and yet functioned as well as the intact protein (data not shown). The term "enzyme" as used herein, means "catalytically functional biomolecule," which includes both whole native (or native-size) molecules, as well as terminally truncated versions retaining function, that is having up to about 10 amino acids deleted from at least one terminus. In specific reference to the Xanthobacter Py2 S-ADH, the term "enzyme" therefore includes both the whole native molecule and the terminally truncated versions.

Figure 4:
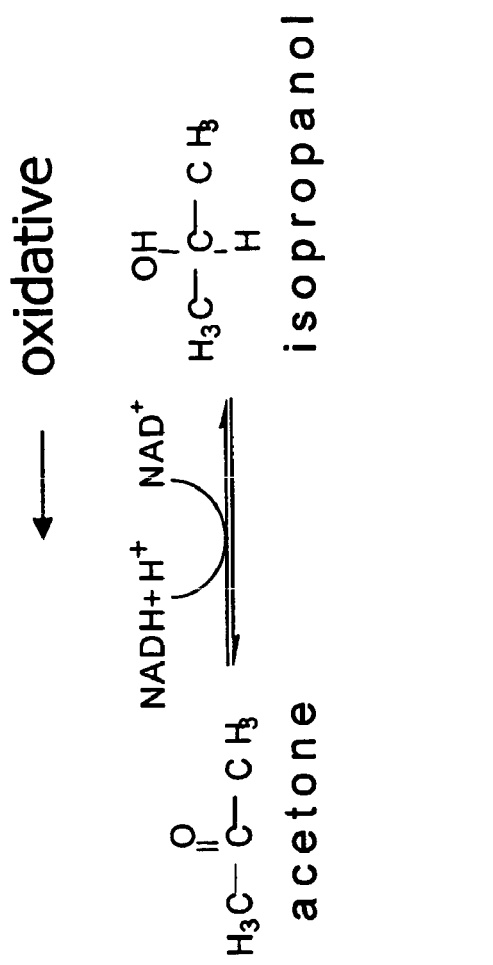
FIG. 4 shows substrate specificity of S-ADH from *X. autotrophicus* strain Py2 in performing alcohol oxidations. (NA indicates no activity was detected). S-ADH was determined to have protein N-terminus of SEQ ID NO: 7.

Substrate specificity and inhibition of S-ADH from *X. autotrophicus* strain Py2. In acetone reduction assays, NADH but not NADPH could serve as the electron donor (data not shown). The pH optimum for reducing acetone to isopropanol was 6.2 while the optimum for the reverse reaction was 7.8 (data not shown). Kinetic constants were calculated from data collected from assays in which the NADH or acetone concentration was held at a fixed saturating concentration, while the acetone or NADH concentration was varied in individual assays. The apparent $K_m$, $V_{max}$, $k_{cat}$, and $k_{cat}/K_m$, values were calculated to be 144±18 µM, 43.4±1.2 µmol acetone reduced $min^{-1} \cdot mg^{-1}$ protein, 30.4 $sec^{-1}$, and $2.1 \times 10^5$, respectively. The $K_m$ for NADH was calculated to be 5.1±0.4 µM. Of several compounds evaluated as alternative substrates, S-ADH exhibited specificity for ketones and secondary alcohols (FIGS. 3 and 4). In FIG. 4, "NA" indicates "no activity," that is that no activity toward the substrate was detected. As shown, primary alcohols exhibited no activity or very low activity in comparison. Among the ketones and secondary alcohols, the highest specific activities were observed with 2-pentanone and 2-pentanol for the reductive and oxidative reactions, respectively.

As a result, the only tested primary alcohol toward which the enzyme exhibited activity was 1-butanol and the specific activity measured (at pH 7.8) was only 1.7±0.2 µmol butanol oxidized $min^{-1}mg^{-1}$ protein. No activity toward ethanol, 1-propanol, or 1-pentanol was detected. The average specific activity toward C2-C5 straight chain primary alcohols was thus, at most, about 0.475 µmol alcohol oxidized $min^{-1}mg^{-1}$ protein. Activity toward secondary alcohols was tested for C3-C5 straight chain secondary alcohols. The enzyme exhibited activity toward all three, and the specific activity values measured (at pH 7.8) were 24±1.8 µmmol 2-propanol oxidized-$min^{-1}$-$mg^{-1}$ protein, 21±3.6 µmol 2-butanol oxidized·$min^{-1}mg^{-1}$ protein, and 37±1.1 µmol 2-butanol oxidized-$min^{-1}$-$mg^{-1}$ protein. The average specific activity toward C3-C5 straight chain secondary alcohols was thus, at least, about 25 µmol alcohol oxidized-$min^{-1}mg^{-1}$ protein. Therefore, for this S-ADH, the minimum average specific activity ratio for secondary-to-primary alcohols, when tested at pH 7.8 under equivalent conditions individually with C3-C5 straight chain secondary alcohols and with C2-C5 straight chain primary alcohols, may be given by 25/0.475 which equals 52.6; thus, this S-ADH enzyme, tested under these conditions, has an average specific activity ratio for secondary-to-primary alcohols of at least about 50:1.

Using saturating concentrations of acetone, no inhibition was observed for S-ADH activity in the presence of methanol, ethanol, and 1-propanol at concentrations about 13-fold over the $K_m$ value for acetone (data not shown). S-ADH activity was tested in the presence of higher concentrations of ethanol since this compound is a key potential inhibitor for diagnostic breath acetone analysis. S-ADH was 82-85% active in the presence of 41 mM ethanol which is equivalent to 500 ppm (v/v) gas phase ethanol and is the upper limit concentration of ethanol found in human breath.

The acetone detection limit of S-ADH was investigated using spectrophotometry in order to assess this enzyme's ability to detect the low levels of acetone present in human breath. Using a high loading of enzyme (4 U), the NADH consumption response time was less than 20 s and linear (correlation coefficient=0.99997) for acetone concentrations ranging from 0.058 to 5.8 ppm (w/v). The lower end of the acetone detection range (0.058 to 0.29 ppm (w/v)) is within the detection parameters required for diagnostic breath acetone analysis (lower breath acetone level is 0.3 to 0.8 ppm (w/v) for non-dieting individuals). Furthermore, this detection method is limited in sensitivity, therefore other detection methods (for example, electrochemical) may provide increased sensitivity for detecting lower concentrations of acetone using the S-ADH reaction.

Figure 5:
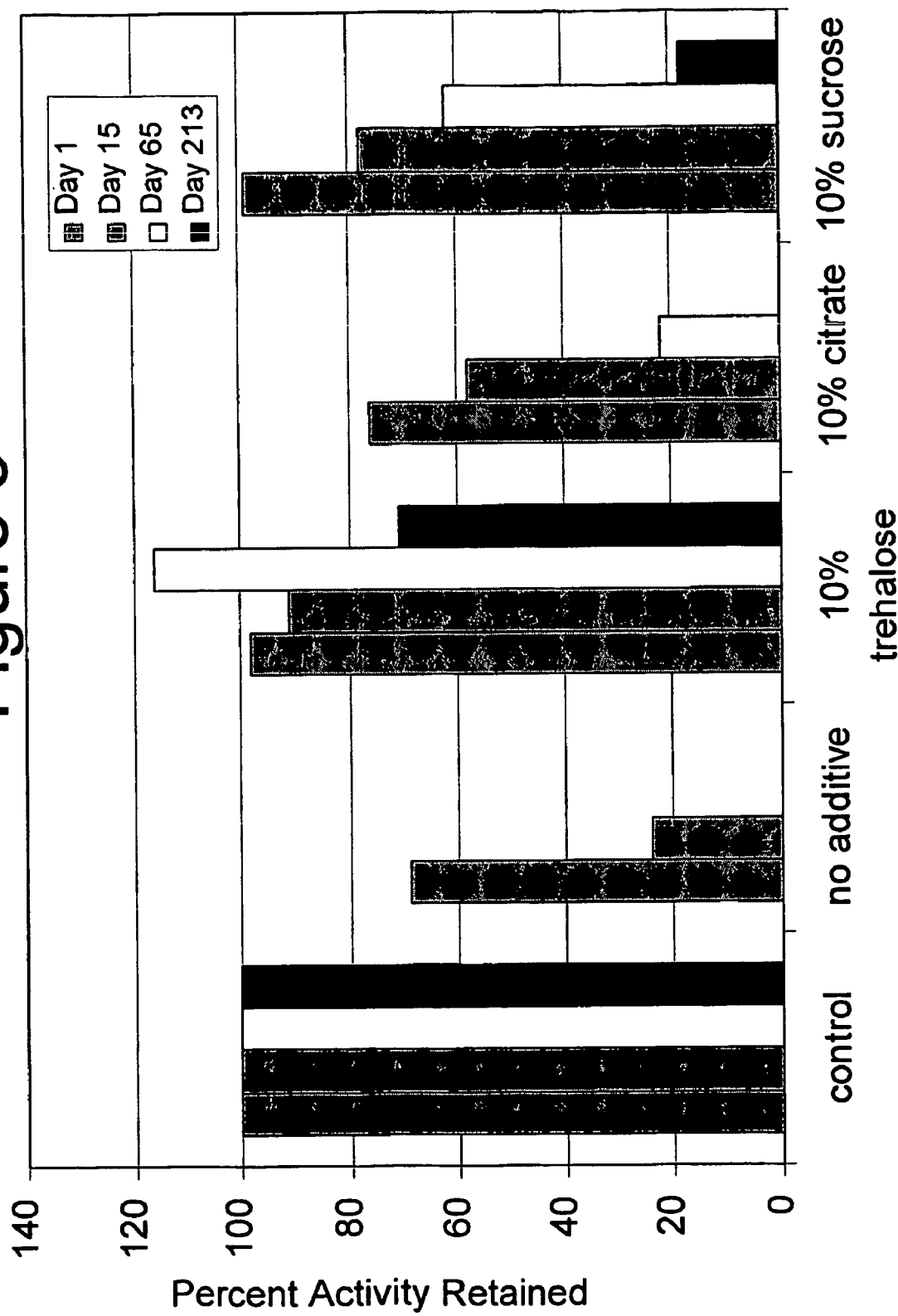
FIG. 5 graphically depicts the stability of lyophilized S-ADH from *X. autotrophicus* st. Py2 stored at room temperature, alone and with various additives (10% by weight trehalose, citrate, or sucrose). S-ADH was determined to have protein N-terminus of SEQ ID NO: 7.

Stability of S-ADH from *X. autotrophicus* strain Py2. Stability of the enzymes that are incorporated into biosensors is one of the main parameters that determine their commercial viability. Maintaining enzyme activity can influence storage costs, performance, and manufacturing processes. Therefore it was necessary to find conditions for stabilizing S-ADH activity for long periods at room temperature, preferably in a dry form. Enzyme stability can be enhanced by the presence of compatible solutes that maintain the ionic and hydrophilic environment surrounding the enzyme during lyophilization and storage. As can be seen in FIG. 5, purified S-ADH was lyophilized and found to retain approximately 60 to 70% activity relative to a non-lyophilized control when re-suspended and assayed within one day of lyophilization. The presence of the disaccharide trehalose was of considerable benefit in maintaining activity, where samples held at room temperature for 65 and 213 days retained approximately 100% and 70% activity, respectively S-ADH samples containing no additives were completely inactive after 65 days at room temperature. In a separate experiment, S-ADH was included into a mixture of compounds that closely resembles a formulation recently described for fabrication of a thick-film, screen-printed enzyme electrode. This formulation included the additives hydroxyethyl cellulose (2% w/v), DEAE-Dextran (10 mg/mL), and lactitol (10 mg/mL) and the mixture was allowed to air dry as opposed to being lyophilized. Using this mixture, S-ADH retained 100% of its activity after being stored at room temperature for 23 days (data not shown).

Biochemical comparison of S-ADH from *X. autotrophicus* strain Py2 to other S-ADH enzymes. S-ADH from *X. autotrophicus* strain Py2 represents the first S-ADH enzyme purified from a $CO_2$-dependent acetone-utilizing organism. This enzyme is similar in several respects to previously described secondary alcohol dehydrogenases in terms of its molecular mass and substrate specificity. The NAD-dependent secondary alcohol dehydrogenases from *Pseudomonas* sp. 6307 (ATCC®21439), *Mycobacterium vaccae* strain JOB-5 (ATCC 29678), *Candida boidinii* (ATCC® 32195), *Rhodococcus rhodochrous* PNKb1 (Ashraf & Murrell (1990)), and the NADP-dependent S-ADH from *Thermoanerobium brockii* all have subunit molecular masses ranging from 37 kDa to 48 kDa. S-ADH purified from M vaccae strain JOB-5 is a 37 kDa molecular weight (subunit) and is induced by growth on propane. In contrast to the *Xanthobacter* S-ADH, the M vaccae enzyme appears to have some specificity for primary alcohols in addition to secondary alcohols, although primary alcohols have significantly higher $K_m$ values (for example, $K_m$=0.05 mM vs. $K_m$=8.1 mM for 2-propanol and 1-propanol, respectively). Comparatively, the $K_m$ for acetone reduction was calculated to be 0.3 mM. Another difference is the pH optimum for the reduction and oxidation reactions. *M. vaccae* JOB-5 has a pH optimum of 10-10.5 for oxidizing 2-propanol and 7.5-8.5 for reducing acetone. Another secondary alcohol dehydrogenase was isolated from the propane-utilizing bacterium *R. rhodochrous* PNKb1 (Mr=42 kDa), although this enzyme exhibited nearly equal specificity for either secondary or primary alcohols (for example $K_m$=18 mM vs. $K_m$=12 mM for 1-propanol and 2-propanol, respectively). In contrast to the S-ADH enzymes found in propane utilizers, S-ADH from the methylotroph *Pseudomonas* species 6307 (AATCC® 21439) (Mr=48 kDa) was demonstrated to be highly specific for secondary alcohols and exhibited no activity with primary alcohols. It was also shown that this enzyme was largely not inhibited in the presence of high concentrations of ethanol (0% and 30% inhibition in the presence of 10 mM and 100 mM ethanol, respectively). S-ADH from *T. Brockii* (Mr=40 kDa) exhibits very similar substrate specificity to S-ADH from *Xanthobacter* with the exception that it prefers NADPH rather than NADH. Of note is that S-ADH from *T. brockii* is one of the few S-ADH enzymes that has been cloned and sequenced (Genbank accession number A32973). Other available S-ADH enzymes (S-ADHs) include S-ADH from *Candida parapsilos*, as described in U.S. Pat. No. 5,763,236; the sequence available in Genbank, under Accession No. AB010636; S-ADH from *Thermoanaerobacter ethanolicus* 39E (ATCC® 33223) (Genbank Accession No. U49975); and S-ADH from *Clostridum beijerinckii* (Genbank accession number M84723). Comparatively, five of the first 15 amino acid residues of the N-terminal amino acid sequence (M, K, G, G and K) of S-ADHs from *T. brockii* and *T. ethanolicus* (both enzymes have identical N-terminal sequences) match the N-terminal sequence of S-ADH from *X. autotrophicus* st. Py2 (MKGLVYRGPGKKALE SEQ ID NO:7).

It is apparent from the literature that there may be many S-ADH enzymes that are specific for acetone. Such S-ADH enzymes could be incorporated into a biosensor. In addition to these, culture collection strains and several new strains that were isolated from soil by enrichment on acetone, isopropanol, or propane as growth substrates were found to exhibit S-ADH activity (data not shown). In order to compare and evaluate relative specificities among these S-ADH activities, purified S-ADH from *Xanthobacter* and partially purified preparations of, or cell extracts containing, S-ADHs from isopropanol-grown bacterial strains (TDCC IP-1 (and two additional strains: data not shown)), propane-grown M vaccae JOB-5, and *T. brockii* S-ADH were assayed with various ketone and alcohol substrates. As shown in Table 5, S-ADH enzymes from *X. autotrophicus* Py2, strain IP-1, *M. vaccae* JOB-5, and *T. brockii* all demonstrated negligible or substantially lower activity with primary alcohol substrates. Although the S-ADH reaction equilibrium for acetone monitoring will be shifted for acetone reduction (that is NAD(P)H in excess), low specificity for primary alcohols, mainly ethanol, is preferred to alleviate possible inhibitory effects. All of the enzymes were active using longer-chain ketones (that is 2-butanone, 2-pentanone, and 3-pentanone) however this should be of little consequence since these compounds are not normally found on human breath. Interestingly, S-ADH from *T. brockii* was more active with shorter chain ketones, which contrasts the activity of S-ADH from *Xanthobacter* which was more active with longer chain ketones. It should be noted that the *T. brockii* S-ADH is a commercially available S-ADH (Sigma). The application of this enzyme in a biosensor according to the invention will be discussed in more detail below. Thus, the *X. autotrophicus* S-ADH enzyme isolated as described above represents a unique enzyme that enables the relatively selective detection of longer chain ketones in mammalian samples via the coupled enzyme system of the invention.

TABLE 5

Substrate Specificities of Bacterial Secondary Alcohol Dehydrogenases.

| | Relative S-ADH Activity (%) of Bacterial Strains | | | | |
|---|---|---|---|---|---|
| Substrate | X. Py2 | IP-1 | JOB 5 | T. brockii | C. boidinii[e] |
| Acetone[a] | 100 | 100 | 100 | 100 | 100 |
| 2-Butanone | 170 | 192 | 213 | 67 | 175 |
| 2-Pentanone | 198 | 44 | 185 | 59 | 16 |
| 3-Pentanone | 180 | 5 | 26 | 49 | 60 |
| Acetone/Ethanol[b] | 100 | 98 | 98 | 100 | 88 |
| 2-Propanol[c] | 100 | 100 | 100 | 100 | 100 |
| Ethanol | NA[d] | 9 | NA | NA | 9 |
| 1-Propanol | NA | 2 | 9 | NA | 9 |
| 1-Butanol | 7 | 2 | 10 | NA | 6 |
| 2-Butanol | 88 | 147 | 130 | 121 | 100 |
| 1-Pentanol | NA | NA | NA | NA | 8 |
| 2-Pentanol | 157 | 18 | 68 | 38 | 22 |

[a]Ketone reduction rates calculated in duplicate at pH 6.2 with 2.5 mM substrate and 0.2 mM NADH (NADPH for *T. brockii* assays).
[b]Acetone reduction rates calculated in duplicate at pH 6.2 in the presence of an equivalent amount of ethanol (2.5 mM).
[c]Alcohol oxidation rates calculated in duplicated at pH 7.6 with 2.5 mM substrate and 0.2 mM NAD[+] (NADP[+] for *T. brockii* assays).
[d]NA, no activity detected.
[e]Ketone reduction rates and alcohol oxidation rates calculated at pH 7.6 with 5 mM substrate and 0.2 mM NADH or NAD[+].

Figure 6:
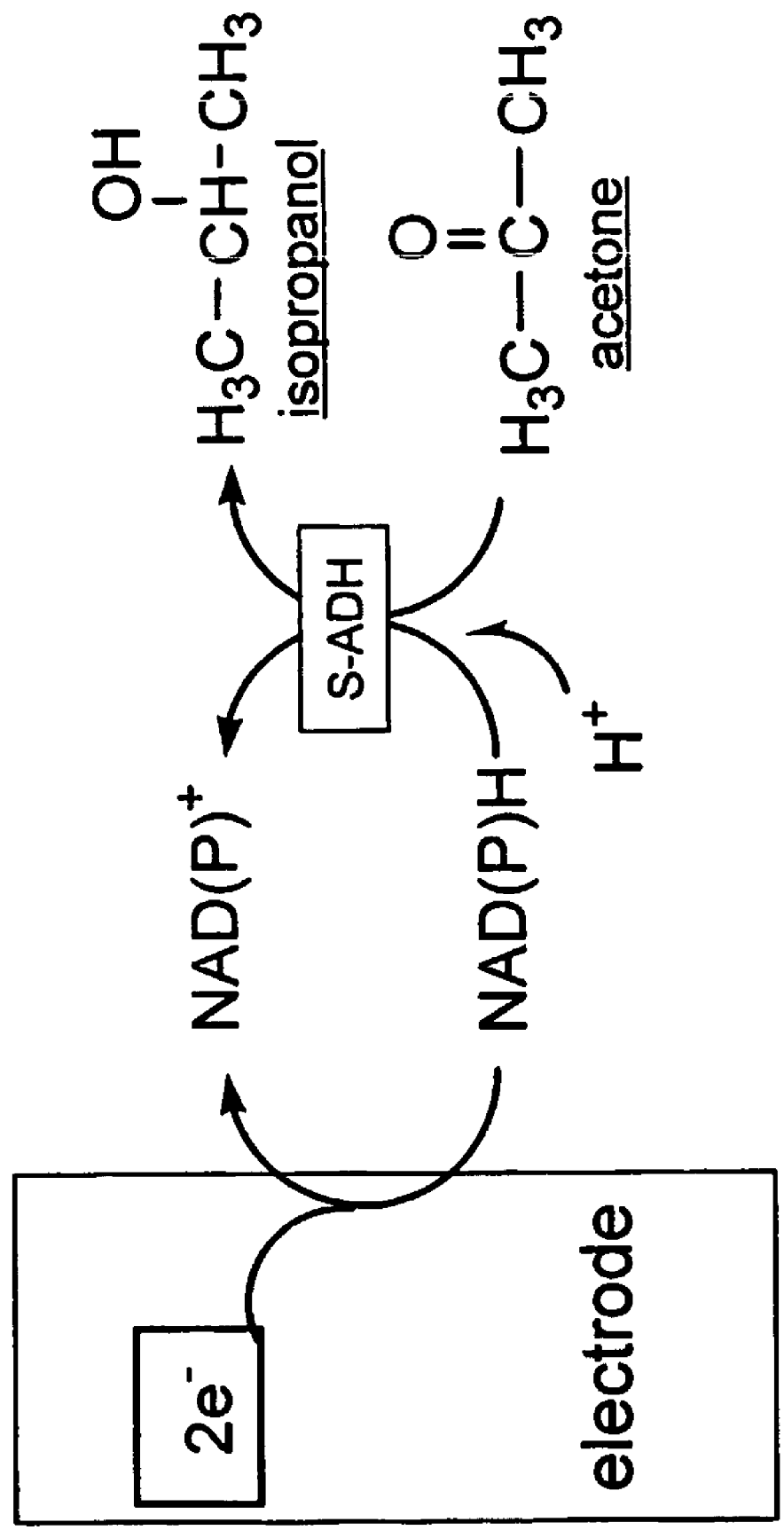
FIG. 6 is a schematic depiction of an acetone electrochemical sensor using S-ADH. S-ADH was determined to have protein N-terminus of SEQ ID NO: 7.
Figure 7:
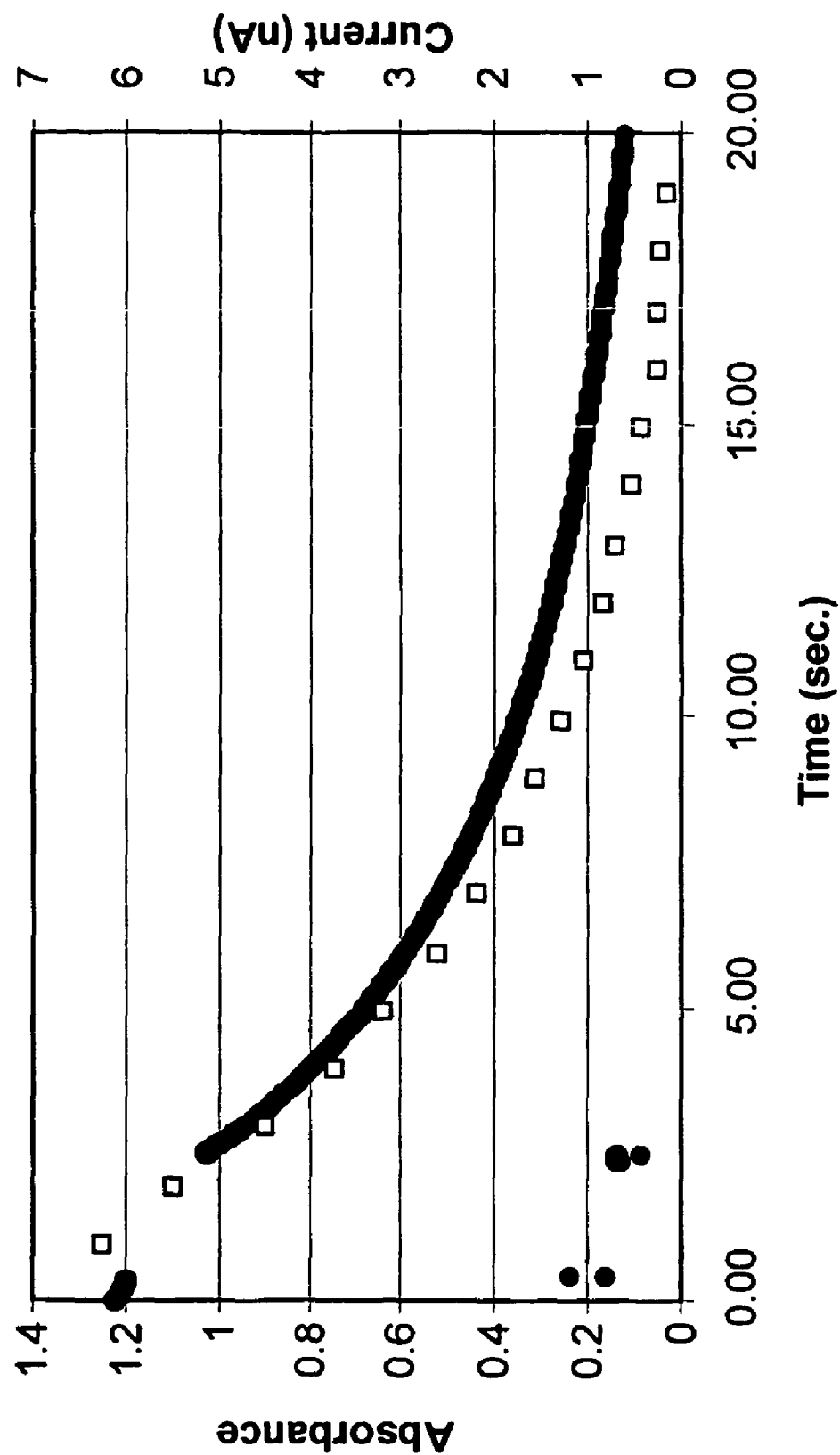
FIG. 7 graphically shows a correlation of electrochemical response (□) and UV spectrophotometric response (●) data of S-ADH-catalyzed reaction. S-ADH was determined to have protein N-terminus of SEQ ID NO: 7.
Figure 8:
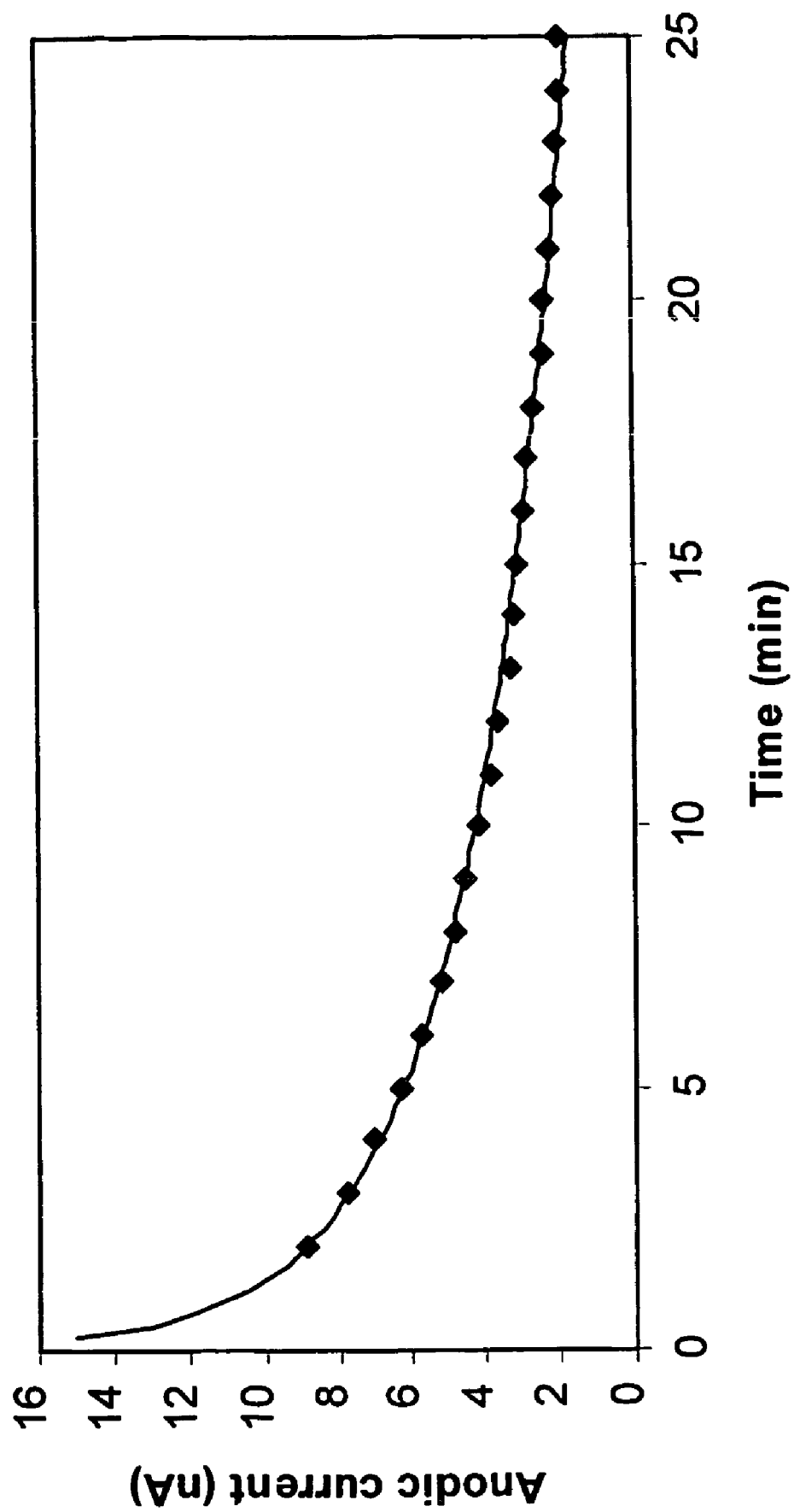
FIG. 8 graphically depicts electrochemical detection of acetone-dependent oxidation of NADH catalyzed by S-ADH from *X. autotrophicus* Py2. S-ADH was determined to have protein N-terminus of SEQ ID NO: 7.

Monitoring of the S-ADH reaction electrochemically. Electrochemical transduction of enzyme-substrate interactions provides a general analytical means to detect the respective substrate. As previously described, dehydrogenase-based enzyme reactions typically require the pyridine nucleotide cofactors NADH or NADPH in stoichiometric amounts for catalysis. A number of biosensors have been described in the art which rely on electrochemical detection of these coenzymes. As shown in FIG. 6, operating in a manner similar to other biosensors, electrochemical detection of NAD(P)H consumption would allow the conjugation of an electrode and an S-ADH catalyzed reaction, providing a means to quantify acetone in a substrate-specific fashion. In order to validate the scheme shown in FIG. 6, fast-scan cyclic voltammetry (sweeping rate >100 V/s) was performed using a carbon microelectrode to measure the acetone-dependent consumption of NADPH catalyzed by S-ADH from *T. brockii*. Electrochemical detection of acetone-dependent oxidation of NADPH catalyzed by *T. brockii* S-ADH was measured by performing continuous voltammetric scans of the enzyme reaction mix. These scans demonstrated changes in the anodic peak area over time, which were dependent upon the addition of acetone. The anodic current decreased versus time indicating that NADPH was being consumed (oxidized) as S-ADH catalyzed the reduction of acetone to isopropanol. Scans were performed from about 1200 mV to 0 mV and anodic current was measured; data for 19 scans were obtained at one-minute intervals. The initial current (at about 1200 mV) for each scan varied regularly, with about −6.5 nA being measured at 1 minute and about −0.2 nA at 19 minutes. For each scan, a significant current ceased (and about 0 nA was measured thereafter), by about 600 mV. In order to further confirm that NADPH consumption was being accurately measured, the reaction was monitored both electrochemically and spectrophotometrically under identical reaction conditions. As shown in FIG. 7, response data obtained using both detection methods were in close agreement to each other confirming that the acetone-specific, NADPH-dependent S-ADH reaction can be monitored electrochemically with accuracy. The voltammetric scanning procedure used to test *T. brockii* S-ADH was repeated using S-ADH from *X. autotrophicus* Py2 to ensure that an NADH-dependent S-ADH reaction could be monitored electrochemically. As with the NADPH-dependent enzyme, continuous scans of the reaction mix containing S-ADH from *X. autotrophicus* Py2 yielded an acetone-dependent decrease in anodic current over time corresponding to the enzyme-catalyzed oxidation of NADH, as shown herein in FIG. 8.

Figure 9:
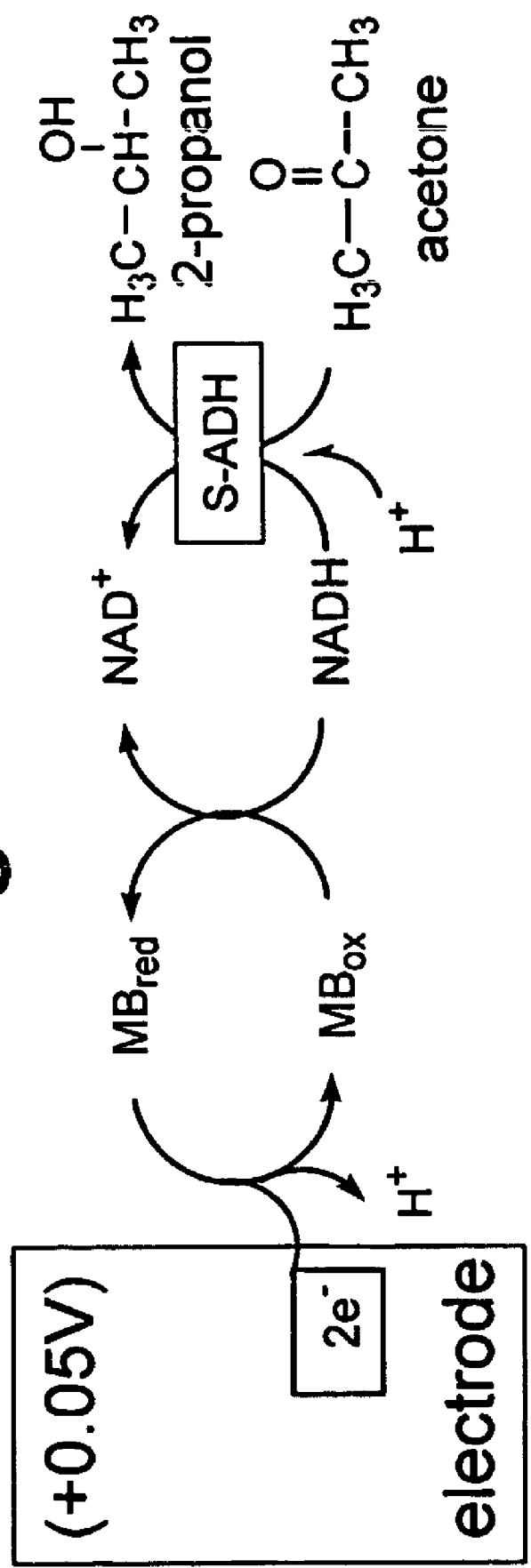
FIG. 9 schematically depicts electrochemical detection of acetone-dependent oxidation of NADH catalyzed by S-ADH from *X. autotrophicus* Py2 using a carbon electrode modified with the mediator Meldola's Blue (MB). S-ADH was determined to have protein N-terminus of SEQ ID NO: 7.

The electrochemical detection of the NAD(P)H-dependent S-ADH reaction as described above provides the necessary fundamental analytical means to implement certain design criteria to the enzyme-electrode structure. In general, dehydrogenase-based biosensors described in the art are comprised of a conductive electrode coated with a mixture, or layers, of a catalytically enzyme(s) and a mediator compound. When the coated electrode is contacted with a sample containing the substrate for which the enzyme(s) exerts a catalytic effect, the mediator compound transfers charge to the electrode to give a readout signal against a reference electrode. The active electrode is preferably formed of conductive carbon that can formulated into screen-printable ink or other formulations/compositions that enable low-cost manufacturing methods and end-use disposability. Mediator compounds described in the art specific for NAD(P)H include viologen derivatives, quinone derivatives, phenazine, osmium phendione, thionine, alizarin green, and Meldola's Blue (Katakis & Dominguez, Mikrochim. Acta 126:11-32 (1997)). Mediators, as mentioned previously, improve the overall sensitivity of the electrode by enhancing NAD(P)H electrooxidation kinetic rates at reduced potentials. The feasibility of using the mediator Meldola's Blue (MB) for detecting the S-ADH reaction electrochemically (as shown in FIG. 9) was investigated.

Figure 10:
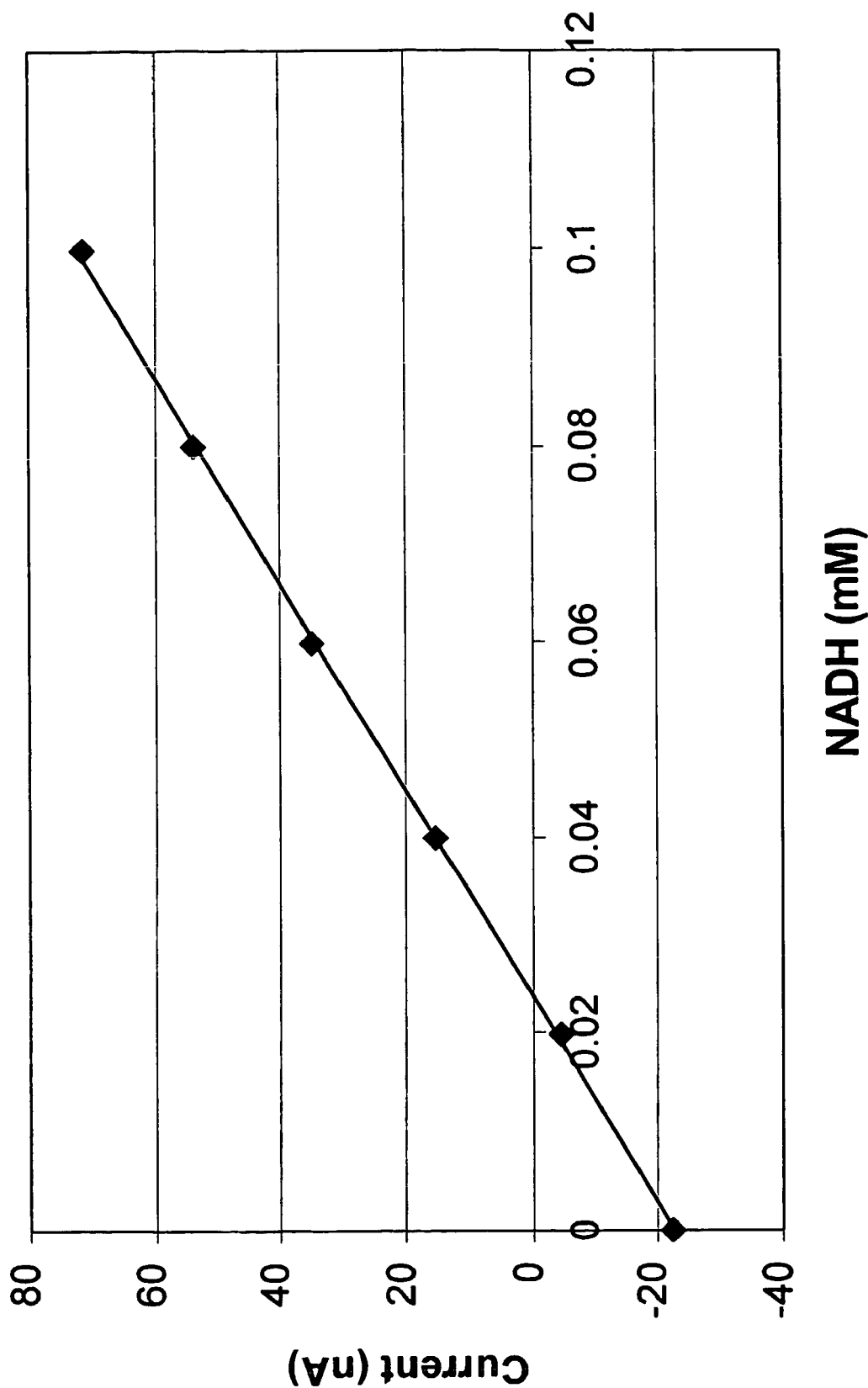
FIG. 10 graphically presents the results of an electrochemical assay of NADH concentration using a glassy carbon electrode modified with Meldola's Blue.
Figure 11:
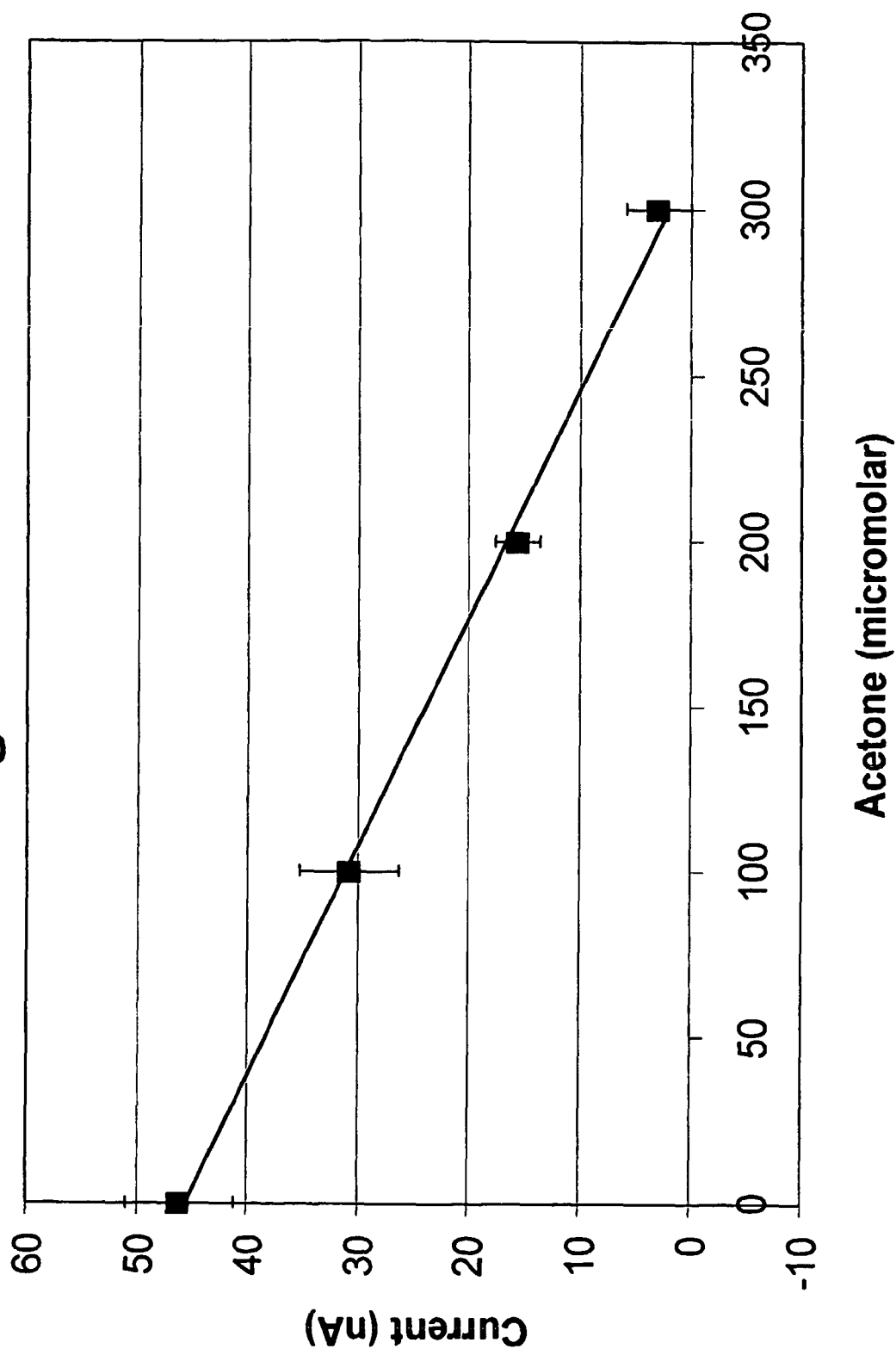
FIG. 11 graphically presents the results of an electrochemical assay of acetone-dependent NADH consumption catalyzed by S-ADH using a Meldola's Blue modified screen-printed carbon electrode MB-SPCE.

Chronoamperometry was performed using a glassy carbon electrode with absorbed Meldola's Blue to measure NADH concentration. As shown in FIG. 10, the current response using the modified electrode is linear with respect to the concentration of NADH present. This linearity was also tested and determined up to 1 mM NADH (data not shown). Since the consumption of NADH is proportional to the concentration of acetone (that is the reaction catalyzed by the S-ADH), these results demonstrate that Meldola's Blue modified carbon electrode provides a mediated electrode system for quantifying of acetone. As a means to investigate this further and to permit the construct a practical, disposable acetone biosensor, chronoamperometry experiments were performed using screen-printed carbon electrodes impregnated with the mediator Meldola's Blue (hereinafter "MB-SPCE"). Shown in FIG. 11 is the response data of the acetone-dependent S-ADH reaction obtained using MB-SPCE disposable electrode strips. The correlation coefficient ($R^2$) of the acetone response was 0.965 and the electrode-to-electrode reproducibility was approximately 6%. These data confirm that the acetone-specific enzyme system can be monitored electrochemically using a practical electrode system.

Figure 12:
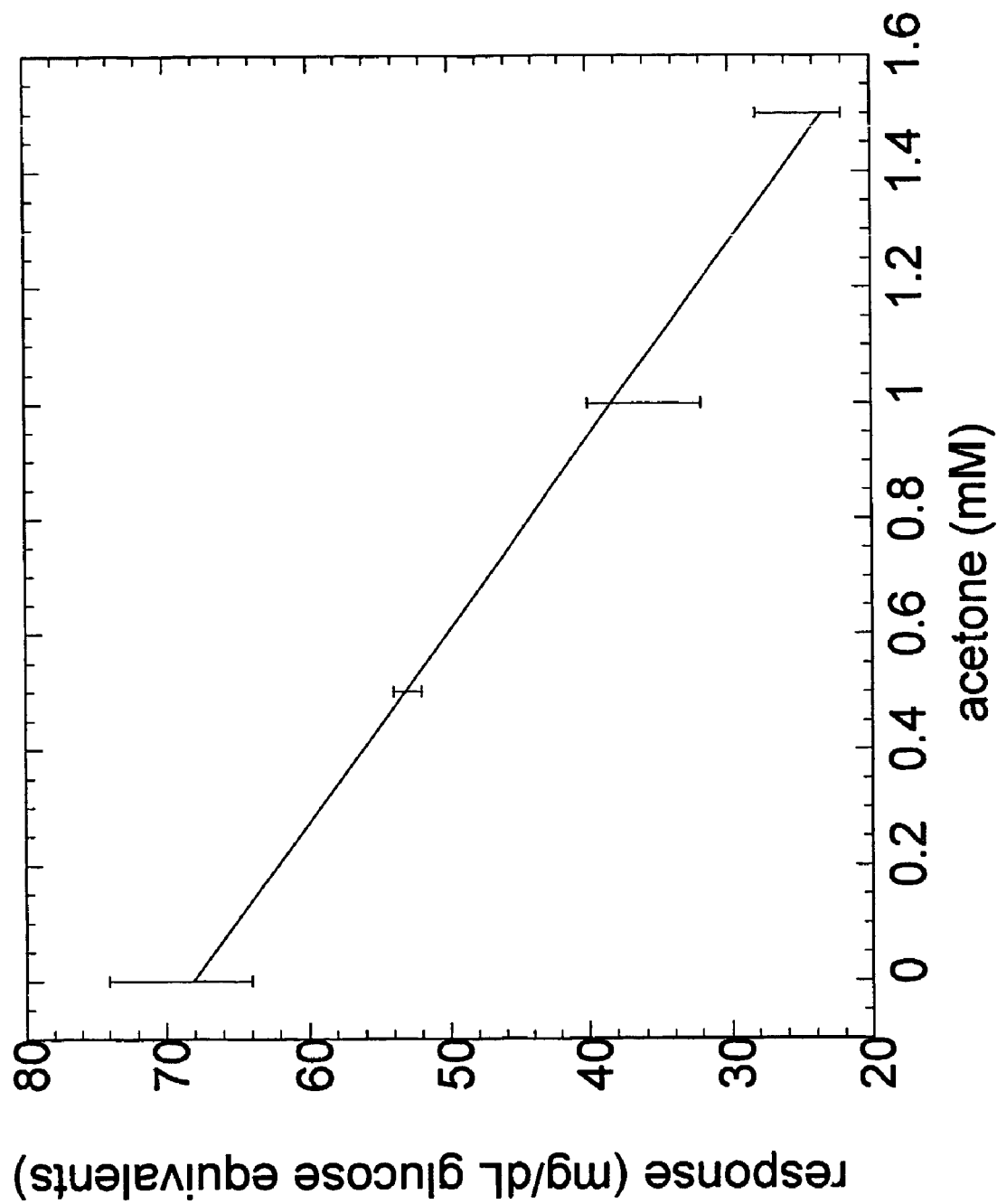
FIG. 12 graphically presents the results of an electrochemical assay of acetone-dependent NADH consumption catalyzed by S-ADH using a glucose commercial test strips and monitor.

A practical device for acetone measurement was devised in which acetone-dependent NADH consumption was monitored. This device employed a commercially available, disposable, glucose biosensor system (a blood glucose monitor known to register NADH concentration, and blood glucose test strips produced for use therewith, both manufactured by MediSense, Inc., Abbott Laboratories, Bedford, Mass.) to measure NADH consumption catalyzed by S-ADH in response to acetone. Shown in FIG. 12 are the results, demonstrating acetone-dependent NADH consumption measured by the portable monitor and disposable test strips. This demonstrates the feasibility of constructing a practical device for acetone measurement that uses mass-produced electrodes and monitors to register and/or record currents for an acetone-specific enzyme system.

In contrast to electrochemically monitoring the S-ADH reaction by following NAD(P)H consumption, it is also possible to monitor NAD(P)$^+$ formation electrochemically by measuring an increase in the cathodic current density at a voltage that would be directly proportional to NAD(P)$^+$ concentration. The disadvantage of this detection scheme is that oxygen often gives a strong interference response at the negative voltage potentials required for electrochemical reduction of NAD(P)$^+$. In addition, electroreducing NAD(P)$^+$ forms radicals that dimerize, resulting in fouling of the enzyme electrode. For these reasons, electrochemical experiments involving electrochemical regeneration of NAD(P)$^+$ are often performed anodically with electron transfer mediators that shift voltage potentials away from interfering peaks. However, these options in the context of an acetone biosensor may not be practical without further modification, since oxygen is always present in human breath.

Figure 13:
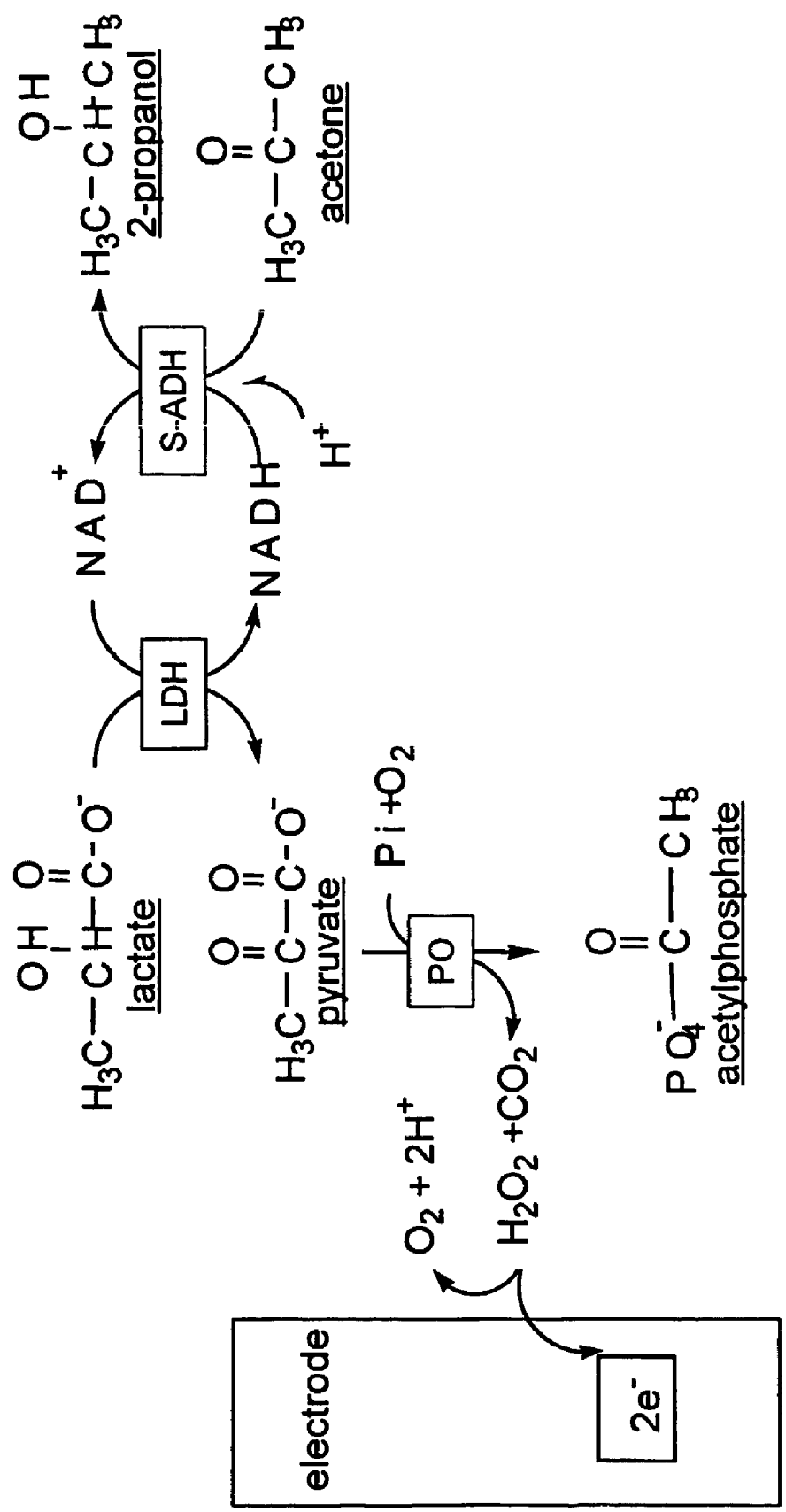
FIG. 13 is a schematic of electrochemical detection of S-ADH reaction coupled to H$_2$O$_2$ formation specifically showing S-ADH coupled to lactate dehydrogenase (LDH) and pyruvate oxidase (PO).
Figure 14:
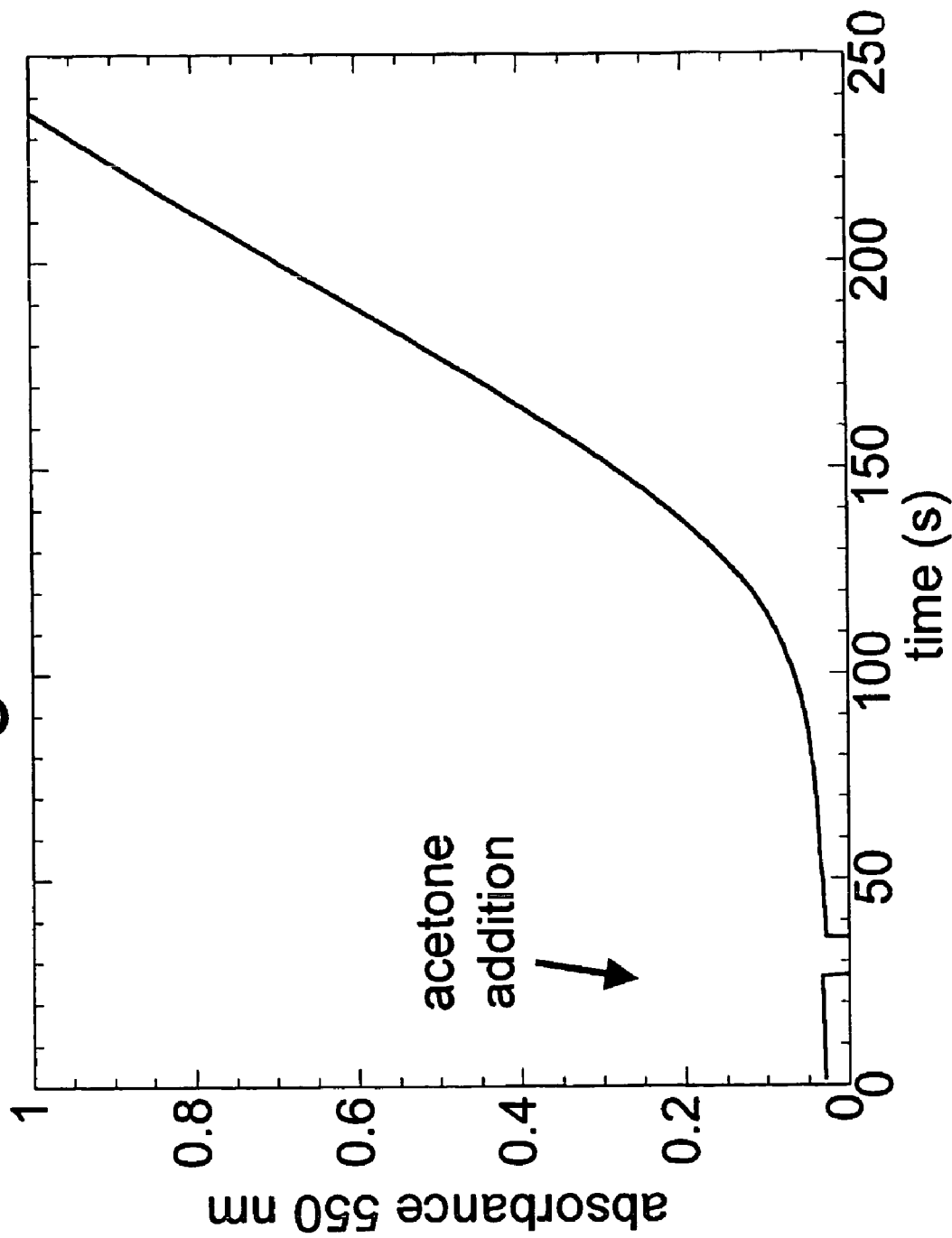
FIG. 14 graphically depicts acetone-dependent H$_2$O$_2$ formation using S-ADH coupled enzyme system.

One alternative to monitoring NAD(P)$^+$ formation is to indirectly couple other enzyme activities to the S-ADH enzyme reaction. As shown in FIG. 13, NAD(P)$^+$ formation can be coupled to lactate dehydrogenase catalysis to form pyruvate. Pyruvate is then oxidized, by pyruvate oxidase, to produce acetylphosphate and $CO_2$, with concomitant formation of $H_2O_2$. $H_2O_2$ is then electrochemically oxidized and detected at the electrode by any of the methods well-known in the art. In this scheme, the acetone-dependent formation of NAD(P)$^+$ (catalyzed by S-ADH) is indirectly coupled to $H_2O_2$ production. In order to investigate the coupling between these enzyme reactions, this reaction mix (containing coupling enzymes and reagents) was prepared with NADH-dependent S-ADH from *X. autotrophicus* Py2 in the presence of horseradish peroxidase (HRP). HRP catalyzes the reduction of $H_2O_2$, and the oxidation of electron donors (chromogenic dye reagents), thereby permitting the reaction to be monitored spectrophotometrically. FIG. 14 illustrates the results of the coupling reactions, where an increase in absorbance was observed upon addition of acetone that corresponded to $H_2O_2$ formation. The lag time required for the coupled reactions to reach a steady state was further shortened to less than 20 s by further optimization of the reaction conditions (data not shown). The coupling reaction was modified for NADPH-dependent S-ADH from *T. brockii* by replacing lactate dehydrogenase with malic enzyme. Malic enzyme is NADP$^+$-dependent and catalyzes the oxidation and decarboxylation of malate to form pyruvate. Pyruvate, as described above, is further oxidized by pyruvate oxidase to form $H_2O_2$. In this case, NADP$^+$ formation is indirectly coupled to $H_2O_2$ production. Using this coupled enzyme system, a background increase in absorbance was observed that was not acetone-dependent (data not shown). However, approximately a 5-fold increase in the rate of $H_2O_2$ formation over the background rate was observed after addition of acetone. (The small, background rate of $H_2O_2$ formation (acetone independent) may be due to NADPH oxidase (diaphorase) activity catalyzed by malic enzyme.) The pyridine-nucleotide dependency of lactate dehydrogenase and malic enzyme in the respective, coupled S-ADH reactions (that is S-ADH from *X. autotrophicus* is NADH-dependent and is coupled to NADH-dependent lactate dehydrogenase; and S-ADH from *T. brockii* is NADPH-dependent and is coupled to NADPH-dependent malic enzyme) may be interchanged by using site-directed mutagenesis to alter the specificity of these coupling enzymes for NADH or NADPH (Holmberg et al., Protein Eng. 12(10): 851-6 (1999)). Alternatively, naturally occurring homologs of lactate dehydrogenase or malic enzyme may be used that have relaxed specificity for NADH and NADPH (B. I. Lee et al., J Mol. Biol. 307(5):1351-62 (2001)).

Figure 15:
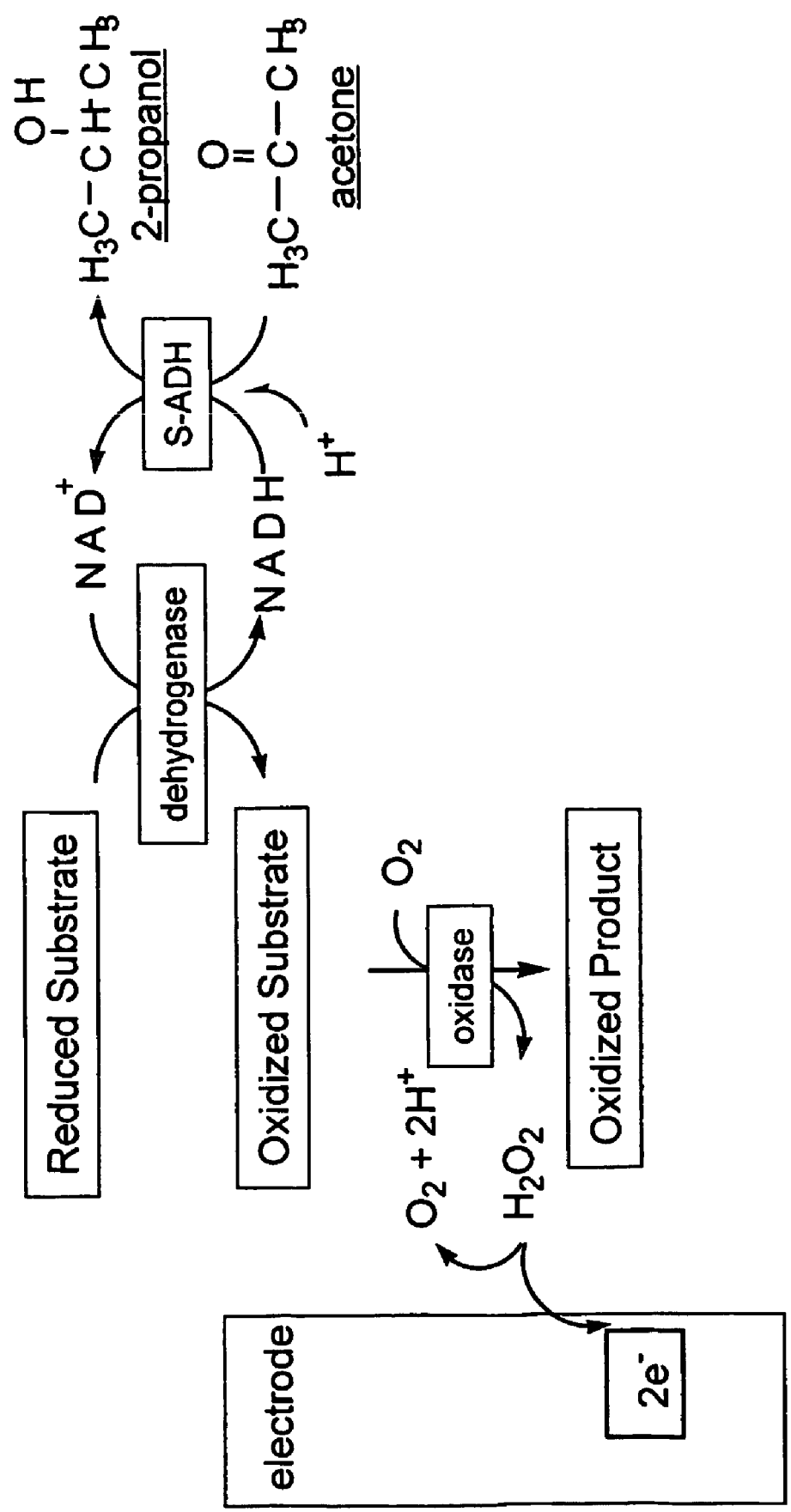
FIG. 15 is a schematic illustrating a general scheme for coupling S-ADH reaction to H$_2$O$_2$ formation.

Besides the two, coupled S-ADH enzyme systems described above, other coupled enzyme systems can also be usefully employed in an acetone-specific enzyme system according to the present invention. In the scheme shown in FIG. 15, S-ADH catalyzes acetone reduction, forming NAD (P)$^+$, which is then reduced back to NAD(P)H by the appropriate pyridine nucleotide dependent dehydrogenase (NADH- or NADPH-specific, depending on the cofactor requirement of the S-ADH). The oxidized product of the dehydrogenase reaction is then the substrate for an oxidase, which generates $H_2O_2$ by oxidizing the molecule further. Other enzymes that can be employed in this coupling scheme include, but are not limited to: alanine dehydrogenase (EC 1.4.1.1), which catalyzes the NAD$^+$-dependent formation of pyruvate, which is then oxidized by pyruvate oxidase; saccharopine dehydrogenase (EC 1.5.1.7), which catalyzes the NAD$^+$-dependent formation of lysine, which is then further oxidized by lysine oxidase (EC 1.4.3.14) to form $H_2O_2$; malic dehydrogenase (EC 1.1.1.37), which catalyzes the NAD$^+$-dependent formation of oxalacetate, which is decarboxylated by oxalacetate decarboxylase (EC 4.1.1.3) to pyruvate, pyruvate then being further oxidized by pyruvate oxidase to form $H_2O_2$; and glycerol dehydrogenase (EC 1.1.1.6), which catalyzes the NADtdependent formation of dihydroxyacetone, which is then further oxidized by galactose oxidase (EC 1.1.3.9) to methylglyoxal. Of these, alanine dehydrogenase was tested in an enzyme coupling scheme to verify that such alternative coupling schemes would function in tandem with S-ADH, wherein alanine dehydrogenase in used in place of lactate dehydrogenase. Using this alternative enzyme scheme, an increase in absorbance was observed upon addition of acetone that corresponded to $H_2O_2$ formation (data not shown).

Non-Electrochemical Monitoring of the S-ADH Reaction Coupled to $H_2O_2$ Formation.

Figure 16:
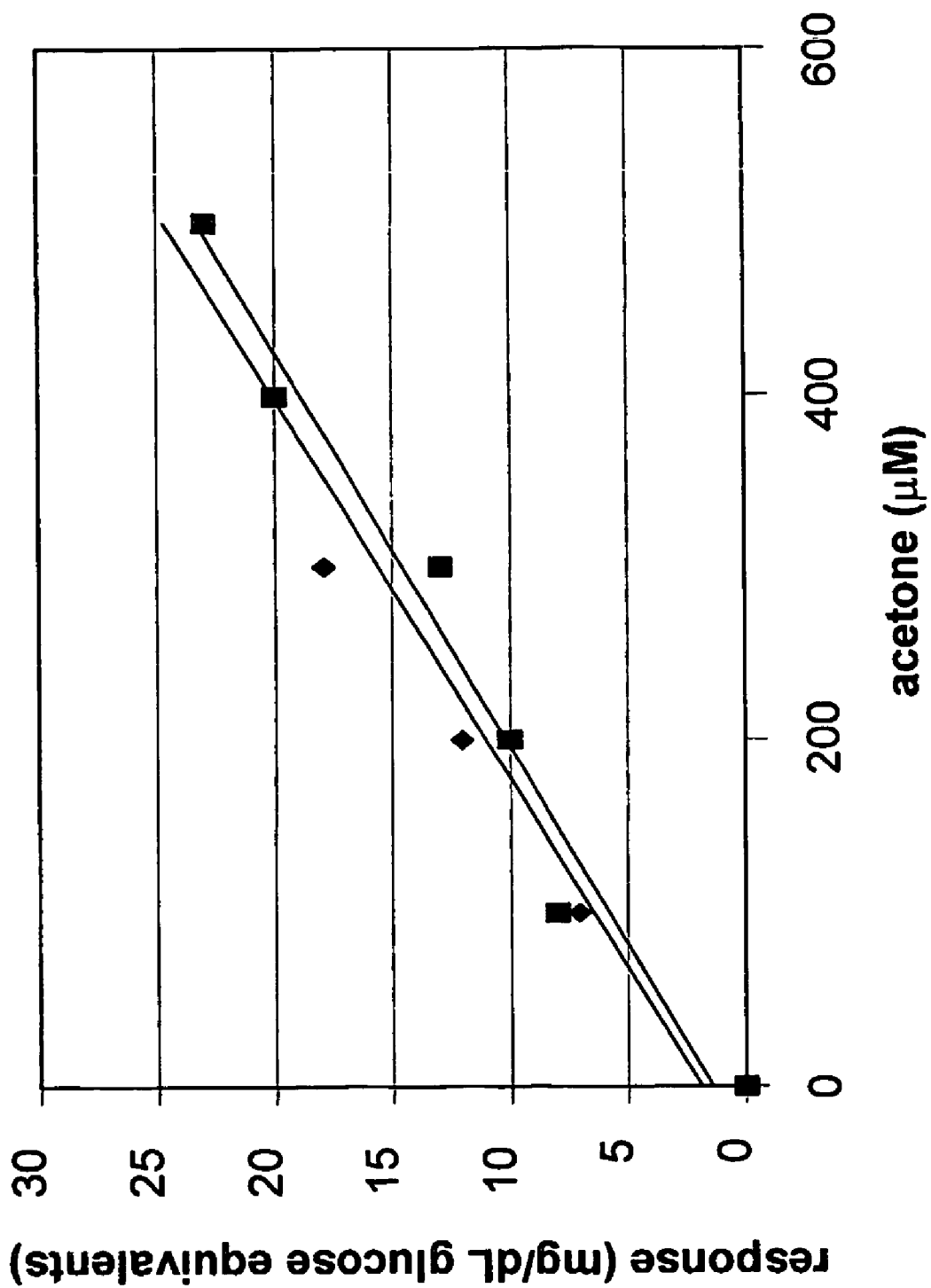
FIG. 16 graphically depicts the results of a reflectance photometry assay of acetone-dependent H$_2$O$_2$ formation using S-ADH coupled enzyme system using glucose test strips and monitor.

It may also be possible to construct a practical device for non-electrochemical acetone measurement. To investigate whether a practical, non-electrochemical device could be prepared for measuring acetone by means of an acetone-specific, coupled enzyme system, a device was constructed in order to measure acetone-dependent $H_2O_2$ formation. The device combined a blood glucose monitor and test strips manufactured for use therewith (both manufactured by Lifescan, Inc., Milpitas, Calif.) with an $H_2O_2$-producing system in which S-ADH catalysis of acetone was coupled to lactate dehydrogenase and pyruvate oxidase. In the device, the enzyme-catalyzed formation of $H_2O_2$ was coupled to peroxidase and dye reagents, which react to produce a colored reaction product when contacted with $H_2O_2$. The device then quantified the colored product by means of a reflectance photometry reader. Shown in FIG. 16 are the results, demonstrating acetone-dependent $H_2O_2$ formation measured by the portable monitor and disposable test strips. The monitor reading was the same whether acetone (♦) (linear regression of data gave y=0.0457x+1.9048) or an equivalent amount of $H_2O_2$ (■) (linear regression of data gave y=0.044x+1.3333) was added, indicating that the enzyme system did not interfere with the device reading and that the enzyme system was able to accurately catalyze the conversion of acetone to $H_2O_2$. This demonstrates the feasibility of constructing a practical non-electrochemical device for acetone measurement that uses mass-produced electrodes and monitors to quantitatively register and/or record reaction product concentrations for an acetone-specific enzyme system.

Electrochemical Monitoring of the S-ADH Reaction Coupled to $H_2O_2$ Formation.

Figure 17:
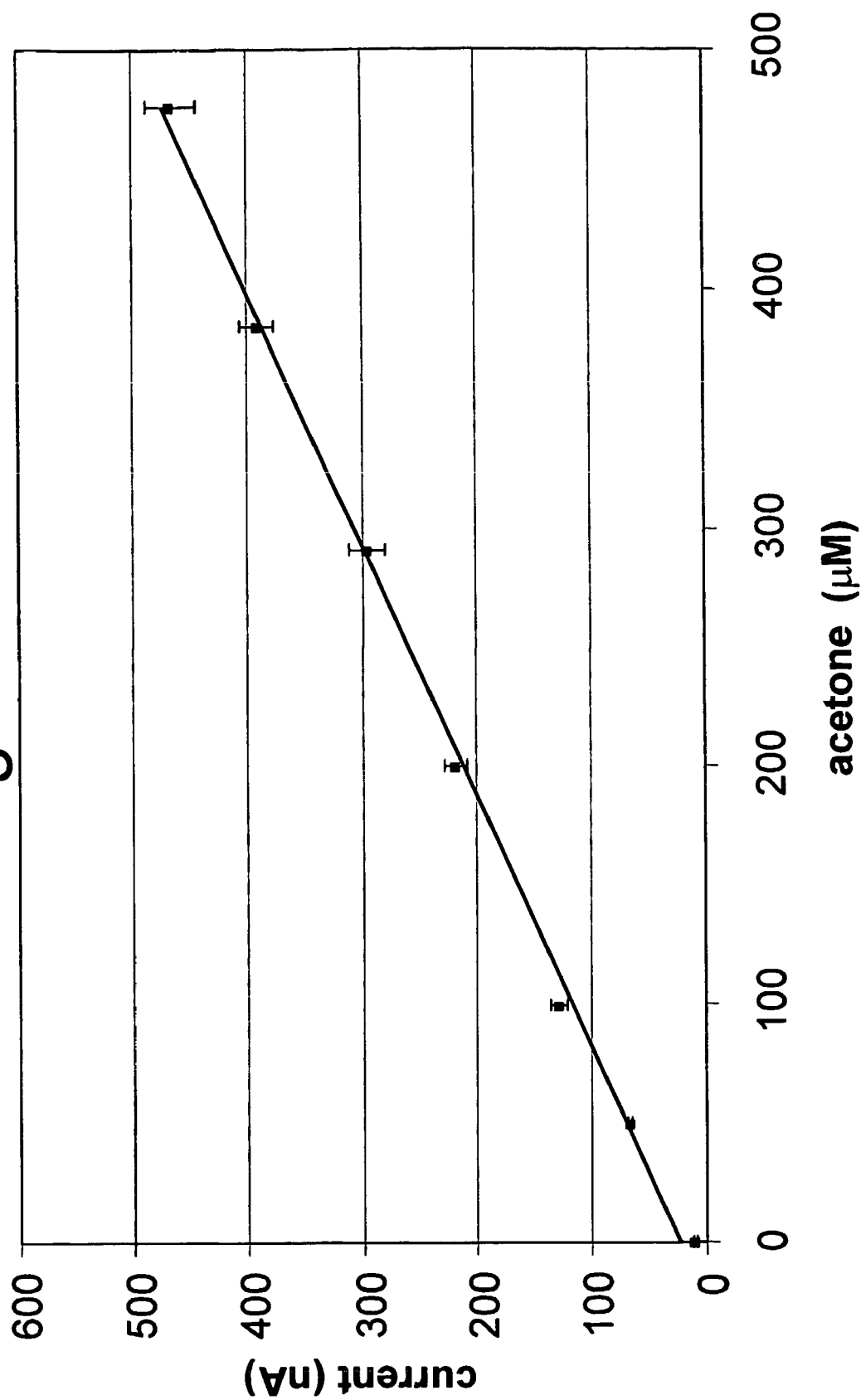
FIG. 17 graphically depicts the results of an electrochemical assay of acetone-dependent H$_2$O$_2$ formation using S-ADH coupled enzyme system using a disk platinum electrode.

Electrochemical detection of $H_2O_2$ has been well-studied for several years and has been applied in several commercial applications. Thus the enzyme system as described above (that is, S-ADH reaction coupled to $H_2O_2$ formation) represents a novel means to enzymatically monitor acetone using established electrochemical methodology. To this end, a disk platinum electrode was used to monitor the acetone-dependent formation of $H_2O_2$ catalyzed by the S-ADH coupled to lactate dehydrogenase and pyruvate oxidase, herein termed the "3-enzyme system", by using a chronoamperometric electrochemical method. FIG. 17 shows the acetone-dependent current response catalyzed by the 3-enzyme system. The currents correlate to acetone concentrations linearly with a correlation coefficient of 0.997 in the acetone concentration range of 0 to 200 μM. Eight individual sets of measurements were made, and the relative standard deviation (% CV, coefficient of variation) calculated to be less than 4% in the acetone concentration range of 10 to 200 μM. The method of detection limit (MDL), defined as 99% of the confidence limit, is 3.3 μM which is sufficiently sensitive enough for measuring the equivalent amount of gas-phase acetone in human breath. The experiment was repeated for higher acetone concentrations (up to 500 μM) with retention of linearity (correlation coefficient $R^2$=0.992) and reproducibility (CV=5% over entire concentration range; 8 measurements at each concentration) (data not shown).

Figure 18:
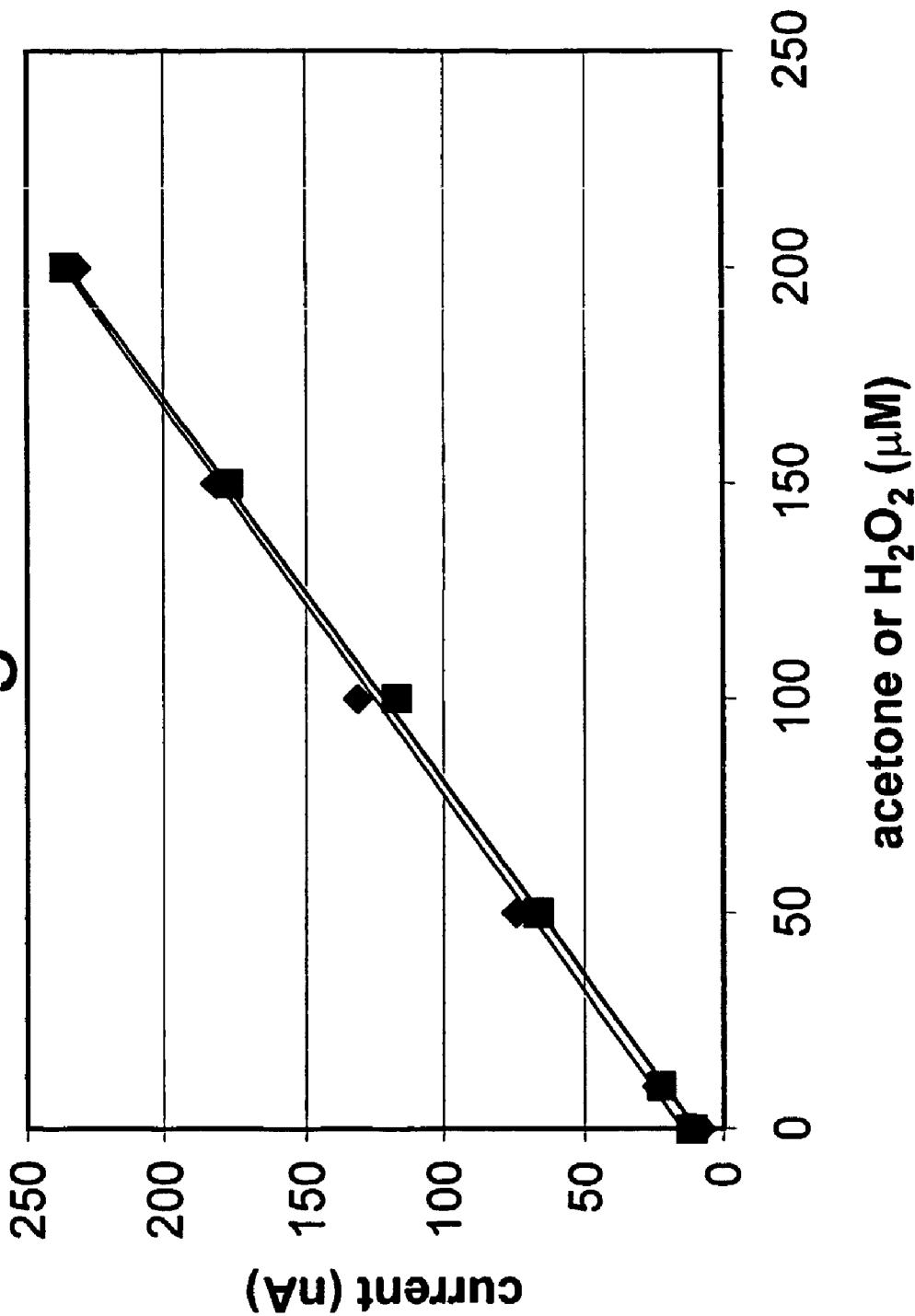
FIG. 18 graphically depicts the stoichiometric results of an electrochemical assay of acetone-dependent H$_2$O$_2$ formation using S-ADH coupled enzyme system.

The electrochemical assay results of the 3-enzyme system were directly compared with current responses to standard concentrations of $H_2O_2$ to determine whether the 3-enzyme system accurately converts acetone to $H_2O_2$. As shown in FIG. 18, the current response due to acetone addition (♦) or $H_2O_2$ addition (■) were nearly identical, with the linear regressions for acetone and $H_2O_2$ data gave near, identical equations of y=1.1213x+9.8416 and y=1.1161x+13.442, respectively. This indicates that the reaction is completed and that acetone is stoichiometrically converted to $H_2O_2$ by the 3-enzyme system.

Assays were performed as above, but in the presence of possible interference compounds. The current responses were measured for Acetone alone, as well as for Acetone plus 10 mM ethanol, Acetone plus 50 μM isopropanol, Acetone plus 50 μM isobutanol, Acetone plus 50 μM butanone, Acetone plus 50 μM pentanone (data not shown). The results demonstrate that ethanol, isopropanol and isobutanol do not interfere the acetone measurement. Notably, ethanol, which was present in 1000-fold excess (10 mM) of acetone, showed no inhibitory effect. Ethanol is a primary volatile metabolite present in human breath. The current responses for acetone in the presence of other ketones were increased according to the concentration of other ketone added, since the S-ADH does not discriminate among these ketone substrates (for example, a current response of 50 μM butanone is equivalent to 50 μM acetone) in the electrochemical assay. However, these other ketones are not found in human breath at significant levels therefore do not pose interference for the breath biosensor application.

As mentioned earlier for the electrochemical detection of acetone-dependent NADH consumption, the 3-enzyme system as described above provides the necessary fundamental analytical means to implement certain commercial design criteria. The active electrode is preferably formed of conductive carbon that can be formulated into screen-printable ink (that is, to form a strip electrode) or other formulations/compositions that enable low-cost manufacturing methods and end-use disposability. Toward these end-goals, a few low-cost electrode materials were evaluated with the 3-enzyme system as a means to demonstrate the commercial utility of this enzyme system for detecting acetone.

Figure 19:
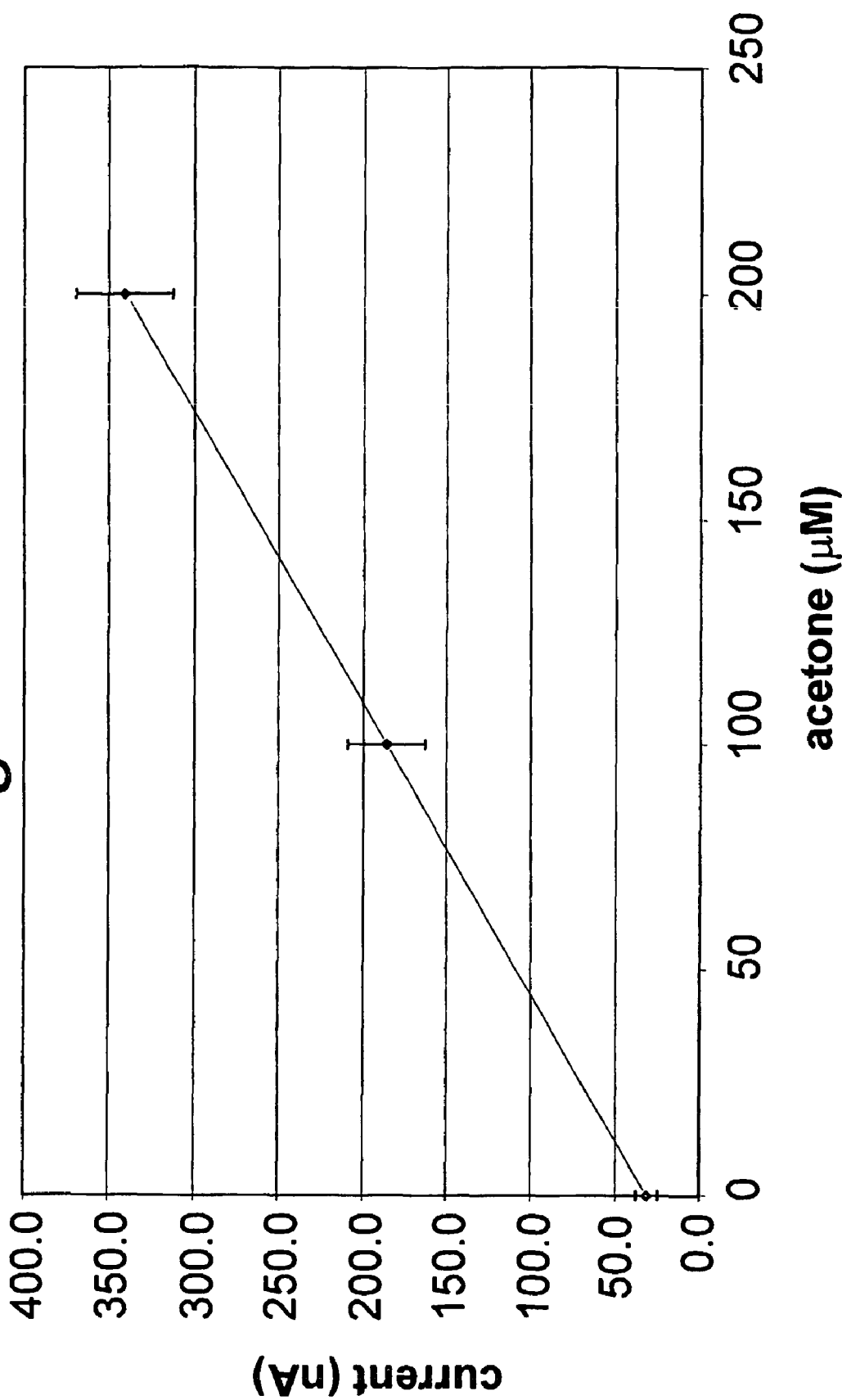
FIG. 19 graphically depicts the results of an electrochemical assay of acetone-dependent H$_2$O$_2$ formation using S-ADH coupled enzyme system using a disposable platinized carbon electrode.
Figure 20:
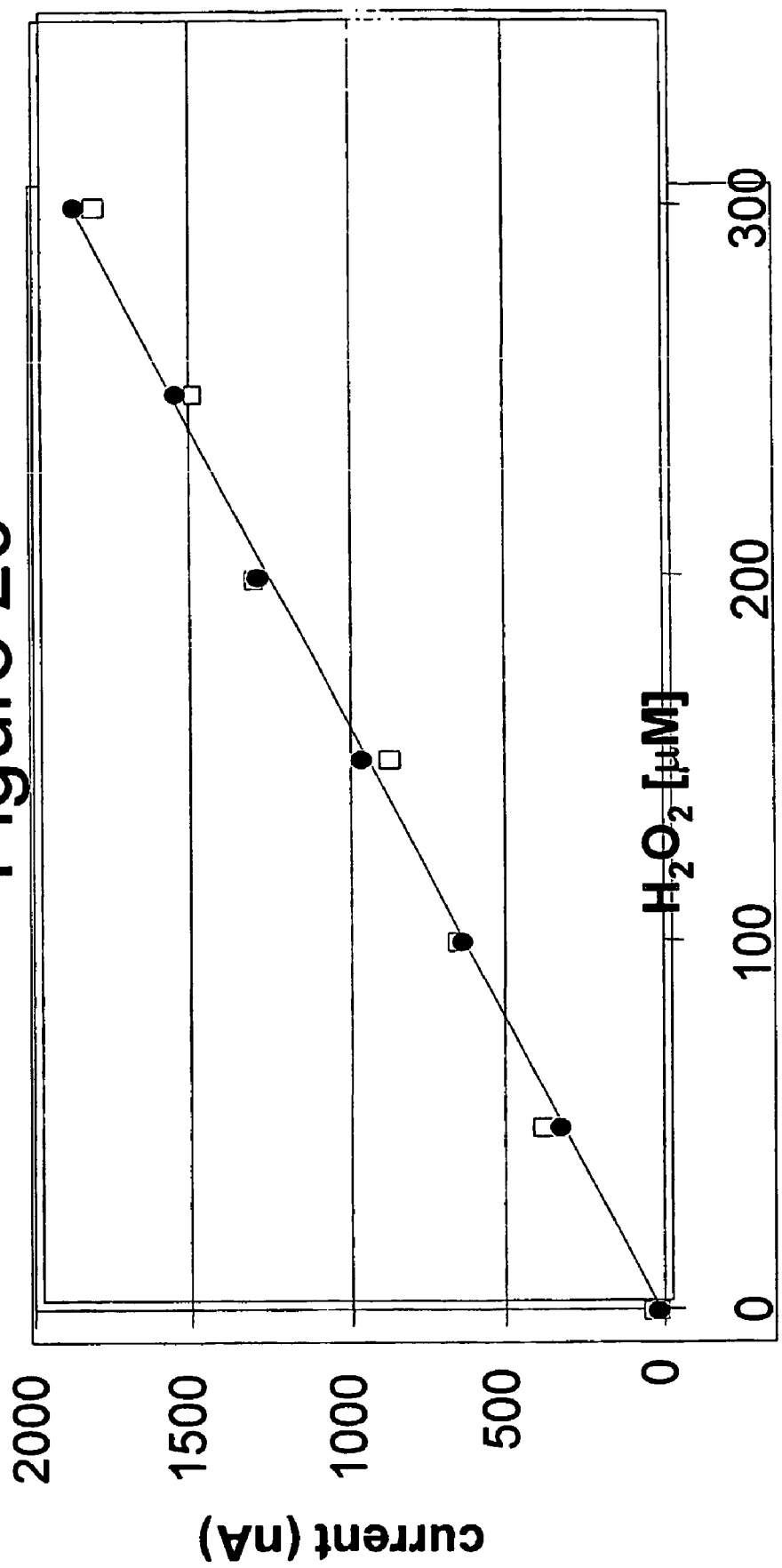
FIG. 20 graphically depicts the results of an electrochemical assay of acetone-dependent H$_2$O$_2$ formation using S-ADH coupled enzyme system using a disposable platinized carbon electrode.
Figure 21:
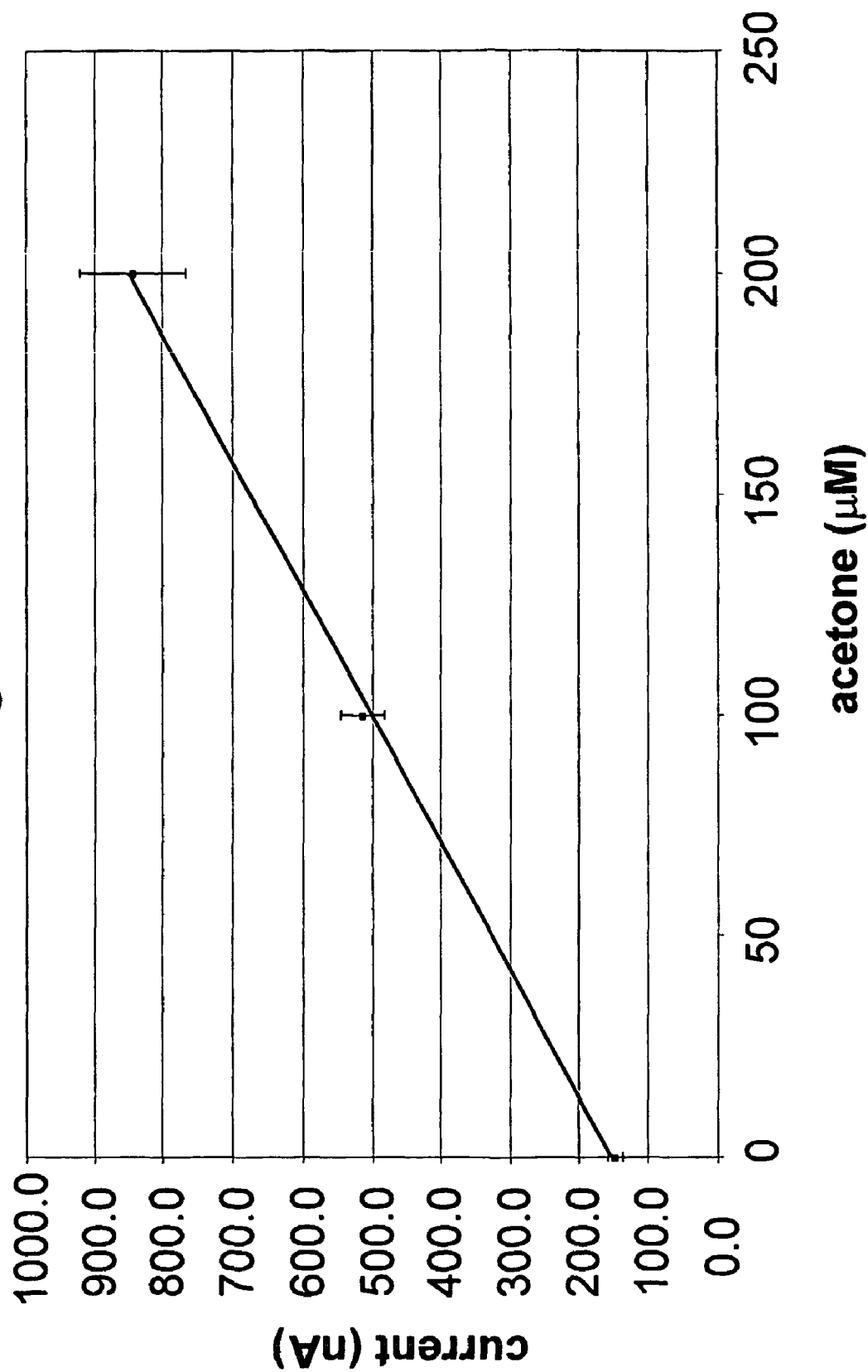
FIG. 21 graphically depicts the results of an electrochemical assay of acetone-dependent H$_2$O$_2$ formation using S-ADH coupled enzyme system using a disposable carbon electrode embedded with the mediator cobalt phtalolocyanine.

FIG. 19 shows current response vs. concentration acetone using a screen-printed platinized carbon electrode employed with the 3-enzyme system. The current responses correlated linearly to concentration of acetone present. The error bars were calculated based on eight measurements made using eight electrodes (single use). The reproducibility was dominated by electrode to electrode variation mainly due to the degree of wetting of the electrode surface. It was found that pre-wetting the electrode for 5 min improved the reproducibility significantly. Another material evaluated very similar to the screen-printed platinized carbon electrodes was a conductive carbon cloth or paper to which was bound highly conductive graphite particle loaded with platinum nanoparticles (10 to 20% (w/w) loading). The cloth or paper was hole-punched and attached to a screen-printed carbon electrode and used in conjunction with the 3-enzyme system for detecting acetone. FIG. 20 shows the electrode current response to $H_2O_2$ generated by acetone conversion by the 3-enzyme system (regression of data gives y=6.1601x+18.889). To aid in wetting the surface of this electrode, some electrodes were pre-treated with surfactants before use to reduce the hydrophobic nature of the graphite-Pt surface. It was determined this treatment aided in the wetting of the electrode surface while not pacifying the sensitivity of the electrode (data not shown). A third electrode evaluated using the 3-enzyme system was screen-printed carbon containing the mediator cobalt phthalocyanine. FIG. 21 presents the current response curve to acetone concentration using this electrode. An offset is shown due to the electrochemical response to NADH present in the 3-enzyme system. This effect was further investigated where current responses were recorded at the same applied voltage in the presence of different fixed concentrations of NADH (data not shown). Here it was determined that the cobalt phthalocyanine modified screen-printed carbon electrode electrodes were electroactive to NADH (at the potential for $H_2O_2$ measurement) and therefore the presence of high concentrations of NADH would interfere with acetone measurement. However, under the reagent conditions of the 3-enzyme system, the low concentration of NADH present offsets the current response in a fixed manner (constant) in which this can subtracted from the current response due to acetone ($H_2O_2$) without compromising the calibration accuracy. The results of this experiment demonstrate that platinum or platinized-carbon electrodes are not the only electrode materials that will function in detecting acetone-dependent $H_2O_2$ formation as catalyzed by the 3-enzyme system. Other screen-printed carbon electrodes modified with mediators for the purpose of detecting $H_2O_2$ include ferrocene and its derivatives, quinone and its derivatives, osmium bipyridine conjugated to poly(vinylpyridine), potassium hexacyanoferrate, nickelocene, methylene blue, methylene green, and phenazine methosulfate.

Figure 22:
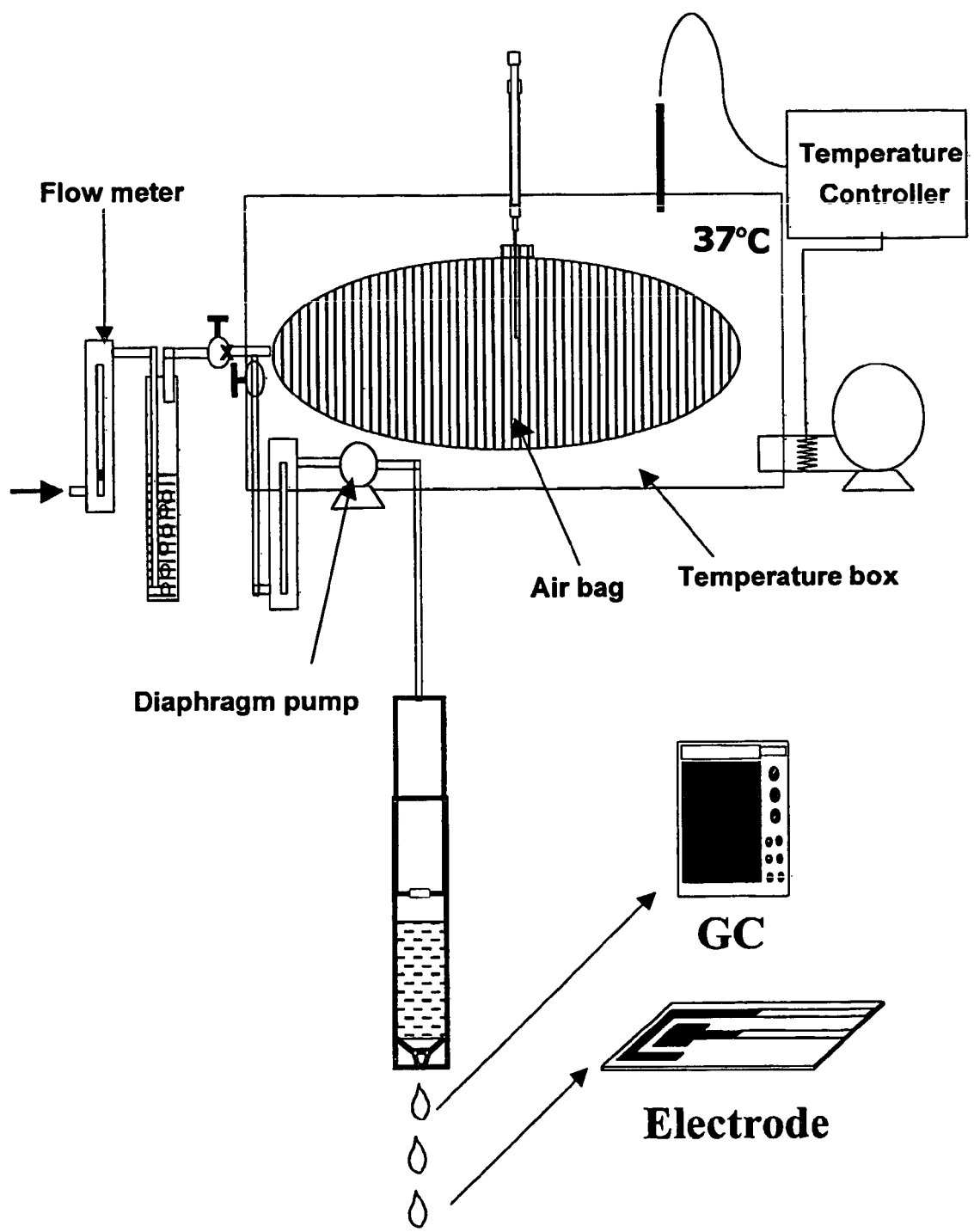
FIG. 22 schematically depicts the test gas sampling system employed to analyze acetone from synthetic breath.

Enzyme-based electrochemical measurement of gas-phase acetone. As mentioned previously, an important feature for the enzyme-based electrochemical sensor would be its ability to quantify gas-phase acetone concentrations. Since the enzyme electrode is responsive in the liquid phase alone, two sampling systems were investigated that would allow acetone gas to partition into the aqueous phase, thus allowing the sample to be directly or indirectly introduced to the enzyme-electrode system where a current response it then generated (proportional to the concentration of acetone present). The principle of both sampling systems (discussed in more detail below) follow Henry's Law constant for gas-liquid partitioning:

$$k_h = c_a \cdot p_g^{-1}$$

Where $k_h$ is Henry's Law constant for acetone (24 M·atm$^{-1}$, as reported by NIST (The National Institute of Standards and Technology)), $c_a$ is the concentration of acetone in the liquid phase (M), and $p_g$ is the partial pressure of acetone in the gas phase (atm). As a result, when gas-phase acetone samples are in contact with a liquid phase, the gas-liquid acetone concentration reaches equilibrium as expressed by Henry's Law. The concentration range of gas-phase acetone in human breath that needs to be quantified by the biosensor is 0.5-10 ppm (v/v). Therefore, under equilibrium conditions, 0.5-10 ppm (v/v) gas-phase acetone is equal to about 10 to 200 μM acetone in the aqueous phase. The basis of this correlation was verified with gas chromatography by passing standard concentrations of gas-phase acetone through a piece of polyurethane foam that was pre-wetted with a fixed volume of aqueous buffer. FIG. 22 is a diagram of the apparatus used for generating gas-phase acetone standards. A known amount of acetone was injected into a calibrated airbag containing humidified air and allowed to evaporate. The vapor was then released at a fixed rate and passed through the wetted foam. The acetone concentration of the acetone in the liquid was then measured and correlated to the starting acetone gas phase concentration. Using this partitioning strategy (that is, wetted foam), it was determined that gas phase acetone partitioned into the liquid phase to achieve theoretical equilibrium concentration values for a range of gas flow rates (0.5 to 5.0 L/min.) and gas volumes ($\geq$0.5 L). The experiment was repeated without foam using a thin liquid film (50 μL) where the acetone gas sample was impinged on the liquid in a fine gas stream. Using this partitioning strategy, gas phase acetone partitioned into the thin liquid film to achieve near equilibrium concentration values. These data were then used to devise the appropriate liquid volumes and conditions (which mimic human breath) for partitioning and quantifying gas-phase acetone electrochemically using the 3-enzyme system.

Figure 23:
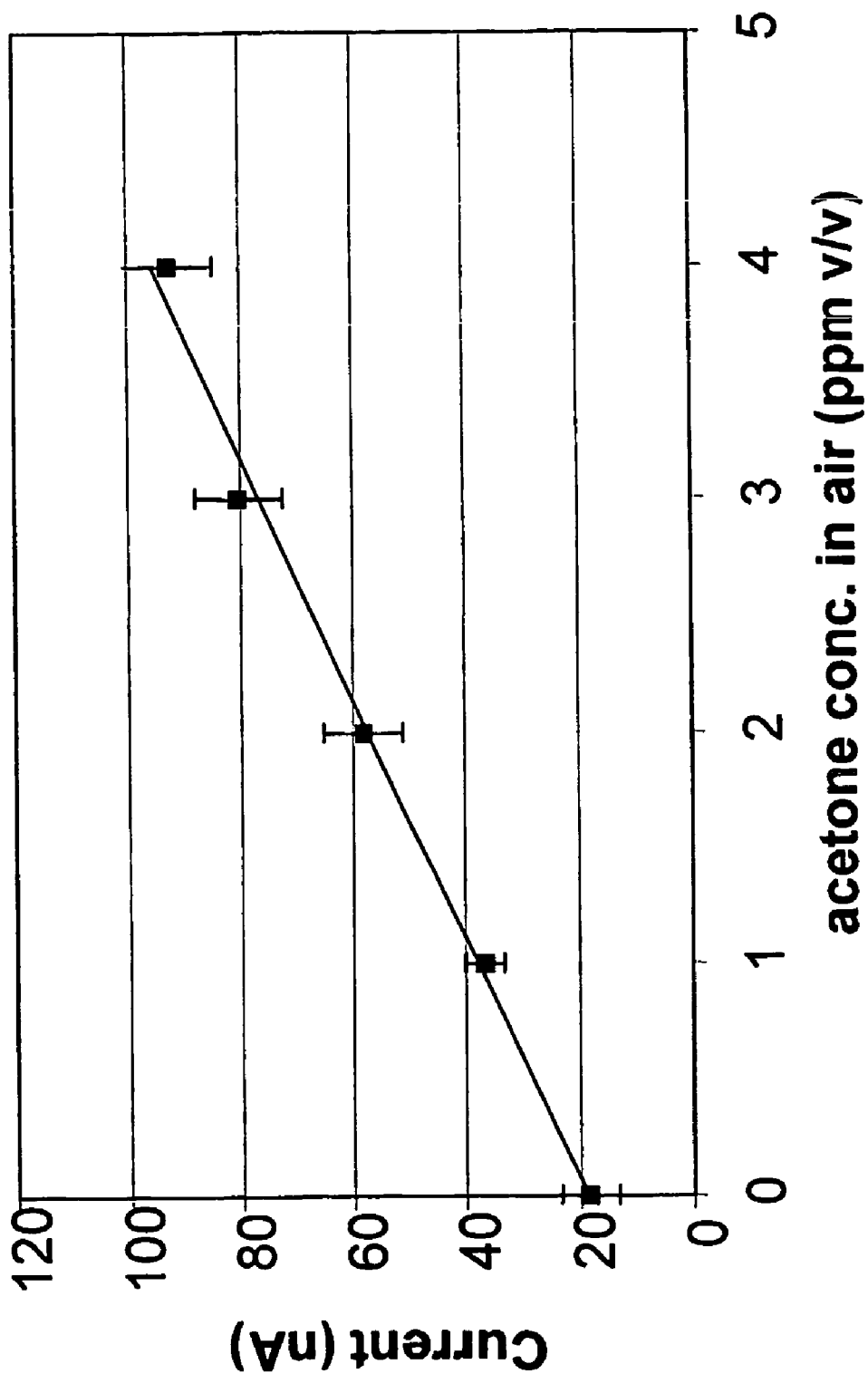
FIG. 23 graphically depicts electrochemical detection of acetone using an S-ADH coupled enzyme system, after partitioning from the gas phase to wetted foam.
Figure 24:
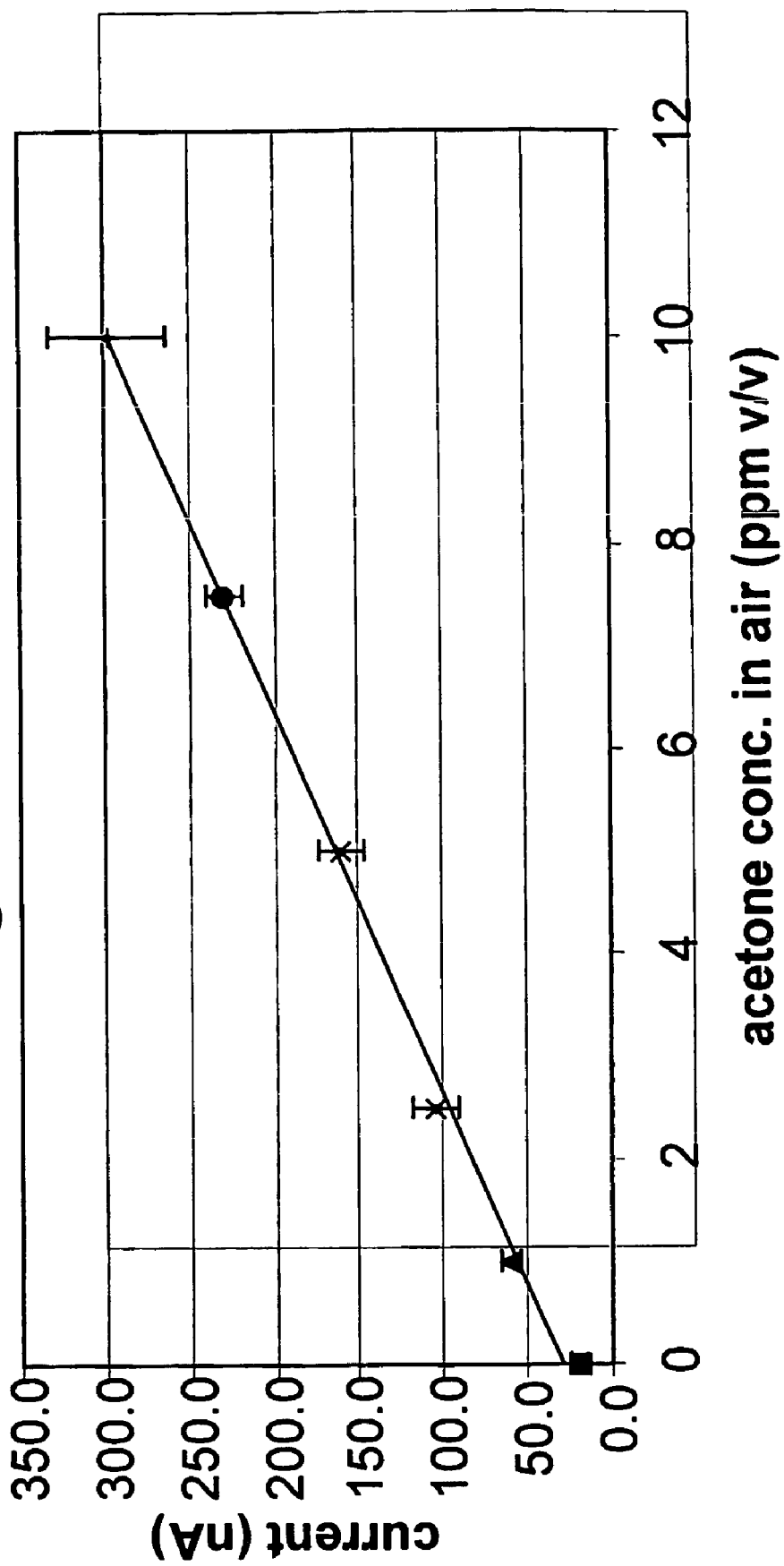
FIG. 24 graphically depicts electrochemical detection of acetone using an S-ADH coupled enzyme system, after partitioning from the gas phase to an aqueous thin film.

FIG. 23 shows the chronoamperometric response for acetone gas using polyurethane foam as a means to extract the gas sample. The 3-enzyme system was employed as the base transducer to convert the partitioned acetone into $H_2O_2$ that was then electrochemically detected using a disk platinum electrode at 350 mV (vs, Ag/AgCl). The current response to gas-phase acetone concentration has excellent sensitivity and linear characteristics over the entire range tested. Linear regression of the data gave the equation y=19.181x+18.787, with an $R^2$ value of 0.993. The experiment was repeated by partitioning gas-phase acetone into a liquid film containing the 3-enzyme system. The results are shown in FIG. 24 where chronoamperometric current response correlated linearly with the gas-phase acetone concentration. Linear regression of the data gave the equation y=26.931x+28.789, with an $R^2$ value of 0.9966. These results demonstrate the either strategy for gas-phase sampling (that is, wetted foam or liquid film) work well as systems to accurately introduce acetone gas samples to the enzyme electrode where they can be quantified electrochemically.

Biochemical properties of acetone carboxylase. In addition to S-ADH, another acetone-specific enzyme that may be suitable for use in a biosensor is acetone carboxylase. As mentioned above, acetone carboxylase is a unique enzyme that catalyzes the carboxylation of acetone to the B-ketoacid acetoacetate in a variety of aerobic and anaerobic bacteria that are able to grow using acetone as a carbon and energy source.

Many of these organisms are also capable of growth on isopropanol, where as discussed previously, a secondary alcohol dehydrogenase catalyzes the initial oxidation of isopropanol to acetone, which is then subsequently carboxylated to acetoacetate. Acetone carboxylase can be purified from *X. autotrophicus* strain Py2 via published methods. Acetone carboxylase is a multimeric enzyme comprised of three polypeptides (19.6 kDa, 78.3 kDa, and 85.3 kDa) arranged in an $\alpha_2\beta_2\gamma_2$ quaternary structure and requires MgATP for carboxylation activity. This enzyme exhibits a $V_{max}$ of 0.206 μmol acetone consumed·min$^{-1}$·mg$^{-1}$ protein and apparent $K_m$ values of 7.8 μM (acetone), 122 μM (ATP), and 4.17 mM ($CO_2$ plus bicarbonate). Butanone is also a substrate that is carboxylated at a rate of 40% of that of acetone. Acetone carboxylase has also been purified from the anaerobic, photoheterotroph *Rhodobacter capsulatus* strain B10 and is nearly identical to the Xanthobacter enzyme in terms of quaternary structure ($\alpha_2\beta_2\gamma_2$ multimer consisting of 19.5 kDa, 78.6 kDa, and 85.2 kDA polypeptides), kinetic parameters ($V_{max}$ of 0.291 μmol acetone consumed·min$^{-1}$mg$^{-1}$ protein, $K_m$ of 8.2 μM for acetone), and amino acid sequence (83% identical).

Schemes Proposed for Electrochemical Detection of the Acetone Carboxylase Reaction.

Figure 25:
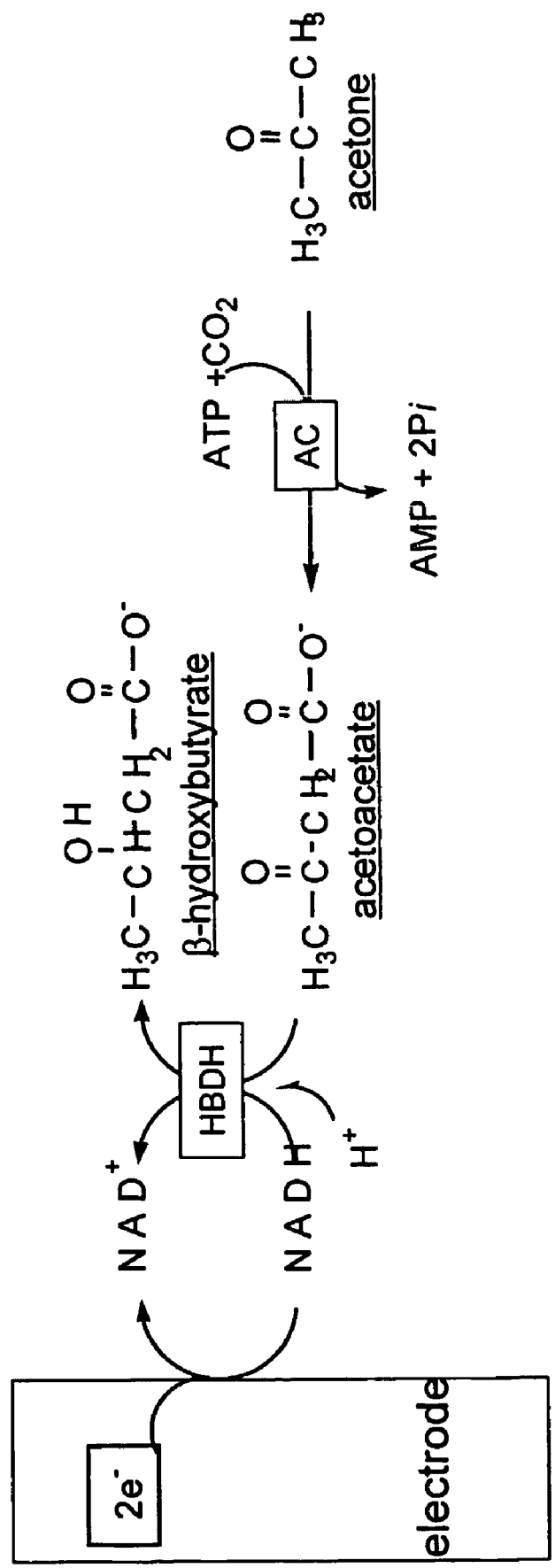
FIG. 25 schematically depicts electrochemical detection of acetone carboxylase activity coupled to β-hydroxybutyrate dehydrogenase activity.
Figure 26:
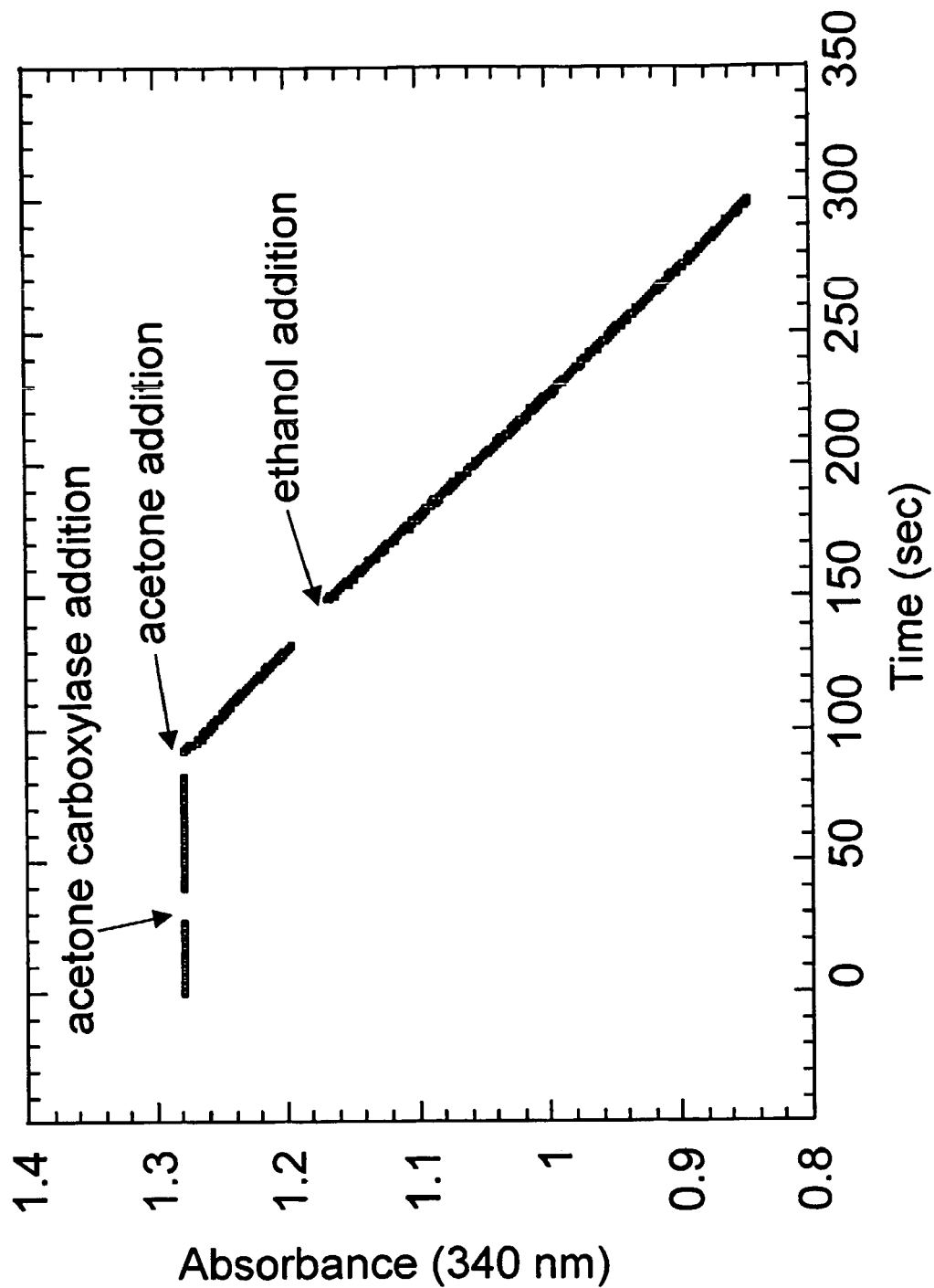
FIG. 26 graphically presents the results of a spectrophotometric assay of acetone-dependent NADH consumption using AC/HBDH coupled enzyme system.

The ATP-dependent carboxylation of acetone to form acetoacetate, the reaction catalyzed by acetone carboxylase, contains no net redox chemistry for electrochemical detection. To be useful in a biosensor, it was necessary to develop a coupled enzyme reaction that provided substrate oxidation or reduction. As shown in FIG. 25, acetone carboxylase can be coupled to β-hydroxybutyrate dehydrogenase where the acetoacetate formed by the carboxylation reaction is subsequently reduced by this enzyme with concomitant oxidation of NADH. The acetone-dependent consumption of NADH can then be monitored electrochemically using the method described above for S-ADH enzyme. FIG. 26 shows a spectrophotometric plot of the rate of NADH oxidation vs. time using this enzyme system. NADH oxidation was observed only after acetone addition and no decrease in the rate was observed by addition of ethanol (10 mM) indicating that it did not inhibit the reaction. The enzyme system was highly specific for acetone, but alternative compounds (for example 1-propanol, 2-propanol, 1-butanol, and 2-butanol) were not active nor did they inhibit acetone carboxylation activity. Butanone, which normally is a substrate that is carboxylated at a rate of 40% of that of acetone, displayed a rate of about 3 to 4% of acetone using the coupled enzyme system. This is presumably due to the substrate specificity of the β-hydroxybutyrate dehydrogenase.

The acetone detection limit of the acetone carboxylase reaction coupled to β-hydroxybutyrate dehydrogenase was investigated using spectrophotometry in a manner similar to that described above using S-ADH from *X. autotrophicus* strain Py2. Using acetone carboxylase and β-hydroxybutyrate dehydrogenase coupled enzyme system, the NADH consumption response was linear (correlation coefficient=0.99954) for acetone concentrations ranging from 0.058 to 2.8 ppm (w/v). The lower end of the acetone detection range (0.058 to 0.29 ppm (w/v)) is within the detection parameters required for diagnostic breath acetone analysis.

Figure 27:
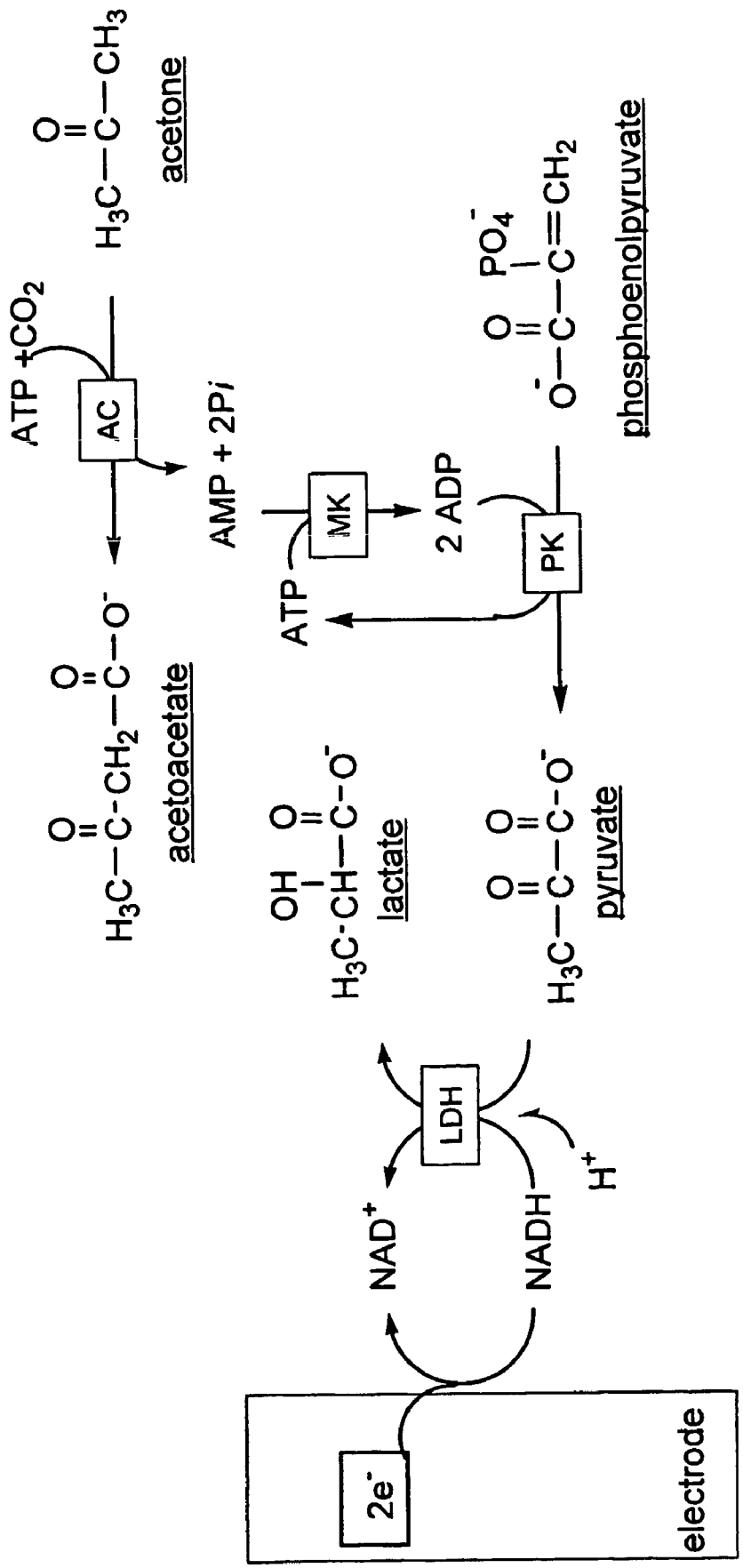
FIG. 27 schematically illustrates electrochemical detection of acetone carboxylase (AC) reaction coupled to pyruvate kinase (PK), myokinase (MK), and lactate dehydrogenase (LDH) activities.

Shown in FIG. 27 is an alternative enzyme system that couples acetone carboxylase ATP-hydrolysis to NADH oxidation. This four component enzyme system, which has been described previously for spectrophotometric detection of acetone carboxylase activity, can easily be adapted for electrochemical detection (FIG. 27). Using this coupled assay, acetone carboxylase generates AMP as acetone is carboxylated, the AMP that forms is then converted to two molecules of ADP in a reaction catalyzed by myokinase. The ADP formed by this reaction is then phosphorylated to ATP by pyruvate kinase which catalyzes the conversion of phosphoenolpyruvate to pyruvate. The pyruvate that forms is then reduced by lactate dehydrogenase consuming NADH in the process. Although this enzyme system is more complex, it utilizes the same electrochemical detection method as described above.

Figure 28:
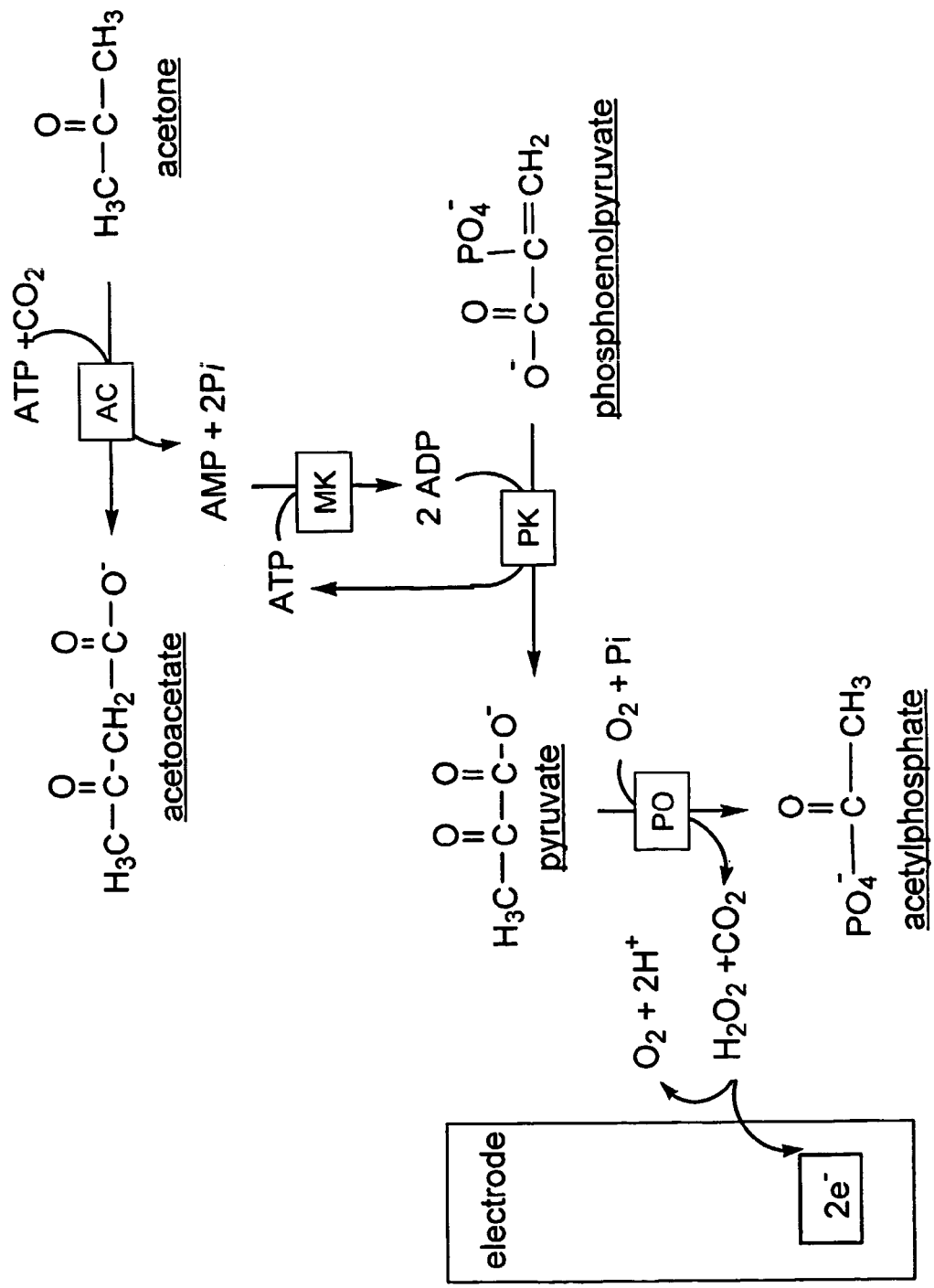
FIG. 28 schematically shows electrochemical detection of acetone carboxylase (AC) reaction coupled to pyruvate kinase (PK), myokinase (MK), and pyruvate oxidase (PO) activities.
Figure 29:
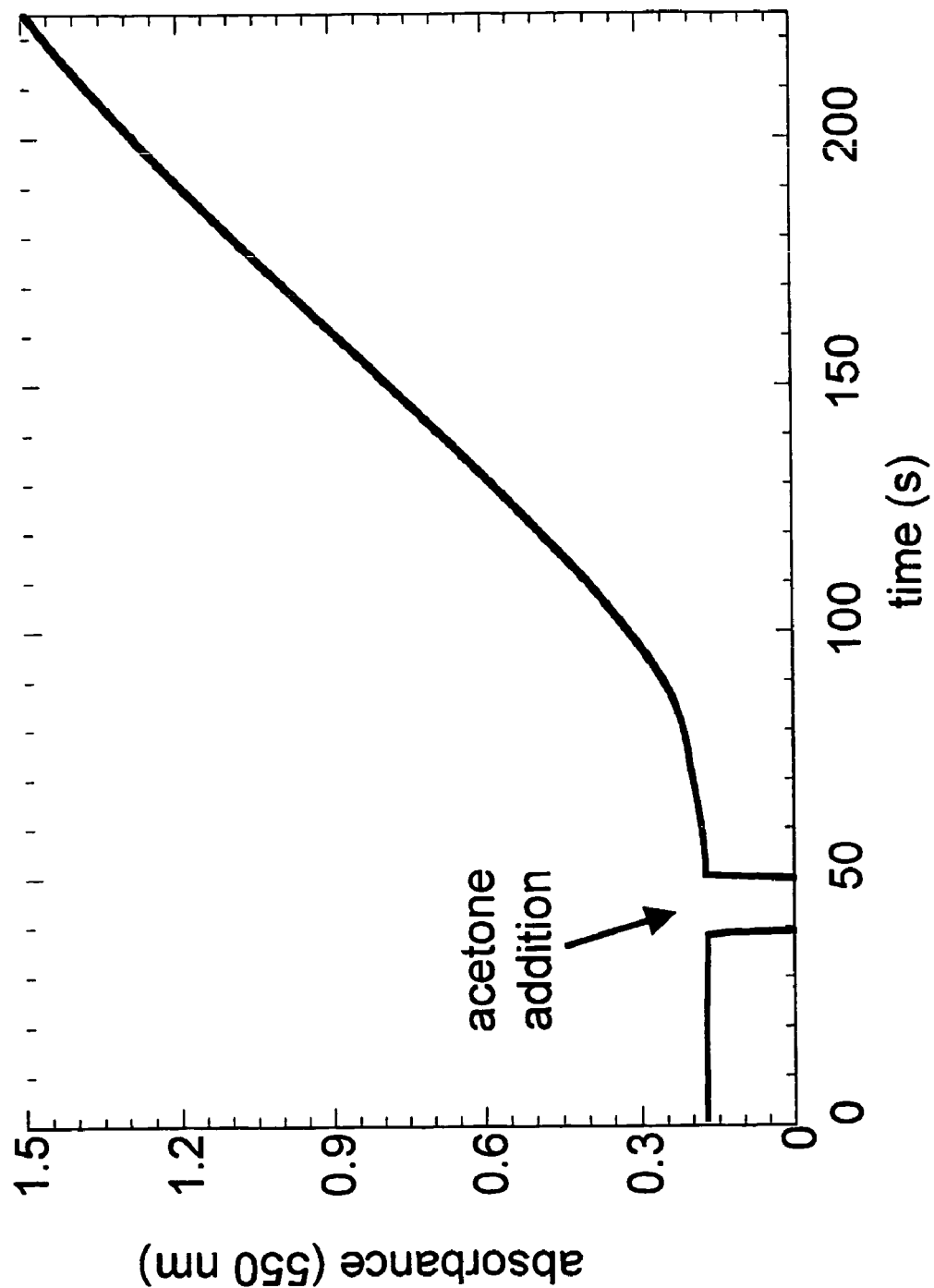
FIG. 29 presents a plot of spectrophotometric absorbance detection of H$_2$O$_2$ generated in response to acetone by a coupled enzyme system containing acetone carboxylase from *Xanthobacter* Py2, myokinase, pyruvate kinase, and pyruvate oxidase, in the presence of horseradish peroxidase (HRP) and electron acceptor dyes; the HRP and dyes permitting the photometric detection of H$_2$O$_2$.
Figure 30:
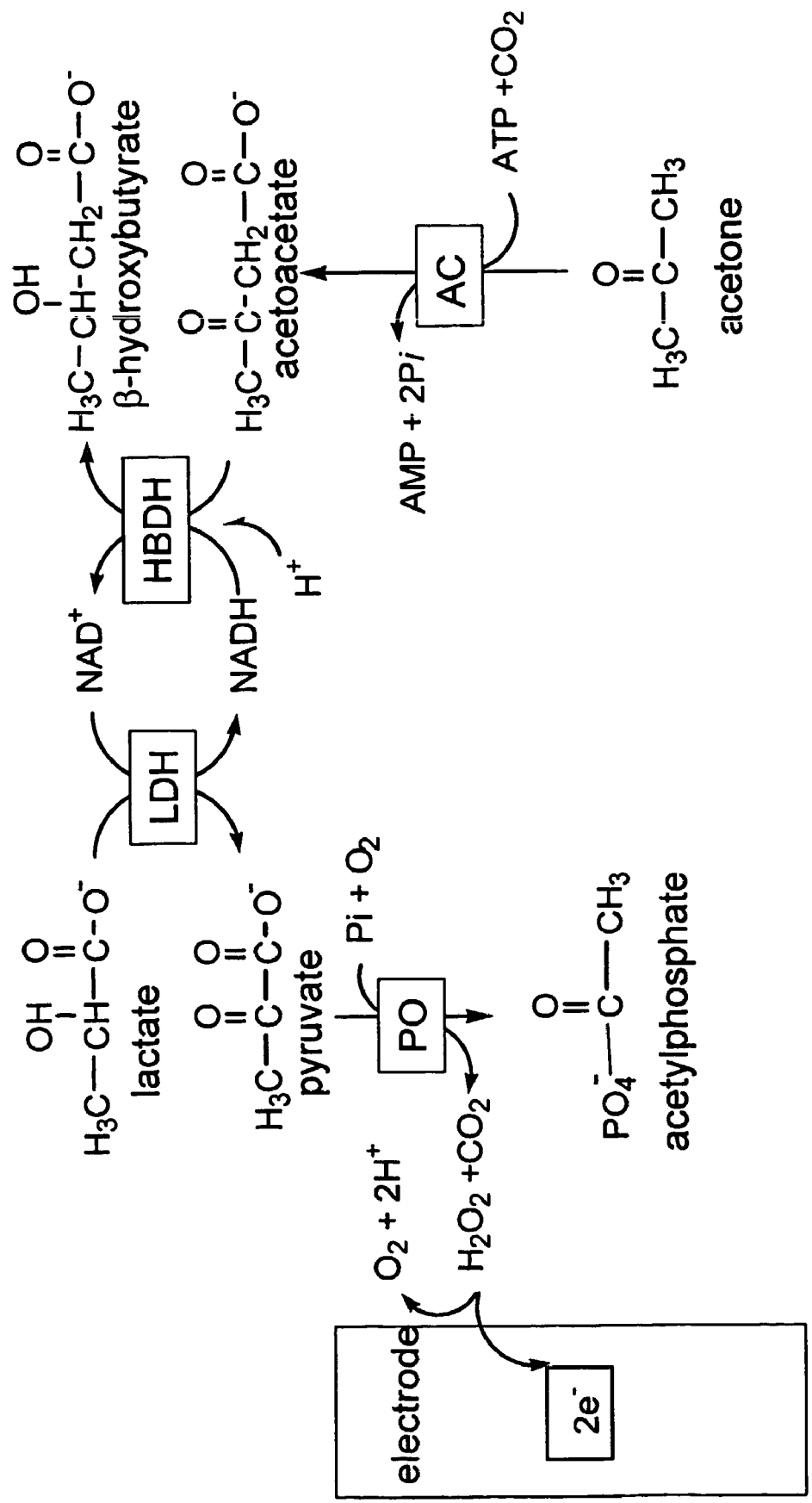
FIG. 30 schematically shows acetone-dependent H$_2$O$_2$ formation using an acetone carboxylase coupled enzyme system; the result is electrochemical detection of acetone using the acetone carboxylase (AC) reaction coupled to β-hydroxybutyrate dehydrogenase (HBDH), lactate dehydrogenase (LDH), and pyruvate oxidase (PO) activities.

A third means to monitor acetone carboxylase activity electrochemically involves a modification of the strategy presented in FIG. 27, so that ATP hydrolysis is coupled to $H_2O_2$ formation. As shown in FIG. 28, in this strategy a pyruvate oxidase is substituted for lactate dehydrogenase; thus, as pyruvate is generated it is oxidized, thereby forming $H_2O_2$. In order to investigate this enzyme system, the enzyme reaction mix (containing coupling enzymes and reagents) was prepared with acetone carboxylase from *Xanthobacter* Py2, along with myokinase, pyruvate kinase, and pyruvate oxidase, in the presence of horseradish peroxidase (HRP) and electron acceptor dyes to allow monitoring of the reaction system end-product ($H_2O_2$) spectrophotometrically. FIG. 29 illustrates the results of the coupling reactions, wherein an increase in absorbance was observed, upon addition of acetone, that corresponded to $H_2O_2$ formation. As was the case for the S-ADH-$H_2O_2$ generating system, a lag was observed after acetone addition that could be shortened with further optimization of the reaction conditions. Shown in FIG. 30 is a fourth means to monitor acetone carboxylase activity electrochemically that involves combining certain aspects of the strategies diagramed in FIGS. 27 and 28. Using this strategy, the NAD$^+$ generated from the coupled reaction between acetone carboxylase and β-hydroxybutyrate dehydrogenase was used by lactate dehydrogenase to oxidize lactate to pyruvate. The pyruvate thus formed was oxidized by pyruvate oxidase to generate $H_2O_2$ which is then detected; electrochemical detection of the $H_2O_2$ generated was detected electrochemically (data not shown).

Figure 31:
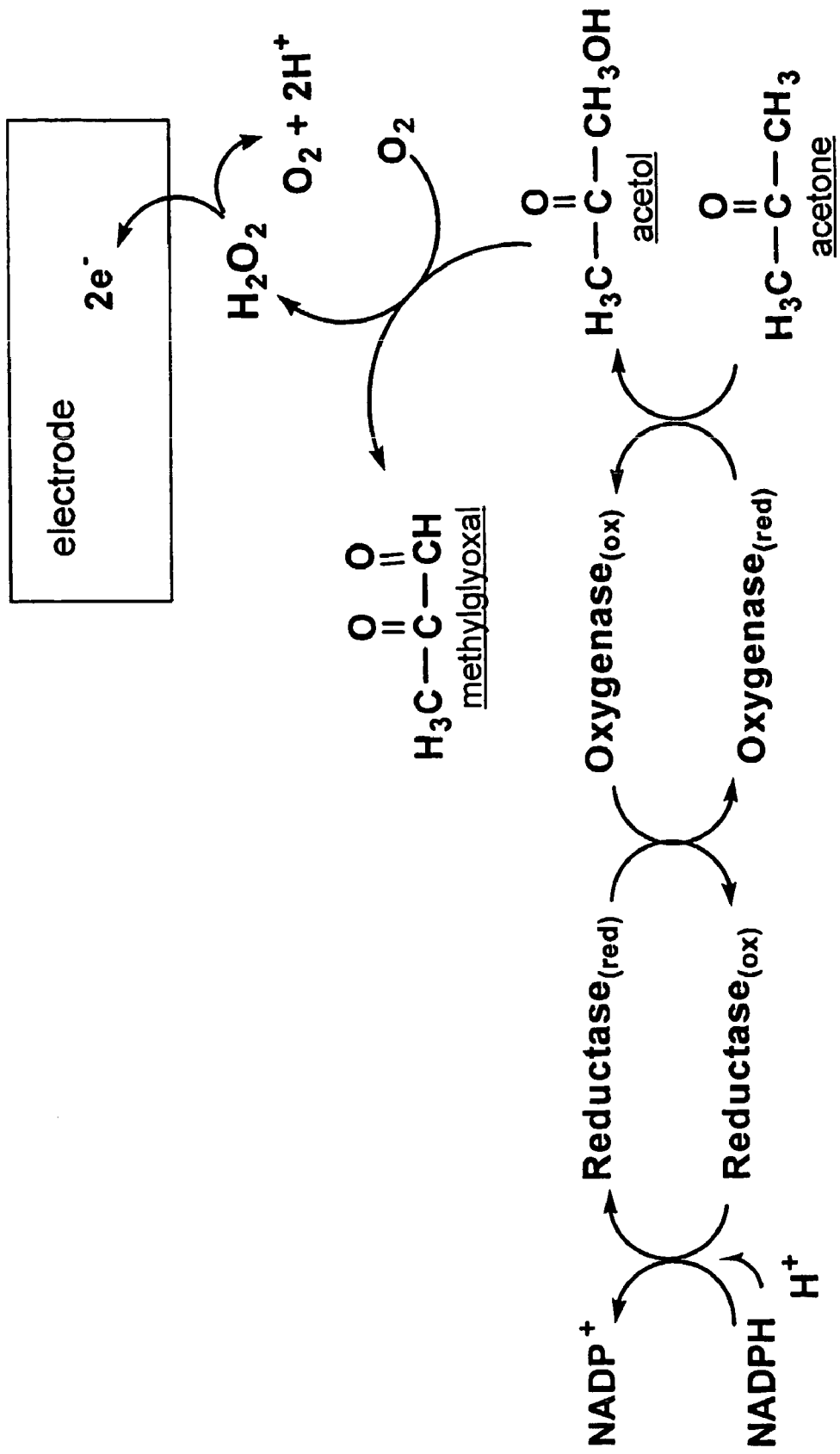
FIG. 31 schematically shows electrochemical detection of P450 monooxygenase coupled to galactose oxidase activities.

Also, as an alternative strategy to monitoring acetone-dependent consumption of NAD(P)H, the acetone monooxygenase reaction can be coupled to galactose oxidase to form $H_2O_2$ as shown in FIG. 31. Alternatively, acetone monooxygenase NAD(P)+ formation can be coupled to $H_2O_2$ formation by use lactate dehydrogenase and pyruvate oxidase.

Stability of acetone carboxylase. As described above for the S-ADH enzyme, it is important to devise a formulation for stabilizing acetone carboxylase activity in a dry form for long periods of time at room temperature. Purified acetone carboxylase was lyophilized and found to retain approximately 90% activity relative to a non-lyophilized control when rehydrated and assayed within one day of lyophilization (data not shown). However, the activity decreased over the course of several days, for samples stored at room temperature and 4° C. As was the case for S-ADH, the presence of trehalose stabilized activity (>90%) for at least 111 days in samples held at room temperature. In a separate experiment, the entire coupling assay reaction mix (that is acetone carboxylase from *X. autotrophicus* strain Py2, β-hydroxybutyrate dehydrogenase, NADH, ATP, buffer, potassium acetate, and $MgCl_2$) was lyophilized to determine whether assay components were stable to this treatment. When the assay mix was rehydrated and assayed within one day, 84% of the activity was retained. When trehalose was included in the reaction mixture that was lyophilized, 95% of the activity was retained. A third stability experiment was performed where acetone carboxylase in the presence of trehalose (20% w/v) was allowed to air dry as opposed to being lyophilized. In this case, after 24 hours, acetone carboxylase retained a 100% of its activity (data not shown). Allowing an enzyme to air dry (instead of lyophilization) with retention of activity may be an important requirement for screen-printing technology.

Other prospects for incorporating acetone-specific enzymes into an enzyme-based electrochemical sensor for breath acetone. In some propane-oxidizing bacteria, acetone is formed as an intermediate that is believed to undergo hydroxylation in an $O_2$-dependent mono-oxygenase-catalyzed reaction to form acetol (hydroxyacetone). Although this bacterial enzyme has not been fully characterized, it functions in a manner resembling that of other mono-oxygenase enzymes and systems described to date. Known monooxygenases are typically comprised of multiple enzyme components (2-4 enzyme components), including a pyridine nucleotide-dependent reductase, an electron transfer protein (for example ferredoxin), and an active site-containing oxygenase component. NAD(P)H provides the necessary reductant for $O_2$ activation and incorporation of one oxygen atom into the aliphatic hydrocarbon substrate. Acetone-dependent consumption of NAD(P)H by an acetone mono-oxygenase reaction could be monitored electrochemically as described above for secondary alcohol dehydrogenase- and acetone carboxylase-coupled enzyme systems (FIG. 1). In addition, an acetone P450 mono-oxygenase has been described in mammalian systems. Although this enzyme likely has different biophysical properties (that is different size of subunit molecular masses, amino acid sequences, etc.) from a bacterially-derived acetone mono-oxygenase, the reaction it catalyzes is suitable for monitoring acetone in an enzyme-based biosensor, using a strategy parallel to that described for bacterial acetone mono-oxygenase. Acetol, the product of the acetone mono-oxygenase reaction, has been reported to be a substrate for galactose oxidase (J. Tkac et al., Enzyme and Microbial Technology (2001) 28: 383-88; M. M. Whittaker and J. W. Whittaker, Biochemistry (2001) 40:7140-48). Therefore, as an alternative strategy to monitoring acetone-dependent consumption of NAD(P)H, the acetone mono-oxygenase reaction can be coupled to galactose oxidase to form $H_2O_2$ as shown in FIG. 31.

Acetone Signal Amplification Strategies

Amplification of the enzyme electrode signal may be important where acetone concentrations in tested samples are low. For example, the basal level (in non-fasting individuals) of acetone in breath is relatively low (0.2 to 0.5 ppm v/v). Amplification can be accomplished by using enzymes to recycle substrates (futile cycles), thereby magnifying the output signal. Consequently, a low, sub-saturating level of acetone would yield a continuous rate of response that would steadily increase the signal intensity over time. The rate of increase would be dependent on the initial amount of acetone detected, as long as the concentration is sub-saturating to the enzyme system employed. The biosensor can then be calibrated by measuring the rates of response and correlating them to the initial acetone concentration.

Figure 32:
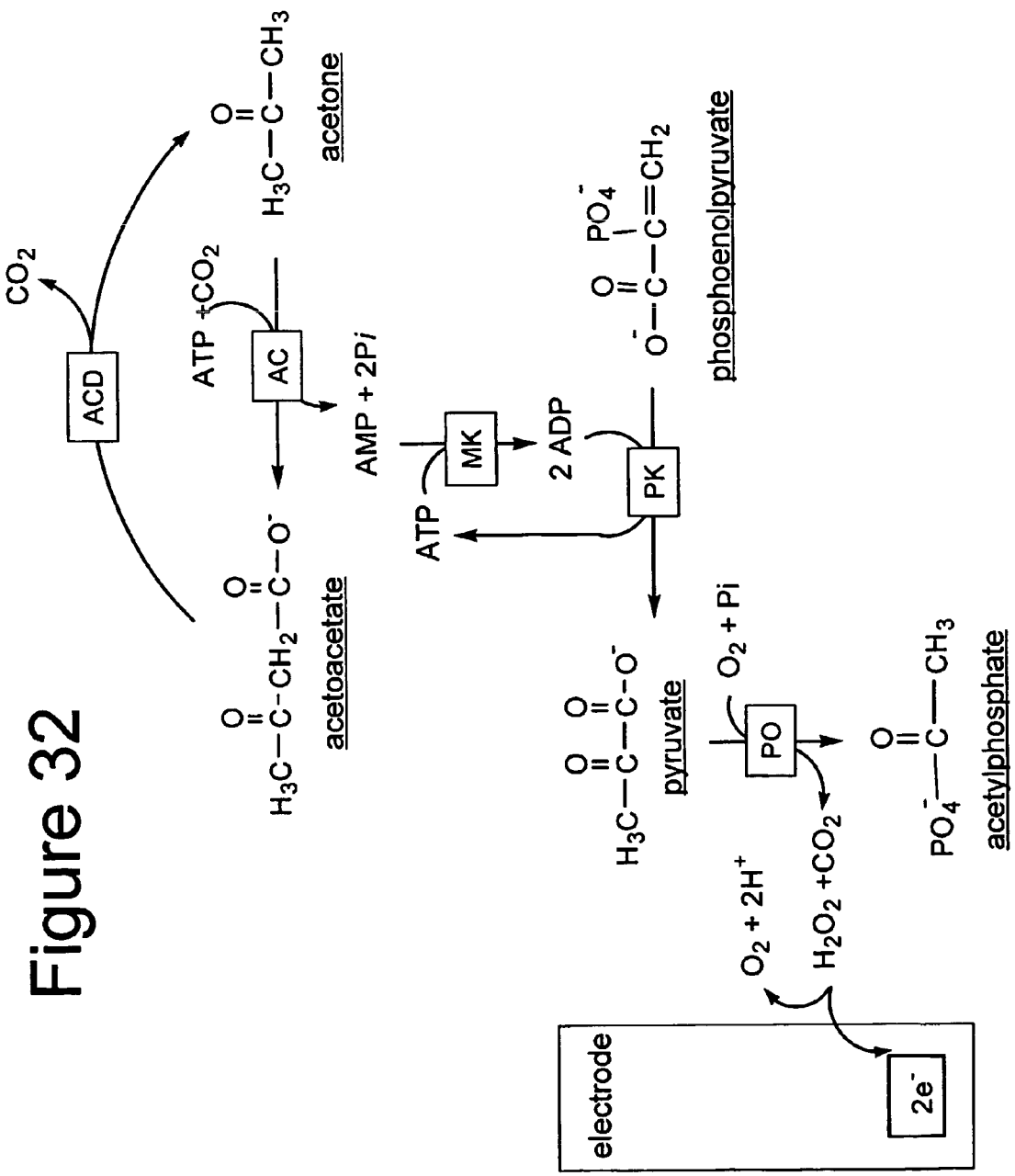
FIG. 32 schematically illustrates signal amplification strategy using acetone carboxylase (AC) coupled enzyme system containing acetoacetate decarboxylase (ACD), myokinase (MK), pyruvate kinase (PK), and pyruvate oxidase (PO).
Figure 33:
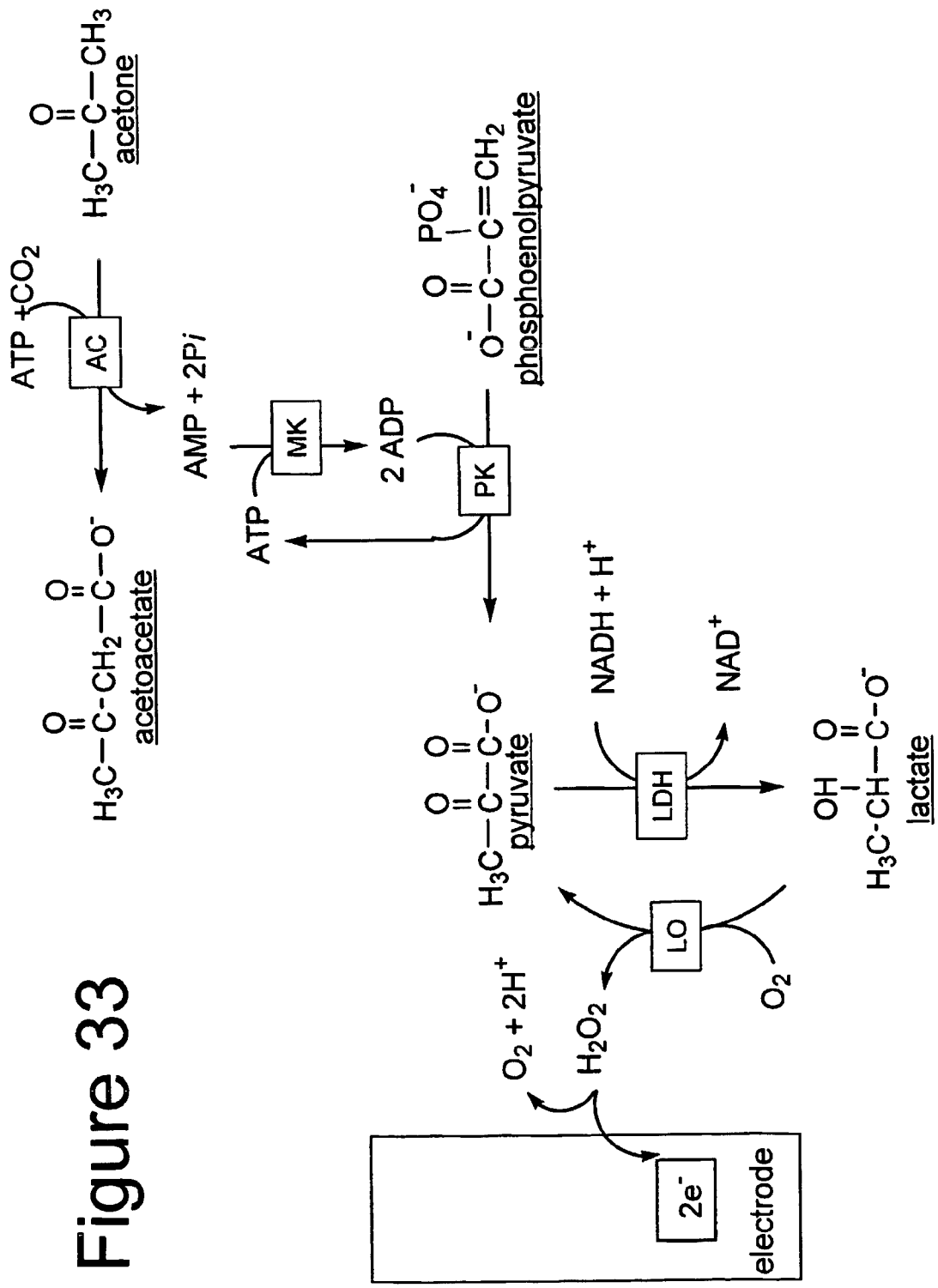
FIG. 33 schematically illustrates signal amplification strategy using an acetone carboxylase (AC) coupled enzyme system containing myokinase (MK), pyruvate kinase (PK), lactate dehydrogenase (LDH), and lactate oxidase (LO).

In a first embodiment, shown in FIG. 32, an amplification scheme uses acetoacetate decarboxylase. Acetoacetate decarboxylase, found in fermentative microorganisms, catalyzes the opposite reaction of an acetone carboxylase. Using this scheme, acetone carboxylase ATP hydrolysis activity is coupled to $H_2O_2$ generation as presented in FIG. 28, however the addition of acetoacetate decarboxylase recycles acetoacetate back to acetone, thus creating a system that does not deplete the concentration of acetone. Another variation of this amplification system is shown in FIG. 33, wherein lactate oxidase is incorporated into the coupled enzyme system presented earlier in FIG. 27. As pyruvate is reduced to lactate, lactate oxidase catalyzes the recycling of lactate back to pyruvate generating $H_2O_2$ in the process that is then detected electrochemically.

Figure 34:
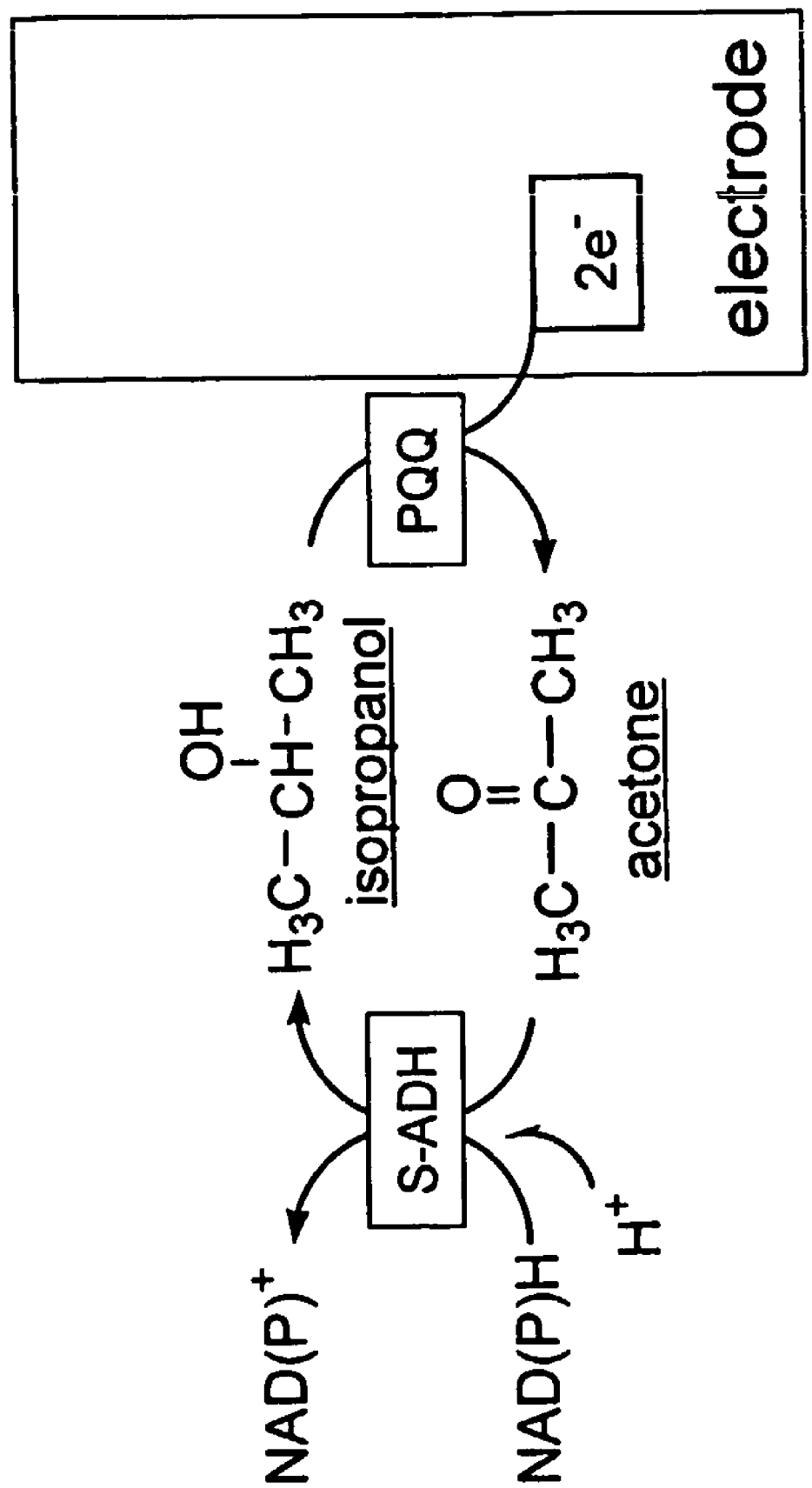
FIG. 34 schematically illustrates linear signal amplification strategy using a secondary alcohol dehydrogenase and a pyrroloquinolinequinone-dependent alcohol dehydrogenase (PQQ).
Figure 35:
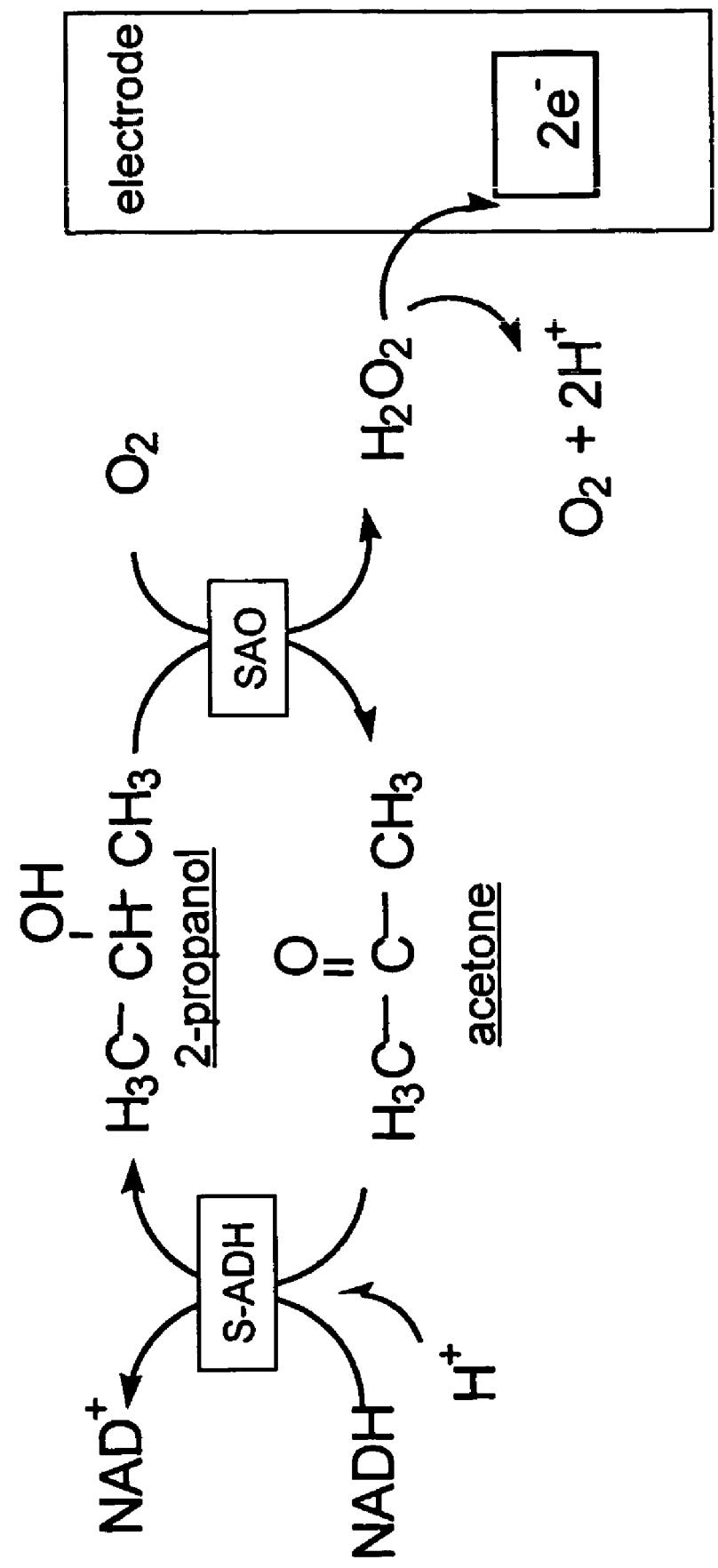
FIG. 35 schematically illustrates linear signal amplification strategy using S-ADH and secondary alcohol oxidase (SAO).

A number of different acetone signal amplification strategies can be employed with S-ADH enzymes. In a first embodiment, illustrated in FIG. 34, an S-ADH enzyme is coupled to a pyrroloquinoline quinone (PQQ)-dependent alcohol dehydrogenase; one examples of such an enzyme is that isolated from *Pseudomonas* sp. strain VM15C (Shimao 1986). This particular PQQ-dehydrogenase has been reported to have specificity to low-molecular-weight secondary alcohols rather than primary alcohols. In this amplification strategy, an S-ADH enzyme reduces acetone to isopropanol. The isopropanol thus formed is then reoxidized to acetone by PQQ-dependent alcohol dehydrogenase. The electrons from this oxidation are transferred directly to the electrode through prosthetic groups of the PQQ enzyme. Integrated enzyme electrodes involving direct electron transfer have previously been reported for this class of enzymes. A similar example is shown in FIG. 35, in which an S-ADH enzyme is coupled to a secondary alcohol oxidase (SAO; EC 1.1.3.18). SAOs have been isolated from a number of different organisms, for example, *Pseudomonas* sp. See, for example, M. Morita et al., Purification and properties of secondary alcohol oxidase from a strain of *Pseudomonas*. Agric. Biol. Chem. 43:1225-35 (1979). Using this strategy, acetone undergoes recycling, during which it is initially reduced by S-ADH and subsequently reoxidized by SAO, concurrently producing $H_2O_2$ for each turnover of the substrate cycle. This linear amplification scheme is advantageous in that it is simple (only two enzymes are needed) and takes advantage of the relative ease with which $H_2O_2$ can be monitored.

This strategy for signal amplification, that is by combining the actions of an alcohol dehydrogenase and an alcohol oxidase, was investigated by coupling primary alcohol oxidase (AO) to primary alcohol dehydrogenase. Using ethanol as the substrate, and measuring the increase in $H_2O_2$ formation over identical response times, a 7- to 10-fold increase was observed using the two-enzyme system over AO alone (data not shown). The signal can be increased further for the two-enzyme system by allowing the response time to extend for longer periods. This demonstrates that a practical method for amplifying a response to acetone is to couple S-ADH to SAO.

Figure 36:
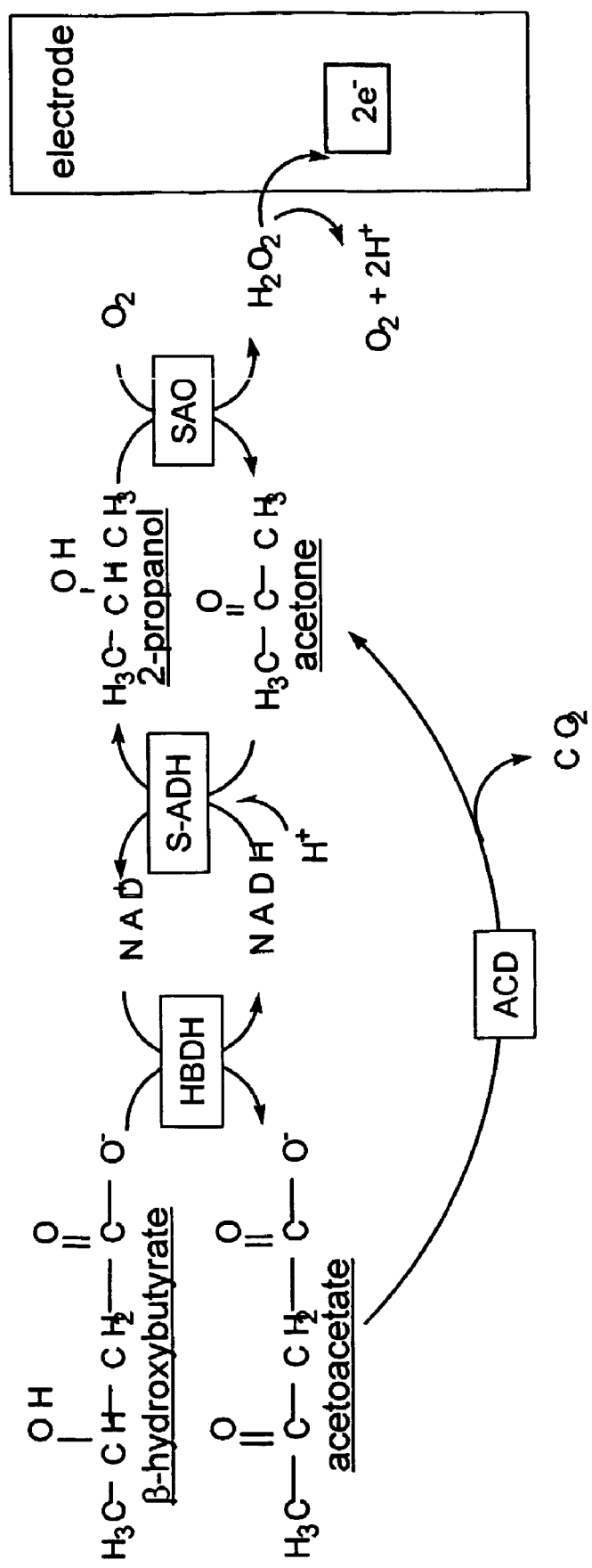
FIG. 36 schematically illustrates exponential signal amplification utilizing S-ADH coupled to beta-hydroxbutyrate dehydrogenase (HBDH), acetoacetate decarboxylase (ACD), and SAO.

FIG. 36 illustrates a third example of an amplification strategy, which enhances the S-ADH/SAO coupled system by taking advantage of the $NAD^+$ produced from the reaction catalyzed by S-ADH. In this case, $NAD^+$ produced from the reduction of acetone to isopropanol is coupled to hydroxybutyrate dehydrogenase (HBDH) where hydroxybutyrate (loaded in excess) is oxidized to acetoacetate. Acetoacetate is then decarboxylated by acetoacetate decarboxylase (ACD) to form acetone, thereby increasing the amount of acetone (by one molecule) that undergoes subsequent recycling. As opposed to the enzyme system illustrated in FIG. 35, which provides linear amplification of an acetone response (that is for every substrate cycle, the amount of $H_2O_2$ produced is doubled), this type of amplification system would exponentially increase the amount of $H_2O_2$ output, allowing detection of extremely low levels of acetone in a biological sample.

Figure 37:
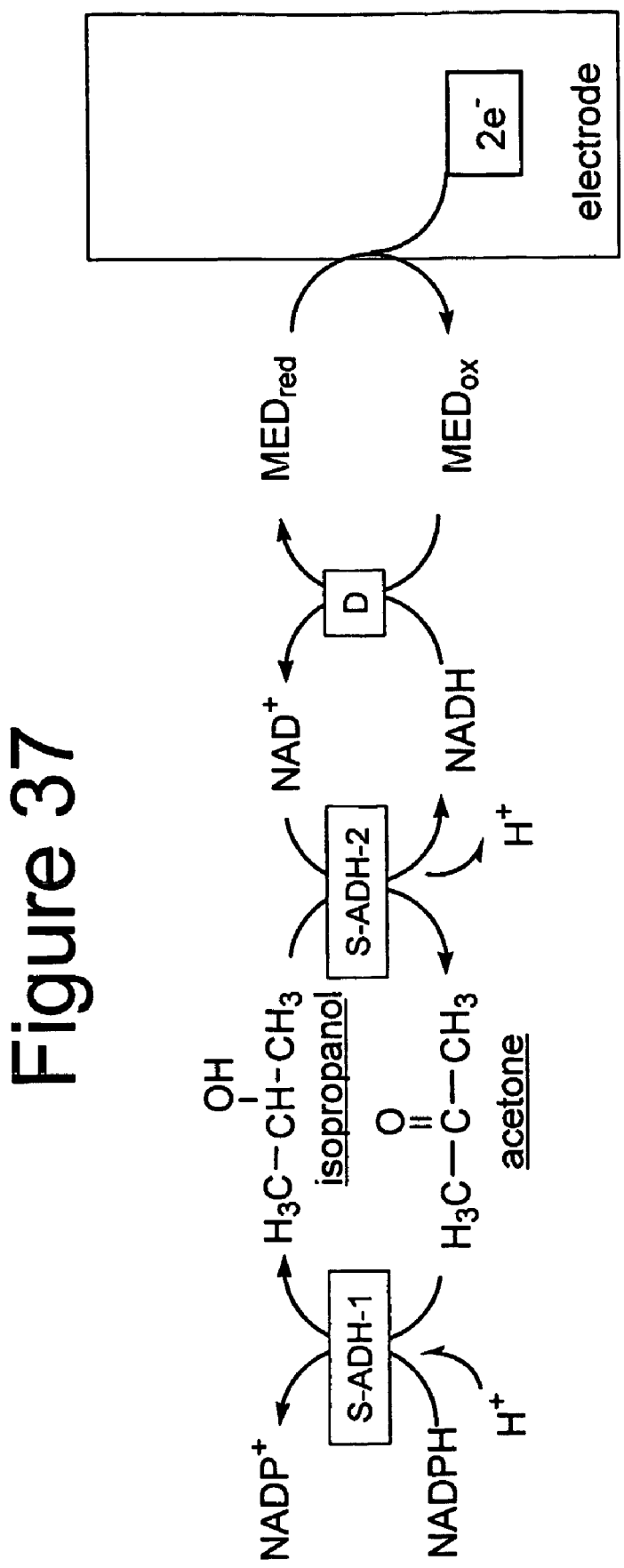
FIG. 37 schematically illustrates a linear signal amplification strategy using two different pyridine nucleotide-dependent secondary alcohol dehydrogenases: S-ADH-1 (NADPH-specific secondary alcohol dehydrogenase), S-ADH-2 (NADH-specific secondary alcohol dehydrogenase), along with D (NADH-specific diaphorase), and MED (an electron mediator).

A fourth example is shown in FIG. 37, in which an amplification strategy exploits the preferences of S-ADH enzymes for NADH or NADPH pyridine cofactors. In this case, the first S-ADH catalyzes the reduction of acetone to isopropanol, while oxidizing NADPH. The second S-ADH re-oxidizes isopropanol to acetone, while generating NADH that is then utilized by an NADH-dependent diaphorase (D) to reduce an electron mediator that is then detected, for example, by oxidation at the electrode. While this system does provide amplification, a commercial embodiment thereof would preferably employ S-ADH enzymes having substantially absolute coenzyme specificity, as well as a means to control or actively monitor the coenzyme concentration(s) and the substrate/product ratios of the chemical equilibrium.

As described herein, in a preferred embodiment a means is provided for incorporating acetone-specific enzymes in an electrochemical or non-electrochemical biosensor, thereby enabling such activities as diagnostic monitoring of acetone on human breath. As discussed herein, preferable strategies for electrochemical detection of acetone using a combination of enzymes forming linked enzyme systems include: 1) the secondary alcohol dehydrogenase (S-ADH)-catalyzed reduction of acetone with concomitant NADPH consumption, and 2) S-ADH-catalyzed reduction of acetone with concomitant NADH consumption (that is collectively, S-ADH-catalyzed reduction of acetone with concomitant NAD(P)H consumption, with NAD(P)H being detected electrochemically); 3) acetone carboxylase reaction coupled to (for example, β-hydroxybutyrate dehydrogenase) consumption of NADPH, and 4) acetone carboxylase reaction coupled to (for example, B-hydroxybutyrate dehydrogenase) consumption of NADH (that is collectively, acetone carboxylase reaction coupled to consumption of NAD(P)H, with NAD(P)H being detected electrochemically); 5) acetone carboxylase reaction ATP hydrolysis coupled to NADPH consumption, and 6) acetone carboxylase reaction ATP hydrolysis coupled to NADH consumption (that is collectively, acetone carboxylase reaction ATP hydrolysis coupled to NAD(P)H consumption, with NAD(P)H being detected electrochemically); 7) S-ADH reaction $NADP^+$ formation coupled to $H_2O_2$ formation, and 8) S-ADH reaction $NAD^+$ formation coupled to $H_2O_2$ formation (that is collectively, S-ADH reaction $NAD(P)^+$ formation coupled to $H_2O_2$ formation, with $H_2O_2$ being detected electrochemically); 9) acetone carboxylase reaction ATP hydrolysis coupled to $H_2O_2$ formation with $H_2O_2$ being detected electrochemically; 10) acetone carboxylase reaction coupled to (for example, β-hydroxybutyrate dehydrogenase) $NADP^+$ formation coupled to $H_2O_2$ formation, and 11) acetone carboxylase reaction coupled to (for example, β-hydroxybutyrate dehydrogenase) $NAD^+$ formation coupled to $H_2O_2$ formation (that is collectively, acetone carboxylase reaction coupled to, for example, β-hydroxybutyrate dehydrogenase, $NAD(P)^+$ formation coupled to $H_2O_2$ formation, with $H_2O_2$ being detected electrochemically); and 12) acetone mono-oxygenase coupled to NADPH oxidation, and 13) acetone mono-oxygenase coupled to NADH oxidation (that is collectively, acetone mono-oxygenase coupled to NAD(P)H oxidation). The invention is not limited to these particular enzyme systems, and any acetone-specific enzyme may be employed in the enzyme systems of the invention. Moreover, any electrochemically detectable cofactors and by-products suitable for coupling with acetone-specific enzymes may be employed.

Example 5

An acetone biosensor according to the present invention may be utilized to track the release of acetone formed by metabolism of a "tag" compound administered as part of a drug formulation or other administered or implanted composition. In a preferred embodiment, acetoacetic acid and/or any of its pharmaceutically acceptable salts and pharmaceutically acceptable esters or amides may be used as a tag to track the release of compositions administered to, or implanted into, a living organism or a group of living organisms, for example, an environmental sample or a cell culture or colony. Pharmaceutically acceptable base addition salts of acetoacetic acid include alkali metals, such as sodium, potassium and lithium salts; alkaline earth metals, such as calcium and magnesium; transition metals, such as zinc, iron and copper; carbonate, bicarbonate, ammonium, alkylammonium, alkylamine, alkanolamine and hydroxy alkamine salts. Also suitable are alcohol esters. Preferably, sodium or potassium salts of acetoacetic acid are used. A preferred ester is ethyl ester. Acetoacetic acid, as well sodium and potassium salts thereof, are solids at room temperature, whereas ethyl acetoacetate is a liquid at room temperature. Salts of acetoacetic acid may be administered for tagging purposes at a dosage of about 10 mg to about 200 mg, preferably in a range from about 10 mg to about 170 mg.

During β-oxidation of fatty acids, two molecules of acetyl CoA are hydrolyzed from a fatty acid chain with each oxidation cycle, during which ATP is generated for energy needs. The acetyl CoA so produced may be metabolized to carbon dioxide, or it may be utilized in the formation of ketone bodies via conversion into acetoacetate in the liver of a mammal. The acetoacetate produced in this manner may serve as an alternative to glucose as an energy source, particularly during periods of starvation. Acetoacetate produced by the liver is released into the bloodstream for use as fuel, particularly by the brain and heart muscle. Free acetoacetic acid infused into the bloodstream of an animal has been shown to induce increases in alanine and glutamine levels, possibly due to a stimulation of muscular output of these amino acids, while decreases in blood glucose levels have been noted. In general, acetone is rapidly cleared from mammalian systems via metabolism/exhalation and excretion in urine. Acetoacetate spontaneously decarboxylates to form acetone and $CO_2$, and the odor of acetone is noticeable in the breath of individuals having high blood levels of acetoacetate. Exhalation as $CO_2$ and unchanged acetone is the primary route of acetone elimination from the body. The amount of unchanged acetone exhaled is related to concentrations of acetone in the body. Both urinary and exhaled acetone can be detected in biological samples using an acetone-specific biosensor.

Thus, an acetone-specific biosensor may be employed to detect the release of acetone derived from the acetoacetate tag and thereby track the release of an administered therapeutic compound or implanted composition, or the biodegradation and/or bio-erosion of the implanted composition.

In a preferred embodiment, the administered formulation will contain the acetoacetic acid, salt, ester, or amide in admixture with a primary substance whose bio-release is desired. Examples of such primary substances include, but are not limited to: pharmaceutically acceptable active ingredients, biopharmaceuticals (for example, proteins such as antibodies, hormones, enzymes, serums, and vaccines; gene therapies), and other bioactive substances such as dietary supplements (for example, vitamins, minerals, herbal supplements, and nutraceuticals).

Pharmaceutical active ingredients include, but are not limited to: analgesics, anesthetics, antacids, anthelmintics, antibiotics, anticoagulants, anticonvulsants, antidepressants, anti-emetics, antifungals, antihistamines, antihypertensives, anti-infectives, anti-inflammatories, antimanic agents, antimicrobials, antineoplastic agents, antiparasitics, antiprotozoals, antipsychotics, antipyretics, antiseptics, antitussives, antivirals, autonomic agents (such as anticholinergics, sympathomimetics, sympatholytics, parasympathomimetics, parasympatholytics), bronchodilators, cardiovascular drugs, cathartics, chemotherapeutic agents, coagulants, contraceptives, depressants, diuretics, expectorants, hematopoietic to agents, hypnotics, immunomodulators, psychopharmacologic agents, sedatives, stimulants, tranquilizers, vasoconstrictors, and vasodilators.

In a preferred embodiment, the implanted composition will be a solid material into which the acetoacetic acid, salt, amide, or ester, or formulation therewith has been loaded or imbedded, for example, as powdered- or granulated-particles or liquid- or solution-droplets, distributed throughout the bulk of the solid material and/or among the interstices thereof. The particles or droplets may consist solely of the acetoacetic acid, salt, ester, or amide or the solution thereof, or they may incorporate additional substance(s), including, but not limited to, the above-mentioned primary substances, and pharmaceutically acceptable excipients, adjuvants, diluents, and/or carriers. The solid material may be rigid, or it may be a plastic, rubber, gel and/or foam material, and it may take any form, for example, lump, block, bar, pellet, sheet, film, membrane, fiber, mat, mesh, or matrix form.

Tagging a pharmaceutical with acetoacetate, or a derivative thereof, permits easy detection of subject compliance with prescribed therapeutic regimes by virtue of detecting breath acetone using an acetone specific enzyme system according to the present invention. Thus, subjects mentally impaired due to age or disease, mentally ill subjects, or any other poorly compliant subject can be monitored for drug dosages in a noninvasive manner. By integrating an acetone-specific biosensor with an analysis device linked to, for example, the Internet, instant results for home monitoring of a subject can be obtained. In this manner, acetone-specific biosensors may be employed to ensure health care services are being delivered to a given subject, to test the bio-release of drug formulations in clinical test settings, and to test the release of delayed or controlled release drug formulations over time. Acetone-specific biosensors may also be useful in a biotic environment, such as part of a medical device, implant, and the like. Such devices and implants include drug delivery implants, cosmetic implants, prosthetic implants, and bionic implants.

As noted above, acetoacetic acid is a solid at room temperature. Thus, acetoacetic acid and its pharmaceutically acceptable salts and pharmaceutically acceptable esters and amides that are solid at room temperature are appropriate for use in, for example, powdered, granular, pill, tablet, capsule, implant, and solution formulations. The pharmaceutically acceptable salts and pharmaceutically acceptable esters and amides of acetoacetic acid that are liquid at room temperature are appropriate for use in, for example, liquid formulations (for example, elixirs, syrups, drops, and liquid capsules) and semi-liquid formulations (for example, pastes, creams, and ointments). Preferred solid formulations include pill, tablet, and capsule formulations, more preferably non-chewable pills, tablets, and capsules, and also include implant formulations. Preferred solution, liquid, and semi-liquid formulations include injectable and infusible formulations, more preferably parenteral injectable and infusible formulations, and also include implant formulations.

The term "alkyl" when used in regard to pharmaceutically acceptable salts, esters, and amides is defined herein as "aliphatic. "Preferred "alkyl" groups include $C_1$-$C_{10}$ aliphatic groups, more preferably unsaturated $C_1$-$C_{10}$ aliphatic groups, still more preferably unsaturated $C_1$-$C_6$ aliphatic groups. Even more preferably, where a straight-chain alkyl group is used, it is preferably an unsaturated $C_1$-$C_4$ aliphatic group.

An example of drug tagging via use of an acetone-specific biosensor would be monitoring the intake of lithium carbonate by a subject diagnosed with bipolar disorder. Fairly strict titrations of lithium are needed to achieve reasonable plasma levels of for effectiveness without incurring excess levels, which can be fatal. Thus, a capsule of 300 mg lithium carbonate may be reformulated to contain 200 mg of sodium acetoacetate, which is administered to a subject in a standard fashion (for example, four times per day). Subject compliance can then be monitored using an acetone-specific biosensor to detect acetone released from the acetoacetate tag. By interfacing the biosensor with the Internet, the subject's physician can log the daily acetone levels measured over a period of time. Serum lithium levels can be simultaneously measured to assign a correlation between acetone measurements and bioavailability of lithium. Thus, a biosensor according to the present invention can be applied to reduce or eliminate the need for invasive (e.g., serum) testing for lithium levels.

Alternatively, the acetone tag may be co-administered with the pharmaceutically active compound in the form of a placebo, instead of being formulated with the compound. Methods of infusing acetoacetate into human subjects are known in the art. Subjects can be infused over a several hour period, for example, for three hours, with Na acetoacetate or free acetoacetic acid administered at approximately 20 µmol/kg/min. Constant perfusion of Na acetoacetate at a rate of 1.36 mmol/min. for three hours has been shown to cause an increase in blood ketone body concentration to 3 µmol mL at the end of perfusion. Constant infusions of 3-$^{14}$C-labeled acetoacetate, sodium salt (for example, infused at a rate of 0.68-0.88 nanocuries per kilogram per minute (mµCi/kg/min.)) permit the tracking of respiratory efflux of $^{14}CO_2$. Thus, perfusion of a tagged acetoacetate together with a drug of interest would provide a means for correlating acetone production with blood bioavailability of a drug of interest.

Also contemplated is a kit for detecting acetone in a sample comprising the acetone-specific enzyme system separate from, or contained within, a biosensor, together with instructions for use. For example, the acetone-specific enzyme system may be adhered to or otherwise disposed on a disposable test strip that may be inserted into a housing, the housing having a port into which a biological sample may be introduced. Alternatively, the biosensor housing and the acetone-specific enzyme system may be fashioned to be a single, disposable unit.

Given the limitations of the known means of detecting acetone in a biological sample, the inventive acetone-specific enzyme systems and biosensors containing these enzyme systems offer the advantages of being more sensitive to low concentrations of acetone, more specific for acetone, and less likely to give false readings due to interference from impurities. Therefore, the inventive acetone-specific biosensors are suitable for use outside the laboratory, and may be portable. Portable acetone-specific biosensors having high sensitivity for acetone would be convenient for monitoring acetone levels in subjects in a variety of settings, yet are expected to exhibit at least the level of accuracy attributed to traditional nitroprusside tests for acetone in body fluids.

The various signal amplification schemes disclosed herein may also be employed in systems for detection components other than acetone, by substituting for the acetone-specific enzyme, an different enzyme capable of generating the same cofactor (e.g., NAD(P)H or NAD(P)+) or reaction by-product as the acetone-specific enzyme.

The concepts and data presented here provide avenues for exploiting an enzyme-based biosensor specific for acetone detection. While the invention has been illustrated by the preferred embodiments described herein, those skilled in the art will appreciate that various other modifications will be apparent and can be readily made by such artisans without departing from the spirit and scope of the invention. Accordingly, it is not intended that the scope of the appended claims be limited to the preferred embodiments described herein, but broadly construed the full extent supported by the disclosure as a whole. The disclosures of all references cited are hereby incorporated herein by reference.

REFERENCES

1. Kundu, S. K., et al., *Breath acetone analyzer: diagnostic tool to monitor dietary fat loss*. Clin Chem, 1993. 39(1): p. 87-92.
2. Kundu, S. K., Ketone or aldehyde analyte detection using a solid matrix to which a nitroprusside salt is coupled and a solid matrix binding an amine, EP 279069 A (19880824), EP 87119013A (19871222), and U.S. Pat. No. 4,970,172 (1990).
3. Kundu, S. K., Method and device for ketone measurements, in U.S. Pat. No. 4,970,172 (1990).
4. Laffel, L., *Ketone bodies: a review of physiology, pathophysiology and application of monitoring to diabetes*. Diabetes Metab Res Rev, 1999. 15: p. 412-26.
5. Smith et al., D., *Trace gases in breath of health volunteers when fasting and after a protein-calorie meal: a preliminary study*. Appl Physiol, 1999. 87: p. 1584-88.
6. Rooth, G. and S. Ostenson, *Acetone in alveolar air, and the control of diabetes*. The Lancet, 1966. 11(7473): p. 1102-05.
7. Crofford, O. B., *Diabetes control and complications*. Annu Rev Med, 1995. 46: p. 267-279.
8. Sullivan, F. A., *U.S. Anti-obesity prescriptions drug market*. 1998-2006.
Thompson, D., et al., *Lifetime health and economic consequences of obesity*. Archives of Internal Medicine, 1999. 159: p. 2177.
10. Ricco, A. J. R. M. Crooks, and J. Janata, *Chemical sensors: A perspective of the present and future*. The Electrochemical Society Interface, 1998. Winter: p. 18-24.
11. Kuhn, L. S., *Biosensors: Blockbuster or Bomb? The Electrochemical Society Interface*, 1998. Winter: p. 26-30.
12. Hilditch, P. I. and M. J. Green, *Disposable electrochemical biosensors*. Analyst, 1991. 116: p. 1217-20.
13. Willner, I. and E. Katz, *Integration of Layered Redox Proteins and Conductive Supports for Bioelectronic Applications*. Angew Chem Int Ed Engl, 2000. 39(7): p. 1180-1218.
14. Katakis, I. and E. Dominguez, *Catalytic electrooxidation of NADH for dehydrogenase amperometric biosensors*. Mikrochim Acta, 1997. 126: p. 11-32.
15. Feldman, B., et al., *FreeStyle: a small-volume electrochemical glucose sensor for home blood glucose testing*, WO 00/20626 (2000).
16. Mcaleer, J. F., et al., *Disposable test strips with integrated reagent/blood separation layer*, WO 00/42422 (2000).
17. Mindt, W., P. Racine, and P. Schlaepfer, Enzyme electrode, U.S. Pat. No. 3,838,033 (1973).
18. Hampp, N., A. Silber, and C. Braeuchle, Electrochemical enzyme biosensor, U.S. Pat. No. 5,783,056 (1996).
19. Carter, N., et al., Electrochemical sensor, U.S. Pat. No. 5,628,890 (1997).
20. Wang, J., M. P. Chatrathi, and B. Tian, *Microseparation chips for performing multienzymatic dehydrogenase/oxidase assays.—simultaneous electrochemical measurement of ethanol and glucose*. Anal Chem, 2001. 73(6): p. 1296-1300.
21. Tierney, M. J., et al., *Electroanalysis of glucose in transcutaneously extracted samples*. Electroanalysis, 2000. 12: p. 666-71.
22. Park, J.-K., H.-J. Yee, and S.-R. Kim, *Amperometric biosensor for determination of ethanol vapor*. Biosensors and Bioelectronics, 1995. 10: p. 587-94.
23. Yee, H.-J., J.-K. Park, and S.-T. Kim, *Disposable thick-film amperometric biosensor with multiple working electrodes fabricated on a single substrate*. Sensors and Actuators B, 1996. 34: p. 490-92.
24. Park, J.-K., et al., *Determination of breath alcohol using a differential-type amperometric biosensor based on alcohol dehydrogenase*. Analytica Chimica Acta, 1999. 390: p. 83-91.
25. Park, J.-K. and H.-J. Lee, Biosensor for measuring gas and the manufacturing methods thereof, U.S. Pat. No. 5,656,142 (1997).
26. Dennison, M. J., J. H. Hall, and A. P. F. Turner, *Direct monitoring of formaldehyde vapour and detection of ethanol vapour using dehydrogenase-based biosensors*. Analyst, 1996. 121: p. 1769-73.
27. Lukins, H. B. and J. W. Foster, *Utilization of hydrocarbons and hydrogen by mycobacteria*. Z Allg Mikrobiol, 1963. 3(4): p. 251-64.
28. Vestal, J. R. and J. J. Perry, *Divergent metabolic pathways for propane and propionate utilization by a soil isolate*. J Bacteriol, 1969. 99(1): p. 216-21.
29. Taylor, D. G., et al., *The microbial metabolism of acetone*. J Gen Microbiol, 1980. 118: p. 159-70.
30. Ashraf, W., A. Mihdhir, and J. C. Murrell, *Bacterial oxidation of propane*. FEMS Microbiol Lett, 1994. 122(1-2): p. 1-6.
31. Coleman, J. P. and J. J. Perry, *Fate of the C1 product of propane dissimilation in Mycobacterium vaccae*. J Bacteriol, 1984. 160(3): p. 1163-64.
32. Murrell, J. C. and W. Ashraf, *Cell-free assay methods for enzymes of propane utilization*. 1990, Academic Press. p. 26-32.
33. Ashraf, W. and J. C. Murrell, *Gentic, biochemical and immunological evidence for the involvement of two alcohol dehydrogenases in the metabolism of propane by Rhodococcus rhodochrous PNKb1*. Arch Microbiol, 1992. 157: p. 488-92.
34. Casazza, J. P., M. E. Felver, and R. L. Veech, *The metabolism of acetone in rat*. J Biol Chem, 1984. 259(1): p. 231-36.
35. Casazza, J. P., et al., *Serum acetone and liver acetone monooxygenase activity in pregnant rats, fetuses, and neonates: reversible pretranslational reduction of cytochrome P450IIE1 (P450IIE1) during pregnancy*. Arch Biochem Biophys, 1994. 309(1): p. 111-16.
36. Koop, D. R. and J. P. Casazza, *Identification of ethanol-inducible P-450 isozyme 3a as the acetone and acetol monooxygenase of rabbit microsomes*. J Biol Chem, 1985. 260(25): p. 13607-12.
37. Platen, H. and B. Schink, *Methanogenic degradation of acetone by an enrichment culture*. Arch Microbiol, 1987. 149(2): p. 136-41.
38. Platen, H. and B. Schink, *Anaerobic degradation of acetone and higher ketones via carboxylation by newly isolated denitrifying bacteria*. J Gen Microbiol, 1989. 135 (Pt 4)(1): p. 883-91.
39. Platen, H., P. H. Janssen, and B. Schink, *Fermentative degradation of acetone by an enrichment culture in membrane-separated culture devices and in cell suspensions*. FEMS Microbiol Lett, 1994. 122(1-2): p. 27-32.
40. Bonnet-Smits, E. M., et al., *Carbon dioxide fixation as the initial step in the metabolism of acetone by Thiosphaera pantotropha* J Gen Microbiol, 1988. 134: p. 2281-89.

41. Sluis, M. K., et al., *Involvement of an ATP-dependent carboxylase in a CO2-dependent pathway of acetone metabolism by Xanthobacter strain Py2.* J Bacteriol, 1996. 178(14): p. 4020-26.
42. Ensign, S. A., et al., *New roles for $CO_2$ in the microbial metabolism of aliphatic epoxides and ketones.* Arch Microbiol, 1998. 169(3): p. 179-87.
43. Birks, S. J. and D. J. Kelly, *Assay and properties of acetone carboxylase, a novel enzyme involved in acetone-dependent growth and $CO_2$ fixation in Rhodobacter capsulatus and other photosynthetic and denitrifying bacteria.* Microbiology, 1997. 143: p. 755-66.
44. Sluis, M. K. and S. A. Ensign, *Purification and characterization of acetone carboxylase from Xanthobacter strain Py2.* Proc Natl Acad Sci USA, 1997. 94(16): p. 8456-61.
45. Sluis, M. K., R. A. Larsen, J. G. Krum, R. Anderson, W. W. Metcalf and S. A. Ensign, *Biochemical, molecular and genetic analyses of the acetone carboxylases from Xanthobacter st. Py2 and Rhodobacter capsulatus st. B10.* J Biol Chem, (submitted).
46. Ashraf, W. and J. C. Murrell, *Purification and characterization of a $NAD^+$-dependent secondary alcohol dehydrogenase from propane-grown Rhodococcus rhodochrous PNKb1.* Arch Microbiol, 1990. 153: p. 163-68.
47. Coleman, J. P. and J. J. Perry, *Purification and characterization of the secondary alcohol dehydrogenase from propane-utilizing Mycobacterium vaccae strain JOB-5.* J Gen Microbiol, 1985. 131(Pt 11)(2): p. 2901-07.
48. Hou, C. T., et al., *Stereospecificity and other properties of a novel secondary-alcohol-specific alcohol dehydrogenase.* Eur J Biochem, 1981. 119(2): p. 359-64.
49. Schulte, H., W. Hummel, and M. R. Kula, *Purification and characterization of a nicotinamide adenine dinucleotide-dependent secondary alcohol dehydrogenase from Candida boidinii.* Biochim Biophys Acta, 1982. 716(3): p. 298-307.
50. Widdel, F., *Growth of methanogenic bacteria in pure culture with 2-propanol and other alcohols as hydrogen donors.* Appl Environ Microbiol, 1986. 51: p. 1056-62.
51. Gottschalk., G., *Bacterial Metabolism.* 2nd ed. 1986, New York, N.Y.: Springer-Verlag New York, Inc.
52. Al-Kassim, L. S. and C. S. Tsai, *Studies of NADP(+)-preferred secondary alcohol dehydrogenase from Thermoanaerobium brockii.* Biochem Cell Biol, 1990. 68(6): p. 907-13.
53. Wang, J., N. Naser, and D. Lopez, *Organic phase biosensing of secondary alcohols with a T. brockii alcohol dehydrogenase electrode.* Biosens Bioelectron, 1994. 9(3): p. 225-30.
54. Boujtita, M., J. P. Hart, and R. Pittson, *Development of a disposable ethanol biosensor based on a chemically modified screen printed electrode coated with alcohol oxidase for the analysis of beer.* Biosens Bioelectron, 2000. 15(5-6): p. 257-63.
55. Gonchar, M. V., et al., *Microbial O2-and H2O2-electrode sensors for alcohol assays based on the use of permeabilized mutant yeast cells as the sensitive bioelements.* Biosens Bioelectron, 1998. 13(9): p. 945-52.
56. Pandey, P. C., et al., *Ethanol biosensors and electrochemical oxidation of NADH.* Anal Biochem, 1998. 260(2): p. 195-203.
57. Rank, M., et al., *On-line monitoring of ethanol, acetaldehyde and glycerol during industrial fermentations with Saccharomyces cerevisiae.* Appl Microbiol Biotechnol, 1995. 42(6): p. 813-17.
58. Laemmli, U. K., *Cleavage of structural proteins during the assembly of the head of bacteriophage T4.* Nature, 1970. 227: p. 680-85.
59. Chromy, V., J. Fischer, and V. Kulhanek, *Re-evaluation of EDTA-chelated biuret reagent.* Clin Chem, 1974. 20: p. 1362-63.
60. Kuhr, W. G., et al., *Dehydrogenase-modified carbon-fiber microelectrodes for the measurement of neurotransmitter dynamics. 1. NADH voltammetry.* Anal Chem, 1993. 65(5): p. 617-22.
61. Argall, M. E. and G. D. Smith, *The use of trehalose-stabilized lyophilized methanol dehydrogenase from Hyphomicrobium X for the detection of methanol.* Biochem Mol Biol Int, 1993. 30(3): p. 491-97.
62. Brock, T. D., et al., *Biology of Microorganisms.* Seventh ed. 1994, Englewood Cliffs, N.J.: Prentice Hall.
63. Stewart, A. A. & S. Scott, *Test strip*, WO 99/58709 (1999), Abbott Laboratories, 100 Abbott Park Road, Abbott Park, Ill. 60064-3500.
64. Batchelor, M. J., M. J. Green, and C. L. Sketch, *Amperometric assay for the ketone body 3-hydroxybutyrate.* Analytica Chimica Acta, 1989. 221: p. 289-94.
65. Elving, P. J., et al., *NAD/NADH a model redox system: mechanism, mediation, modification by the environment.* Bioelectrochemistry and Bioenergetics, 1982. 9: p. 365-78.
66. Karyakin, A. A., O. A. Bobrova, and E. E. Karyakina, *Electroreduction of $NAD^+$ to enzymatically active NADH at poly(neutral red) modified electrodes.* J Electroanal Chem, 1995. 399: p. 179-84.
67. Hollmann, F., A. Schmid, and E. Steckhan, *The First Synthetic Application of a Monooxygenase Employing Indirect Electrochemical NADH Regeneration.* Angew Chem Int Ed Engl, 2001. 40(1): p. 169-71.
68. Gajovic, N., et al., *Operation of a miniature redox hydrogel-based pyruvate sensor in undiluted deoxygenated calf serum.* Anal Chem, 2000. 72(13): p. 2963-68.
69. Bartlett, P. N., P. R. Birkin, and J. H. Wang, *An enzyme switch employing direct electrochemical communication between horseradish peroxidase and a poly(aniline) film.* Anal Chem, 1998. 70: p. 3685-94.
70. Cornish-Bowden, A., *Fundamentals of Enzyme Kinetics.* Revised ed. 1995, Princeton, N.J.: Princeton University Press.
71. Parellada, J., et al., *A new type of hydrophilic carbon paste electrodes for biosensor manufacturing: binder paste electrodes.* Biosens Bioelectron, 1997. 12(4): p. 267-75.
72. Sono, M., et al., *Heme-containing oxygenases.* Chem Rev, 1996. 96: p. 2841-87.
73. Wallar, B. J. and J. D. Lipscomb, *Dioxygen activation by enzymes containing binuclear non-heme iron clusters.* Chem Rev, 1996. 96: p. 2625-57.
74. O'Leary, M. H. and F. H. Westheimer, *Acetoacetate decarboxylase. Selective acetylation of the enzyme.* Biochemistry, 1968. 7(3): p. 913-19.
75. Shimao, M., et al., *Existence of a novel enzyme, pyrroloquinoline quinone-dependent polyvinyl alcohol dehydrogenase, in a bacterial symbiont, Pseudomonas sp. strain VM15C.* Appl Environ Microbiol, 1986. 51(2): p. 268-75.
76. Zheng, Y. J. and T. C. Bruice, *Conformation of coenzyme pyrroloquinoline quinone and role of $Ca^{2+}$ in the catalytic mechanism of quinoprotein methanol dehydrogenase.* Proc Natl Acad Sci USA, 1997. 94(22): p. 11881-86.
77. Schuhmann, W., et al., *Electron-transfer pathways between redox enzymes and electrode surfaces: reagentless biosensors based on thiol-monolayer-bound and poly-*

78. Suye, S., et al., *Mediated amperometric determination of ammonia with a methanol dehydrogenase from Pseudomonas sp. AM-1 immobilized carbon paste electrode*. Biosens Bioelectron, 1996. 11(5): p. 529-34.
79. Fery, Francoise; Balasse, Edmond O., *Differential effects of sodium acetoacetate and acetoacetic acid infusions on alanine and glutamine metabolism in man*. J. Clin. Invest. 1980. 66(2): p. 323-31.
80. Bradley, J. A.; Swaminathan, R.; Hill, G. L.; Morgan, D. B., *Ketone kinetics in man*. Horm. Metab. Res. 1981. 13(3): p. 131-34.
81. Balasse, E. O.; Fery, F. *Do the ketone bodies exercise control over protein metabolism?* Journ. Annu. Diabetol. Hotel-Dieu 1979. p. 247-57.
82. Fery, F.; Franken, P.; Neef, M. A.; Balasse, E. O., *Influence of muscular exercise on the rates of uptake and oxidation of infused ketone bodies in normal man*. Arch. Int. Physiol. Biochim. 1974. 82(2), p. 381-85.
83. John, R., *Photometric Assays*. In: Enzyme Assays (Eisenthal, R and Danson, M., eds.), 1993. p. 59-92. IRL Press, New York.
84. Skoog, D. A., D. M. West, and F. J. Holler, *Fundamentals of Analytical Chemistry*. Fifth edition. 1988, New York, N.Y., Saunders College Publishing.
85. B. Danielsson and K. Mosbach, *Enzyme electrode probes*. Methods in Enzymology, 1988. 137: p. 3-28.
86. C. Eggenstein, M. Borchardt, C. Diekmann, B. Grundig, C. Dumschat, K. Cammann, M. Knoll, and F. Spencer, *A disposable biosensor for urea determination in blood based on an ammonium sensitive transducer*. Biosens. And Bioelectron. 1999, 14(1): p. 33-41
87. A. K. Williams and J. T. Hupp, *Sol-gel—encapsulated alcohol dehydrogenase as a versatile, environmentally stabilized sensor for alcohols and aldehydes*. J. Am. Chem. Soc., 1998, 120: p. 4366-71.
88. D. R. Koop and J. P. Casazza, *Identification of ethanol-inducible P-450 isozyme 3a as the acetone and acetol monooxygenase of rabbit microsomes*. J. Biol. Chem., 1985, 260: p. 13607-12.
89. D. Voet & J. G. Voet, *Biochemistry*, 1990. p. 417 (Table 15-4). John Wiley & Sons, Inc. (citing P. Loach, in *Handbook of Biochemistry and Molecular Biology*, (G. D. Fasman, ed.), Third edition, 1976. Vol. 1, p. 123-30. CRC Press, Inc.)
90. G Michal et al., *Chemical Design of Indicator Reactions for the Visible Range*, in H U Bergmeyer, ed., *Methods of Enzymatic Analysis*, Third edition, 1983. Vol. 1, p. 197-232 (section 2.6).
91. *Polarography. In: Methods of Enzymatic Analysis*, (H U Bergmeyer, ed.). Third edition, 1983. Vol. 1, p. 405-12.
92. R A John, *Photometric Assays*. In: R. Eisenthal & M J Danson, *Enzyme Assays: A Practical Approach*, 1993. p. 59-92.
93. J P Hart et al., *Development of a Disposable Amperometric NH4+ Biosensor Based on a Chemically Modified Screen-Printed Carbon Electrode Coated with Glutamate Dehydrogenase, 2-Oxoglutarate, and NADH*. Electroanalysis 1999. 11(6): p. 406-11.
94. P Vanysek, *Electrochemical Series*. In: R C Weast, ed., *CRC Handbook of Chemistry and Physics*. Seventieth edition, 1989. p. D-151-D-160.
95. Wollenberger, U., F., Lisdat and F. W. Scheller, *Enzymatic substrate recycling electrodes*. EXS, 1997. 81(9-10): p. 45-69.
96. Pfeifer, D., F. W. Scheller, C. J. McNeil and T. Schulmeister, *Cascade-like exponential substrate amplification in enzyme sensors*, Biosensors and Bioelectronics, 1995, 10: p. 169-80.
97. Raba, J. and H. A. Mottola, *On-line enzymatic amplification by substrate cycling in a dual bioreactor with rotation and amperometric detection*, Anal. Biochem., 1994, 220: p. 297-302.
98. Schmidt, B., *Oxygen-independent oxidases: A new class of enzymes for application in diagnostics*, Clinica Chimica Acta, 1997, 266: p. 33-37.
99. Fruekilde, P. et al., *Ozonolysis at vegetation surfaces: A source of acetone, 4-oxopentanal, 6-methyl-5-heptan-2-one and geranyl acetone*, Atmos. Environ. 1998. 32: p. 1893-1902.

What is claimed is:

1. An acetone-specific enzyme system comprising a secondary alcohol dehydrogenase isolated from *Xanthobacter autotrophicus* Py2 (ATCC® PTA-4779) that selectively catalyzes the reduction of acetone to isopropanol in the presence of NAD(P)H, coupled to a detectable signal mediator, wherein the secondary alcohol dehydrogenase comprises a polypeptide having a tetradecameric N-terminal amino acid sequence of SEQ ID NO:7, said polypeptide being capable of being degraded to form one or more fragments each having the amino acid sequence selected from SEQ ID NO:8 to SEQ ID NO:19.

2. The acetone-specific enzyme system according to claim 1, wherein the acetone-specific enzyme system is coupled to a signal mediator detected by electrochemical or photometric means.

3. The acetone-specific enzyme system according to claim 2, wherein the acetone-specific enzyme system is secondary alcohol dehydrogenase (S-ADH) with concomitant NAD(P)H oxidation, or S-ADH catalyzed NAD(P)$^+$ formation coupled to $H_2O_2$ production.

4. The acetone-specific enzyme system according claim 2, wherein the signal mediator is a member of any one of organic cofactors, inorganic cofactors, indicators, electron transfer mediators, photometric mediators, enzyme reaction by-products, or combinations thereof.

5. The acetone-specific enzyme system according to claim 4, wherein a signal from the electrochemically detected signal mediator is linearly or exponentially amplified by recycling enzyme substrates to magnify electrochemical signal output.

6. The enzyme-system of claim 1 wherein the secondary alcohol dehydrogenase isolated from *Xanthobacter autotrophicus* Py2 (ATCC® PTA-4779) comprises a protein having NAD$^+$-dependent secondary alcohol dehydrogenase activity, having the ability to reduce acetone to isopropanol, and having specific activity for ketones and secondary alcohols;

(A) said protein (1) having, for the oxidation of isopropanol to acetone, a pH optimum of approximately 7.8, and (2) having, for the oxidation of alcohols, an average specific activity ratio for secondary-to-primary alcohols of at least 50:1 when tested at pH 7.8 under equivalent conditions individually with C3-C5 straight chain secondary alcohols and with C2-C5 straight chain primary alcohols;

(B) said protein having, for the reduction of acetone to isopropanol, (1) a pH optimum of approximately 6.2, (2) an apparent $K_m$ of approximately 144+/−18 μM, (3) an apparent $V_{max}$ of approximately 43.4+/−1.2 μmmol acetone reduced·min$^{-1}$·mg$^{-1}$ protein, (4) an apparent $k_{cat}$ of approximately 30.4 sec$^{-1}$, (5) an apparent $k_{cat}/K_m$ of approximately 2.1×10$^5$, and (6) a $K_m$ for NADH of approximately 5.1+/−0.4 μM; and (C) said protein comprising at least one polypeptide molecule, (1) said polypeptide molecule having (a) a molecular mass of approximately 37.1 kDa as determined by mass spectrometry, (b) a pI of approximately 7.4 as determined by isofocusing electrophoresis, and (c) a tetradecameric N-terminal amino acid sequence of SEQ ID NO:7, and (2) said polypeptide molecule being capable of being degraded to form fragments having the amino acid sequences of SEQ ID NO:8 to SEQ ID NO:19.

7. The enzyme-system of claim 6 wherein the secondary alcohol dehydrogenase isolated from *Xanthobacter autotrophicus* Py2 (ATCC® PTA-4779) comprises a polypeptide molecule purified from the protein according to claim 6, (1) said polypeptide molecule having (a) a molecular mass of approximately 37.1 kDa as determined by mass spectrometry, (b) a pI of approximately 7.4 as determined by isofocusing electrophoresis, and (c) a tetradecameric N-terminal amino acid sequence of SEQ ID NO:7, and (2) said polypeptide molecule being capable of being degraded to form fragments having the amino acid sequences of SEQ ID NO:8 to SEQ ID NO:19.

* * * * *